United States Patent
Beg et al.

(10) Patent No.: US 9,115,388 B2
(45) Date of Patent: Aug. 25, 2015

(54) GENE SIGNATURE FOR THE PREDICTION OF NF-KAPPAB ACTIVITY

(71) Applicant: H. Lee Moffitt Cancer Center and Research Institute, Inc., Tampa, FL (US)

(72) Inventors: Amer A. Beg, Tampa, FL (US); Steven A. Enkemann, Lutz, FL (US); Dung-Tsa Chen, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/355,385

(22) PCT Filed: Nov. 1, 2012

(86) PCT No.: PCT/US2012/063087
§ 371 (c)(1),
(2) Date: Apr. 30, 2014

(87) PCT Pub. No.: WO2013/067198
PCT Pub. Date: May 10, 2013

(65) Prior Publication Data
US 2014/0302060 A1 Oct. 9, 2014

Related U.S. Application Data

(60) Provisional application No. 61/554,314, filed on Nov. 1, 2011.

(51) Int. Cl.
| | |
|---|---|
| A61K 31/436 | (2006.01) |
| A61K 31/05 | (2006.01) |
| A61K 31/353 | (2006.01) |
| A61K 31/4468 | (2006.01) |
| A61K 38/06 | (2006.01) |
| A61K 38/20 | (2006.01) |
| A61K 35/17 | (2015.01) |
| A61K 35/30 | (2015.01) |
| A61K 31/4965 | (2006.01) |
| C12Q 1/68 | (2006.01) |

(52) U.S. Cl.
CPC .............. *C12Q 1/6813* (2013.01); *A61K 31/05* (2013.01); *A61K 31/353* (2013.01); *A61K 31/436* (2013.01); *A61K 31/4468* (2013.01); *A61K 31/4965* (2013.01); *A61K 35/17* (2013.01); *A61K 35/30* (2013.01); *A61K 38/06* (2013.01); *A61K 38/2013* (2013.01); *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,875,274 | B2 | 1/2011 | Sikic et al. |
| 2006/0063190 | A1 | 3/2006 | Fischer et al. |
| 2009/0215053 | A1 | 8/2009 | Galon et al. |
| 2010/0124745 | A1 | 5/2010 | Liew |

FOREIGN PATENT DOCUMENTS

| | | |
|---|---|---|
| EP | 1777523 | 4/2007 |
| WO | WO 2008/069881 | 6/2008 |
| WO | WO 2009/117004 | 9/2009 |
| WO | WO 2010/102157 | 9/2010 |

OTHER PUBLICATIONS

Harhaj et al, "Regulation of NF-kB by deubitinases", Immunol. Rev. 246 (1), 107-124 (2012).*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
International Search Report and Written Opinion in International Application No. PCT/US2012/063087, mailed Feb. 1, 2013, 16 pages.
International Preliminary Report on Patentability in International Application No. PCT/US2012/063087, mailed May 15, 2014, 9 pages.
Acharyya et al., "A CXCL1 paracrine network links cancer chemoresistance and metastasis," Cell, 2012, 150:165-178.
Barbie et al., "Systematic RNA interference reveals that oncogenic KRAS-driven cancers require TBK1," Nature, 2009, 462:108-112 (Author Manuscript).
Basseres and Baldwin, "Nuclear factor-kappaB and inhibitor of kappaB kinase pathways in oncogenic initiation and progression," Oncogene, 2006, 25:6817-6830.
Basseres et al., "Requirement of the NF-κB subunit p65/RelA for K-Ras-induced lung tumorigenesis," Cancer Res., 2010, 70:3537-3546.
Beg et al., "Tumor necrosis factor and interleukin-1 lead to phosphorylation and loss of IkB: a mechanism for NF-κB activation," Mol. Cell Biol., 1993, 13:3301-3310.
Ben-Neriah and Karin, "Inflammation meets cancer, with NF-κB as the matchmaker," Nature Immunol., 2011, 12:715-723.
Beroukhim et al., "The landscape of somatic copy-number alteration across human cancers," Nature, 2010, 463:899-905 (Author Manuscript).
Bild et al., "Oncogenic pathway signatures in human cancers as a guide to targeted therapies," Nature, 2006, 439:353-357.
Boehm et al., "Integrative genomic approaches identify IKBKE as a breast cancer oncogene," Cell, 2007, 129:1065-1079.
Bonizzi and Karin, "The two NF-κB activation pathways and their role in innate and adaptive immunity," Trends Immunol , 2004, 25:280-288.

(Continued)

*Primary Examiner* — James Martinell
(74) *Attorney, Agent, or Firm* — Fish & Richardson P.C.

(57) ABSTRACT

Methods for predicting NF-kappaB (NF-kB) activity in a tumor, and more particularly to methods for predicting survival and therapeutic outcome, and selecting therapy in subjects with tumors, e.g., adenocarcinomas, e.g., lung adenocarcinomas and melanomas.

9 Claims, 30 Drawing Sheets

(56) References Cited

OTHER PUBLICATIONS

Bromley et al., "Orchestrating the orchestrators: chemokines in control of T cell traffic," Nature Immunol., 2008, 9:970-980.
Chang et al., "A genomic strategy to elucidate modules of oncogenic pathway signaling networks," Mol Cell, 2009, 34:104-114.
Chen et al., "Prognostic and predictive value of a malignancy-risk gene signature in early-stage non-small cell lung cancer," J Nat Cancer Inst., 2011, 103:1859-1870.
Chen et al., "Proliferative genes dominate malignancy-risk gene signature in histologically-normal breast tissue," Breast Cancer Res Treatment, 2010, 119:335-346 (Author Manuscript).
Chen et al., "Evaluation of malignancy-risk gene signature in breast cancer patients," Breast Cancer Res Treatment, 2010, 120:25-34 (Author Manuscript).
Chu et al., "Suppression of tumor necrosis factor-induced cell death by inhibitor of apoptosis c-IAP2 is under NF-kappaB control," Proc Natl Acad Sci USA, 1997, 94:10057-10062.
Dejardin et al., "The lymphotoxin-beta receptor induces different patterns of gene expression via two NF-kappaB pathways," Immunity, 2002, 17:525-535.
Downward, "Targeting RAS signalling pathways in cancer therapy," Nat Rev Cancer, 2003, 3:11-22.
Downward, "Targeting RAS and PI3K in lung cancer," Nat Med., 2008,14:1315-1316.
Fridman, Prognostic and predictive impact of intra- and peritumoral immune infiltrates, Cancer Research, 2011, 71:5601-5605.
Gommerman and Browning, "Lymphotoxin/light, lymphoid microenvironments and autoimmune disease," Nature Rev Immunol., 2003, 3:642-655.
Greten et al., "IKKβ links inflammation and tumorigenesis in a mouse model of colitis-associated cancer," Cell, 2004, 118:285-296.
Hacker and Karin, "Regulation and function of IKK and IKK-related kinases," Sci STKE, 2006, 2006:re13, 19 pages.
Harlin et al., "Chemokine expression in melanoma metastases associated with CD8+ T-cell recruitment," Cancer Res., 2009, 69:3077-3085.
Hayden and Ghosh, "Signaling to NF-κB ," Genes Dev., 2004, 18:2195-2224.
Hernandez et al., "Activation of NF-κB signaling by inhibitor of NF-κB kinase beta increases aggressiveness of ovarian cancer," Cancer Res., 2010, 70:4005-4014.
Hinata et al., "Divergent gene regulation and growth effects by NF-kappa B in epithelial and mesenchymal cells of human skin," Oncogene, 2003, 22:1955-1964.
Hoffmann and Baltimore, "Circuitry of nuclear factor κB signaling," Immunol Rev., 2006, 210:171-186.
Karin, "Nuclear factor-κB in cancer development and progression," Nature, 2006, 441:431-436.
Karin and Ben-Neriah, "Phosphorylation meets ubiquitination: the control of NF-κB activity," Annu Rev Immunol., 2000, 18:621-663.
Karin and Greten, "NF-κB: linking inflammation and immunity to cancer development and progression," Nat Rev Immunol., 2005, 5:749-759.
Li and Verma, "NF-κB regulation in the immune system," Nat Rev Immunol., 2002, 2:725-734.
Maeda et al., "IKKβ couples hepatocyte death to cytokine-driven compensatory proliferation that promotes chemical hepatocarcinogenesis," Cell, 2005, 121:977-990.
Mantovani et al., "Cancer-related inflammation," Nature, 2008, 454:436-444.
Mayo et al., "Requirement of NF-κB activation to suppress p53-independent apoptosis induced by oncogenic Ras," Science, 1997, 278:1812-1815.
Meylan et al., "Requirement for NF-κB signalling in a mouse model of lung adenocarcinoma," Nature, 2009, 462:104-107 (Author Manuscript).
Moran et al., "RANTES expression is a predictor of survival in stage I lung adenocarcinoma," Clinical Cancer Res., 2002, 8:3803-3812.
Packham, "The role of NF-κB in lymphoid malignancies," Br J Haematol., 2008, 143:3-15.
Pages et al., "Effector memory T cells, early metastasis, and survival in colorectal cancer," N Engl J Med., 2005, 353:2654-2666.
Qian et al., "CCL2 recruits inflammatory monocytes to facilitate breast-tumour metastasis," Nature, 2011, 475:222-225 (Author Manuscript).
Sharma et al., "Epidermal growth factor receptor mutations in lung cancer," Nat Rev Cancer, 2007, 7:169-181.
Shedden et al., "Gene expression-based survival prediction in lung adenocarcinoma: a multi-site, blinded validation study," Nat Med., 2008, 14:822-827 (Author Manuscript).
Shiao et al., "Immune microenvironments in solid tumors: new targets for therapy," Genes Dev., 2011, 25:2559-2572.
Sparmann and Bar-Sagi, "Ras-induced interleukin-8 expression plays a critical role in tumor growth and angiogenesis," Cancer Cell, 2004, 6:447-458.
Staudt, "Oncogenic activation of NF-κB," Cold Spring Harb Perspect Biol., 2010, 2:a000109, 31 pages.
Takahashi et al., "Tobacco smoke promotes lung tumorigenesis by triggering IKKβ- and JNK1-dependent inflammation," Cancer Cell, 2010, 17:89-97.
Torabian et al., "Ribozyme-mediated targeting of IκBγ inhibits melanoma invasion and metastasis," Am J Pathol., 2009, 174:1009-1016.
Valenzuela et al., "PKCθ is required for alloreactivity and GVHD but not for immune responses toward leukemia and infection in mice," J Clin Invest., 2009, 119:3774-3786.
Vallabhapurapu and Karin, "Regulation and function of NF-κB transcription factors in the immune system," Annu Rev Immunol , 2009, 27:693-733.
Wang et al., "NF-κB antiapoptosis: induction of TRAF1 and TRAF2 and c-IAP1 and c- IAP2 to suppress caspase-8 activation," Science, 1998, 281:1680-1683.
Wang et al., "Distinct roles of different NF-κB subunits in regulating inflammatory and T cell stimulatory gene expression in dendritic cells," J Immunol., 2007, 178:6777-6788.
Wang et al., "Lack of essential role of NF-κB p50, RelA, and cRel subunits in virus-induced type 1 IFN expression," J Immunol., 2007, 178:6770-6776.
Weber "Immune checkpoint proteins: a new therapeutic paradigm for cancer—preclinical background: CTLA-4 and PD-1 blockade," Seminars Oncol., 2010, 37:430-439.
Wolf et al., "The unexpected role of lymphotoxin beta receptor signaling in carcinogenesis: from lymphoid tissue formation to liver and prostate cancer development," Oncogene, 2010, 29:5006-5018.
Xue et al., "Response and Resistance to NF-κB Inhibitors in Mouse Models of Lung Adenocarcinoma," Cancer Discovery, 2011, 1:236-247.
Zhang et al., "Intratumoral T cells, recurrence, and survival in epithelial ovarian cancer," N Engl J Med., 2003, 348:203-213.
Zhu et al., "Prognostic and predictive gene signature for adjuvant chemotherapy in resected non-small-cell lung cancer," J Clinical Oncol., 2010, 28:4417-4424.
Harhaj and Dixit, "Deubiquitinases in the regulation of NF-κB signaling," Cell Res., 2011, 21:22-39 (Author Manuscript).

\* cited by examiner

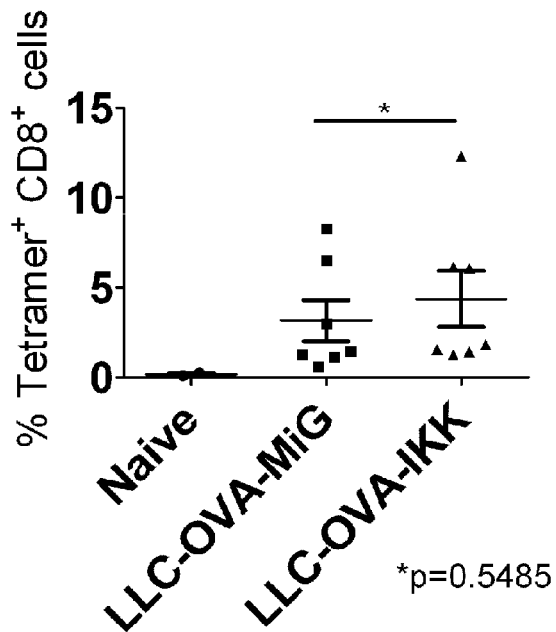
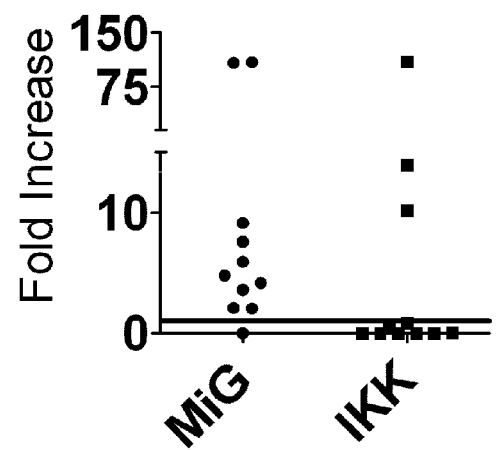
FIG. 1E　　　FIG. 1F
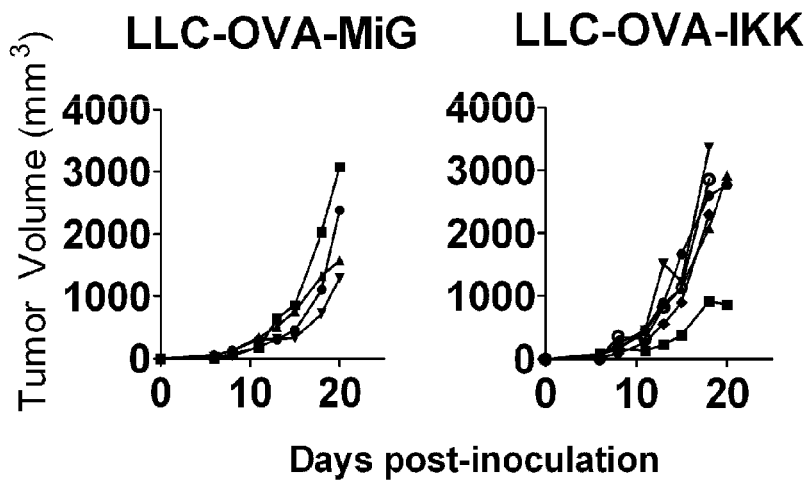
FIG. 1G

*p value=0.0256

Other lines: A549 and H358

GENE SIGNATURE FOR THE PREDICTION OF NF-KAPPAB ACTIVITY

CLAIM OF PRIORITY

This application is a U.S. National Phase Application of International Patent Application No. PCT/US2012/063087 filed Nov. 1, 2012, which claims the benefit of U.S. Provisional Patent Application No. 61/554,314, filed Nov. 1, 2011. The entire contents of the foregoing are incorporated by reference herein.

FEDERALLY SPONSORED RESEARCH OR DEVELOPMENT

This invention was made with Government support under Grant Nos. W81XWH-08-2-0101 awarded by the Department of Defense (ARMY/MRMC) and SPORE NCI P50 CA119997 awarded by the National Institutes of Health. The Government has certain rights in the invention.

TECHNICAL FIELD

This invention relates to methods for predicting NF-kappaB (NF-kB) activity in a tumor, and more particularly to genes and gene signatures that predict survival and therapeutic outcome in subjects with tumors, e.g., adenocarcinoma, e.g., lung adenocarcinoma or melanoma.

BACKGROUND

The NF-kB family of transcription factors plays a crucial role in many cellular responses. They exist as homodimers or heterodimers of 5 distinct proteins: p50, p52, p65/RelA, RelB and cRel (Li and Verma, 2002. Nat Rev Immunol 2:725-734; Hayden and Ghosh, 2004. Genes Dev 18:2195-2224). NF-kB activation typically occurs by nuclear translocation following inducible phosphorylation of inhibitory IkB proteins by the IKKa/b (IkB kinase) complex (Hayden and Ghosh, 2004. Genes Dev 18:2195-2224; Hoffmann, and Baltimore, 2006. Immunol Rev 210:171-186; Karin and Ben-Neriah, 2000. Annu Rev Immunol 18:621-663; Vallabhapurapu and Karin, 2009. Annu Rev Immunol 27:693-733). Activation of the major conventional or canonical subunits p50, p65/RelA and cRel by inflammatory cytokines such as TNFa and IL-1a/b requires IKKb while non-conventional or non-canonical p52 and RelB subunits require IKKa (Bonizzi and Karin, 2004. Trends Immunol 25:280-288; Hacker and Karin, 2006. Sci STKE 2006:re13). A multitude of functions have been attributed to canonical NF-kB subunits, which include roles in inflammation and immunity, as well as in cell proliferation and survival. A tumor-promoting function for NF-kB in lymphomas has been known for some time (Staudt, 2010. Cold Spring Harb Perspect Biol 2:a000109; Packham, 2008. Br J Haematol 143:3-15). NF-kB was implicated in the Ras pathway (Mayo et al., 1997. Science 278:1812-1815) but the role of NF-kB in solid malignancies, although suspected, was not clear. Recent studies in mice and human cell lines have defined a key role for NF-kB in K-Ras-induced lung cancer ((Barbie et al., 2009. Nature 462:108-112; Meylan et al., 2009. Nature 462:104-107; Basseres et al., 2010. Cancer Res 70:3537-3546). This is likely through NF-kB activation via IKKb and/or TBK1 kinase by oncogenic K-Ras (Barbie et al., 2009. Nature 462:108-112; Meylan et al., 2009. Nature 462: 104-107; Basseres et al., 2010. Cancer Res 70:3537-3546). It is not known whether NF-kB plays a general or genetic mutation-specific role in lung cancer development. An additional key role of IKKb/NF-kB in inflammation-promoting non-tumor myeloid cell types has also been shown to be critical in solid malignancies (Maeda et al., 2005. Cell 121:977-990; Karin and Greten, 2005. Nat Rev Immunol 5:749-759; Greten et al., 2004. Cell 118:285-296; Takahashi et al., 2010. Cancer Cell 17:89-97).

Inhibition of NF-kB activation represents a promising avenue for therapeutic targeting of lung cancer. However, relatively little is known about the role and activation state of NF-kB in human lung cancer. Most importantly, the inter-relation between NF-kB activation state and disease progression and survival is not known. It is also not known whether NF-kB is only activated in response to specific genetic mutations, e.g., K-Ras mutations. In this respect, one of the main stumbling blocks is the lack of an appropriate functional readout of NF-kB activation in human lung cancer cells. Previous NF-kB signatures have been defined, but not in lung cancer cells (Hinata et al., 2003. Oncogene 22:1955-1964; Boehm et al., 2007. Cell 129:1065-1079; Hernandez et al., 2010. Cancer Res 70:4005-4014).

SUMMARY

The present invention is based, at least in part, on the discovery of a set of genes that can be used to predict NF-kB activity, survival, and outcome in cancers, e.g., carcinoma, e.g., adenocarcinoma, e.g., human lung adenocarcinoma or melanoma.

Thus, in a first aspect, the invention provides methods for predicting NF-kB transcriptional activity in a tumor. The methods include determining gene expression levels for guanylate binding protein 1, interferon-inducible (GBP1); proteasome (prosome, macropain) subunit, beta type, 9 (large multifunctional peptidase 2) (PSMB9); interferon regulatory factor 1 (IRF1); transporter 1, ATP-binding cassette, sub-family B (MDR/TAP) (TAP 1); tumor necrosis factor, alpha-induced protein 3 (TNFAIP3); chemokine (C-C motif) ligand 5 (CCL5); proteasome (prosome, macropain) subunit, beta type, 8 (large multifunctional peptidase 7) (PSMB8); interleukin 32 (IL32); SH2B adaptor protein 3 (SH2B3); and nuclear factor of kappa light polypeptide gene enhancer in B-cells inhibitor, epsilon (NFKBIE) in a sample comprising cells from the tumor; and
comparing the gene expression levels to reference levels;
optionally assigning a score to the tumor based on the comparison of the gene expression levels in the tumor to the reference levels;
wherein the presence of gene expression levels above the reference levels, or a score above a threshold score, indicates that the tumor has high levels of NF-kB activity, and the presence of gene expression levels below the reference levels, or a score below the threshold score indicates that the tumor has low levels of NF-kB activity.

In some embodiments, the methods include identifying a subject as having a tumor having high levels of NF-kB activity, and selecting a treatment for the subject comprising administering an NF-kB inhibitor or immunotherapy.

In some embodiments, the methods include identifying a subject as having a tumor having low levels of NF-kB activity, and selecting a treatment for the subject comprising administering an NF-kB activator and immunotherapy.

In another aspect, the invention provides methods for selecting a treatment for a subject who has a tumor. The methods include determining gene expression levels for GBP1, PSMB9, IRF1, TAP1, TNFAIP3, CCL5, PSMB8, IL32, SH2B3 and NFKBIE in a sample comprising cells from the tumor; and comparing the gene expression levels to reference levels;
optionally assigning a score to the tumor based on the comparison of the gene
expression levels in the tumor to the reference levels;
detecting the presence of gene expression levels above the reference levels, or a score above a threshold score, and selecting a treatment for the subject comprising administering an NF-kB inhibitor or immunotherapy; or
detecting the presence of gene expression levels below the reference levels, or a score below a threshold score, and selecting a treatment for the subject comprising administering an NF-kB activator and immunotherapy.

In another aspect, the invention provides methods for treating a subject who has a tumor. The methods include determining gene expression levels for GBP1, PSMB9, IRF1, TAP1, TNFAIP3, CCL5, PSMB8, IL32, SH2B3 and NFKBIE in a sample comprising cells from the tumor; and
comparing the gene expression levels to reference levels;
optionally assigning a score to the tumor based on the comparison of the gene expression levels in the tumor to the reference levels; and
detecting the presence in the subject of gene expression levels above the reference levels, or a score above a threshold score, and administering a treatment to the subject comprising an NF-kB inhibitor or immunotherapy, or
detecting the presence in the subject of gene expression levels below the reference levels, or a score below a threshold score, and administering a treatment to the subject comprising an NF-kB activator and immunotherapy.

In another aspect, the invention provides methods for predicting outcome in a subject with a tumor. The methods include determining gene expression levels for GBP1, PSMB9, IRF1, TAP1, TNFAIP3, CCL5, PSMB8, IL32, SH2B3 and NFKBIE
in a sample comprising cells from the tumor; and
comparing the gene expression levels to reference levels;
optionally assigning a score to the tumor based on the comparison of the gene expression levels in the tumor to the reference levels;
wherein the presence of gene expression levels below the reference levels, or a score below a threshold score, indicate that the subject is likely to have a poor outcome as compared to a subject who has levels above the reference levels or threshold score, and the presence of gene expression levels above the reference levels, or a score above a threshold score, indicate that the subject is likely to have a better outcome as compared to a subject who has levels below the reference levels or threshold score.

In another aspect, the invention provides methods for predicting outcome in a subject with a tumor. The methods include determining gene expression levels for some or all of CXCL1, CXCL2, CXCL3, IL6, and IL8, e.g., CXCL1, CXCL3, IL6, and IL8, in a sample comprising cells from the tumor; and
comparing the gene expression levels to reference levels;
optionally assigning a score to the tumor based on the comparison of the gene
expression levels in the tumor to the reference levels;
wherein the presence of gene expression levels above the reference levels, or a score above a threshold score, indicate that the subject is likely to have a poor outcome as compared to a subject who has levels below the reference levels or threshold score, and the presence of gene expression levels below the reference levels, or a score below a threshold score, indicate that the subject is likely to have a better outcome as compared to a subject who has levels below the reference levels or threshold score.

In another aspect, the invention provides methods for predicting outcome in a subject with a tumor. The methods include determining gene expression levels of LTB in a sample comprising cells from the tumor; and
comparing the gene expression levels to reference levels;
optionally assigning a score to the tumor based on the comparison of the gene
expression levels in the tumor to the reference levels;
wherein the presence of gene expression levels below the reference levels, or a score below a threshold score, indicate that the subject is likely to have a poor outcome as compared to a subject who has levels above the reference levels or threshold score, and the presence of gene expression levels above the reference levels, or a score above a threshold score, indicate that the subject is likely to have a better outcome as compared to a subject who has levels below the reference levels or threshold score.

In another aspect, the invention provides methods for monitoring treatment in a subject who has a tumor with low NF-kB activity. The methods include determining gene expression levels for GBP1, PSMB9, IRF1, TAP1, TNFAIP3, CCL5, PSMB8, IL32, SH2B3 and NFKBIE in a first sample comprising cells from the tumor; and
comparing the gene expression levels in the first sample to reference levels;
optionally assigning a score to the tumor based on the comparison of the gene expression levels in the first sample to the reference levels;
identifying a subject as having a tumor having low levels of NF-kB activity based on the presence of gene expression levels below the reference levels, or a score below the threshold score;
administering to the subject a treatment, preferably a treatment comprising administering one or both of an NF-kB activator and immunotherapy;
determining gene expression levels for GBP1, PSMB9, IRF1, TAP1, TNFAIP3, CCL5, PSMB8, IL32, SH2B3 and NFKBIE in a subsequent sample comprising cells from the tumor; and
comparing the gene expression levels in the subsequent sample to levels in the first sample, wherein an increase in the levels from the first sample to the subsequent sample indicates that the treatment has been effective, and no change or a decrease in the levels from the first sample to the subsequent samples indicates that the treatment has not been effective.

In some embodiments, the tumor is a carcinoma, e.g., adenocarcinoma, e.g., lung adenocarcinoma or melanoma.

In some embodiments, determining gene expression levels comprises performing an assay to determine gene expression levels in the sample.

In some embodiments, assigning a score to the tumor based on the comparison of the gene expression levels in the tumor to the reference levels comprises using an algorithm to calculate a score.

In some embodiments, the NF-kB activator is an anticancer agent, preferably selected from the group consisting of taxanes, vinca alkaloids, and topoisomerase inhibitors.

In some embodiments, the NF-kB inhibitor is selected from the group consisting of sulfasalazine, Luteolin, rapamycin, temsirolimus and everolimus, caffeic acid phenethylester, SN50, parthenolide, triptolide, wedelolactone, lactacystin, substituted resorcinols, (E)-3-(4-methylphenylsulfonyl)-2-propenenitrile, Bay 11-7082, Bay 11-7821, or Bay 11-7085, Pranlukast, etoposide, bortezomib, MLN9708, PS-1145, tetrahydrocurcuminoids, such as Tetrahydrocurcuminoid CG, extracts of *Paulownia tomentosa* wood, and MG-132 (Z-Leu-Leu-Leu-H).

In some embodiments, the immunotherapy is selected from the group consisting of administration of dendritic cells or peptides with adjuvant; DNA-based vaccines; cytokines (e.g., IL-2); cyclophosphamide; anti-interleukin-2R immunotoxins; and antibodies, virus-based vaccines (e.g., adenovirus), formulations of Toll-like Receptor or RIG-I-like receptor ligands, Adoptive T cell therapy or other cell types.

In some embodiments, the antibodies are selected from the group consisting of anti-CD137, anti-PD1, anti-CD40, anti-PDL1, and anti-CTLA-4 antibodies.

In another aspect, the invention provides methods for predicting NF-kB transcriptional activity in a tumor. The methods include determining gene expression levels for some or all of the genes shown herein, e.g., in Tables A or 1 or 3, or the ten genes GBP1, PSMB9, IRF1, TAP1, TNFAIP3, CCL5, PSMB8, IL32, SH2B3 and NFKBIE, in a sample comprising cells from the tumor; comparing the gene expression levels to reference levels; and assigning a score to the tumor based on the comparison of the gene expression levels in the tumor to the reference levels. A score above a threshold score indicates that the tumor has high levels of NF-kB activity (and conversely, a score below the threshold indicates low NF-kB activity).

In some embodiments, the methods include identifying a subject as having a tumor having high levels of NF-kB activity, and selecting a treatment for the subject comprising administering an NF-kB inhibitor or immunotherapy.

In a further aspect, the invention provides methods of predicting outcome in a subject with cancer. The methods include determining gene expression levels for some or all of CXCL1, CXCL2, CXCL3, and IL8 in a sample comprising cells from the tumor; comparing the gene expression levels to reference levels; and optionally assigning a score to the tumor based on the comparison of the gene expression levels in the tumor to the reference levels. The presence of gene expression levels above the reference levels indicate that the subject is likely to have a poor outcome (and conversely, levels below the reference levels indicate a good outcome).

In some embodiments, the methods include identifying a subject as having a tumor having high gene expression levels, and selecting a treatment for the subject comprising administering an NF-kB inhibitor or immunotherapy.

In yet another aspect, the invention features methods for predicting outcome in a subject with cancer. The methods include determining gene expression levels of LTB in a sample comprising cells from the tumor; comparing the gene expression levels to reference levels; and optionally assigning a score to the tumor based on the comparison of the gene expression levels in the tumor to the reference levels. The presence of gene expression levels above the reference levels indicate that the subject is likely to have an improved outcome.

In some embodiments, the methods include identifying a subject as having a tumor having high LTB gene expression levels, and selecting a treatment for the subject comprising administering an NF-kB inhibitor or immunotherapy.

In another aspect, the invention features methods for predicting outcome in a subject with cancer. The methods include determining gene expression levels for some or all of CCL2, CCL5, LTB, CD83, and RELB in a sample comprising cells from the tumor; and comparing the gene expression levels to reference levels; optionally assigning a score to the tumor based on the comparison of the gene expression levels in the tumor to the reference levels; wherein the presence of gene expression levels above the reference levels indicate that the subject is likely to have an improved outcome.

In some embodiments, the methods include identifying a subject as having a tumor having high gene expression levels, and selecting a treatment for the subject comprising administering an NF-kB inhibitor or immunotherapy.

In some embodiments of the methods described herein, the tumor is a lung adenocarcinoma.

TABLE A

| GenBank ID | GeneSymbol | Gene description |
|---|---|---|
| NM_000214.1 | JAG1 | jagged 1 (Alagille syndrome) |
| NM_001166.3 | BIRC2 | baculoviral IAP repeat-containing 2 |
| NM_001165 | BIRC3 | baculoviral IAP repeat-containing 3 |
| NM_005504.4 | BCAT1 | branched chain aminotransferase 1, cytosolic |
| NM_001710.4 | BF | B-factor, properdin |
| NM_000064.1 | C3 | complement component 3 |
| NM_001025079.1 | CD47 | CD47 antigen (Rh-related antigen, integrin-associated signal transducer) |
| NM_004079.3 | CTSS | cathepsin S |
| NM_015247 | CYLD | cylindromatosis (turban tumor syndrome) |
| NM_001924.2 | GADD45A | growth arrest and DNA-damage-inducible, alpha |
| NM_005238.2 | ETS1 | v-ets erythroblastosis virus E26 oncogene homolog 1 (avian) |
| NM_002053.1 | GBP1 | guanylate binding protein 1, interferon-inducible, 67 kDa |
| NM_001024070.1 | GCH1 | GTP cyclohydrolase 1 (dopa-responsive dystonia) |
| NM_004004.3 | GJB2 | gap junction protein, beta 2, 26 kDa (connexin 26) |
| NM_001511.1 | CXCL1 | chemokine (C-X-C motif) ligand 1 (melanoma growth stimulating activity, alpha) |
| NM_002089.1 | CXCL2 | chemokine (C-X-C motif) ligand 2 |
| NM_002090.2 | CXCL3 | chemokine (C-X-C motif) ligand 3 |
| NM_005514.5 | HLA-B | major histocompatibility complex, class I, B |
| AY732487.1 | HLA-C | major histocompatibility complex, class I, C |
| NM_000201.1 | ICAM1 | intercellular adhesion molecule 1 (CD54), human rhinovirus receptor |
| NM_000600.1 | IL6 | interleukin 6 (interferon, beta 2) |
| NM_002184 | IL6ST | interleukin 6 signal transducer (gp130, oncostatin M receptor) |

TABLE A-continued

| GenBank ID | GeneSymbol | Gene description |
|---|---|---|
| NM_000584.2 | IL8 | interleukin 8 |
| NM_001561.4 | TNFRSF9 | tumor necrosis factor receptor superfamily, member 9 |
| NM_002192.2 | INHBA | inhibin, beta A (activin A, activin AB alpha polypeptide) |
| NM_001570.3 | IRAK2 | interleukin-1 receptor-associated kinase 2 |
| NM_002198.1 | IRF1 | interferon regulatory factor 1 |
| NM_002203.2 | ITGA2 | integrin, alpha 2 (CD49B, alpha 2 subunit of VLA-2 receptor) |
| NM_002205.2 | ITGA5 | integrin, alpha 5 (fibronectin receptor, alpha polypeptide) |
| NM_000632.3 | ITGAM | integrin, alpha M (complement component receptor 3, alpha; also known as CD11b (p170), macrophage antigen alpha polypeptide) |
| AU144005 | ITGAV | integrin, alpha V (vitronectin receptor, alpha polypeptide, antigen CD51) |
| NM_005562.1 | LAMC2 | laminin, gamma 2 |
| NM_009588.1 | LTB | lymphotoxin beta (TNF superfamily, member 3) |
| NM_004994.2 | MMP9 | matrix metallopeptidase 9 (gelatinase B, 92 kDa gelatinase, 92 kDa type IV collagenase) |
| NM_003998.2 | NFKB1 | nuclear factor of kappa light polypeptide gene enhancer in B-cells 1 (p105) |
| NM_002502.2 | NFKB2 | nuclear factor of kappa light polypeptide gene enhancer in B-cells 2 (p49/p100) |
| NM_004556.2 | NFKBIE | nuclear factor of kappa light polypeptide gene enhancer in B-cells inhibitor, epsilon |
| NM_002526 | NT5E | 5'-nucleotidase, ecto (CD73) |
| NM_002581.3 | PAPPA | pregnancy-associated plasma protein A, pappalysin 1 |
| NM_198833.1 | SERPINB8 | serpin peptidase inhibitor, clade B (ovalbumin), member 8 |
| NM_001005376.1 | PLAUR | plasminogen activator, urokinase receptor |
| NM_004159.4 | PSMB8 | proteasome (prosome, macropain) subunit, beta type, 8 (large multifunctional peptidase 7) |
| NM_002800.4 | PSMB9 | proteasome (prosome, macropain) subunit, beta type, 9 (large multifunctional peptidase 2) |
| NM_002818.2 | PSME2 | proteasome (prosome, macropain) activator subunit 2 (PA28 beta) |
| NM_002852.2 | PTX3 | pentraxin-related gene, rapidly induced by IL-1 beta |
| NM_006509.2 | RELB | v-rel reticuloendotheliosis viral oncogene homolog B, nuclear factor of kappa light polypeptide gene enhancer in B-cells 3 (avian) |
| NM_002941.2 | ROBO1 | roundabout, axon guidance receptor, homolog 1 (Drosophila) |
| NM_002982.3 | CCL2 | chemokine (C-C motif) ligand 2 |
| NM_002985.2 | CCL5 | chemokine (C-C motif) ligand 5 |
| NM_004591.1 | CCL20 | chemokine (C-C motif) ligand 20 |
| NM_000593.5 | TAP1 | transporter 1, ATP-binding cassette, sub-family B (MDR/TAP) |
| NM_000544.3 | TAP2 | transporter 2, ATP-binding cassette, sub-family B (MDR/TAP) |
| NM_003190.3 | TAPBP | TAP binding protein (tapasin) |
| NM_003264.3 | TLR2 | toll-like receptor 2 |
| NM_006290.2 | TNFAIP3 | tumor necrosis factor, alpha-induced protein 3 |
| NM_005658.3 | TRAF1 | TNF receptor-associated factor 1 |
| NM_003300.2 | TRAF3 | TNF receptor-associated factor 3 |
| NM_003916 | AP1S2 | adaptor-related protein complex 1, sigma 2 subunit |
| NM_021101.3 | CLDN1 | claudin 1 |
| NM_001012635.1 | IL32 | interleukin 32 |
| NM_001040280.1 | CD83 | CD83 antigen (activated B lymphocytes, immunoglobulin superfamily) |
| NM_004235.3 | KLF4 | Kruppel-like factor 4 (gut) |
| NM_206853.1 | QKI | quaking homolog, KH domain RNA binding (mouse) |
| NM_004289 | NFE2L3 | nuclear factor (erythroid-derived 2)-like 3 |
| NM_014840.2 | NUAK1 | NUAK family, SNF1-like kinase, 1 |
| NM_005110.1 | GFPT2 | glutamine-fructose-6-phosphate transaminase 2 |
| NM_005124 | NUP153 | nucleoporin 153 kDa |
| NM_005475.1 | SH2B3 | SH2B adaptor protein 3 |
| NM_005493 | RANBP9 | RAN binding protein 9 |
| NM_005729.3 | PPIF | peptidylprolyl isomerase F (cyclophilin F) |
| NM_001008211.1 | OPTN | optineurin |
| NM_006058.2 | TNIP1 | TNFAIP3 interacting protein 1 |
| NM_006470.3 | TRIM16 | tripartite motif-containing 16 |
| NM_006662 | SRCAP | Snf2-related CBP activator protein |

TABLE A-continued

| GenBank ID | GeneSymbol | Gene description |
|---|---|---|
| NM_017585.2 | SLC2A6 | solute carrier family 2 (facilitated glucose transporter), member 6 |
| BC067106.1 | GPR176 | G protein-coupled receptor 176 |
| NM_016445.1 | PLEK2 | pleckstrin 2 |
| NM_015714.2 | G0S2 | G0/G1 switch 2 |
| NM_016584.2 | IL23A | interleukin 23, alpha subunit p19 |
| NM_001040458.1 | ARTS-1 | type 1 tumor necrosis factor receptor shedding aminopeptidase regulator |
| NM_178031.2 | HSPA5BP1 | heat shock 70 kDa protein 5 (glucose-regulated protein, 78 kDa) binding protein 1 |
| NM_018370.1 | DRAM | damage-regulated autophagy modulator |
| NM_018351.2 | FGD6 | FYVE, RhoGEF and PH domain containing 6 |
| NM_020183.3 | ARNTL2 | aryl hydrocarbon receptor nuclear translocator-like 2 |
| XM_934503.1 | FAM91A2 | family with sequence similarity 91, member A2 |
| NM_022154.5 | SLC39A8 | solute carrier family 39 (zinc transporter), member 8 |
| NM_022168.2 | IFIH1 | interferon induced with helicase C domain 1 |
| NM_022350.1 | ERAP2 | endoplasmic reticulum aminopeptidase 2 |
| NM_022750.2 | PARP12 | poly (ADP-ribose) polymerase family, member 12 |
| NM_022763.2 | FNDC3B | Caution, check this probeset carefully. This probeset may detect an alternate exon, an alternate termination site, or an overlapping transcript of fibronectin type III domain containing 3B |
| NM_024615.2 | PARP8 | poly (ADP-ribose) polymerase family, member 8 |
| NM_030952.1 | NUAK2 | NUAK family, SNF1-like kinase, 2 |
| NM_031449.3 | ZMIZ2 | zinc finger, MIZ-type containing 2 |
| NM_032413.2 | C15orf48 | chromosome 15 open reading frame 48 |
| NM_014903.3 | NAV3 | neuron navigator 3 |
| NM_138397 | LOC93082 | hypothetical protein BC012317 |
| NM_030968.2 | C1QTNF1 | C1q and tumor necrosis factor related protein 1 |
| NM_173490 | LOC134285 | hypothetical protein LOC134285 |
| NM_001031739.1 | ASB9 | ankyrin repeat and SOCS box-containing 9 |
| NM_178496.2 | C3orf59 | chromosome 3 open reading frame 59 |
| NM_144975 | MGC19764 | hypothetical protein MGC19764 |
| NM_173545.1 | C2orf13 | chromosome 2 open reading frame 13 |
| NM_147156.3 | TMEM23 | transmembrane protein 23 |
| NM_207376.1 | OCC-1 | overexpressed in colon carcinoma-1 |
| XM_498811.2 | KIAA0493 | KIAA0493 protein |
| XM_930678.1 | LOC642441 | hypothetical LOC642441 |
| XM_937100.1 | LOC728285 | similar to keratin associated protein 2-4 |
| NM_002223.2 | ITPR2 | inositol 1,4,5-triphosphate receptor, type 2 |
| NM_002192.2 | INHBA | Caution, this probeset may detect an extended transcript or alternative terminal exon for inhibin, beta A (activin A, activin AB alpha polypeptide) |
| AK000776 | ROR1 | Caution, this probeset may detect an extended transcript or alternative terminal exon for receptor tyrosine kinase-like orphan receptor 1 |
| AU144005 | ITGAV | Caution, this probeset may detect an alternative exon for integrin, alpha V (vitronectin receptor, alpha polypeptide, antigen CD51) |
| NM_000382.2 | ALDH3A2 | aldehyde dehydrogenase 3 family, member A2 |
| NM_020987.2 | ANK3 | ankyrin 3, node of Ranvier (ankyrin G) |
| NM_004058.2 | CAPS | calcyphosine |
| NM_001752.2 | CAT | catalase |
| NM_001875.2 | CPS1 | carbamoyl-phosphate synthetase 1, mitochondrial |
| NM_004390.2 | CTSH | cathepsin H |
| NM_001352.2 | DBP | D site of albumin promoter (albumin D-box) binding protein |
| NM_001005336.1 | DNM1 | dynamin 1 |
| NM_004409.2 | DMPK | dystrophia myotonica-protein kinase |
| NM_001958.2 | EEF1A2 | eukaryotic translation elongation factor 1 alpha 2 |
| NM_001408.1 | CELSR2 | cadherin, EGF LAG seven-pass G-type receptor 2 (flamingo homolog, *Drosophila*) |
| NM_177996.1 | EPB41L1 | erythrocyte membrane protein band 4.1-like 1 |
| NM_005252.2 | FOS | v-fos FBJ murine osteosarcoma viral oncogene homolog |
| NM_002072 | GNAQ | guanine nucleotide binding protein (G protein), q polypeptide |
| NM_002081.1 | GPC1 | glypican 1 |
| NM_005896.2 | IDH1 | isocitrate dehydrogenase 1 (NADP+), soluble |

TABLE A-continued

| GenBank ID | GeneSymbol | Gene description |
|---|---|---|
| NM_002168.2 | IDH2 | isocitrate dehydrogenase 2 (NADP+), mitochondrial |
| NM_021070.2 | LTBP3 | latent transforming growth factor beta binding protein 3 |
| NM_002374.3 | MAP2 | microtubule-associated protein 2 |
| NM_001012333.1 | MDK | midkine (neurite growth-promoting factor 2) |
| NM_000435.1 | NOTCH3 | Notch homolog 3 (*Drosophila*) |
| NM_002585 | PBX1 | pre-B-cell leukemia transcription factor 1 |
| NM_000920 | PC | pyruvate carboxylase |
| NM_005391.1 | PDK3 | pyruvate dehydrogenase kinase, isozyme 3 |
| NM_002705.3 | PPL | periplakin |
| NM_002737.2 | PRKCA | protein kinase C, alpha |
| NM_152880.2 | PTK7 | PTK7 protein tyrosine kinase 7 |
| NM_001038.4 | SCNN1A | sodium channel, nonvoltage-gated 1 alpha |
| NM_003355.2 | UCP2 | uncoupling protein 2 (mitochondrial, proton carrier) |
| NM_003389 | CORO2A | coronin, actin binding protein, 2A |
| NM_003568.1 | ANXA9 | annexin A9 |
| NM_003786.2 | ABCC3 | ATP-binding cassette, sub-family C (CFTR/MRP), member 3 |
| NM_004753.4 | DHRS3 | dehydrogenase/reductase (SDR family) member 3 |
| NM_005117.2 | FGF19 | fibroblast growth factor 19 |
| NM_005759 | ABI-2 | abl-interactor 2 |
| NM_002510 | GPNMB | glycoprotein (transmembrane) nmb |
| NM_006393 | NEBL | nebulette |
| NM_007365 | PADI2 | peptidyl arginine deiminase, type II |
| NM_014988.1 | LIMCH1 | LIM and calponin homology domains 1 |
| NM_015132 | SNX13 | sorting nexin 13 |
| NM_015271.2 | TRIM2 | tripartite motif-containing 2 |
| NM_014467.1 | SRPX2 | sushi-repeat-containing protein, X-linked 2 |
| NM_014067.2 | MACROD1 | MACRO domain containing 1 |
| NM_013296.3 | GPSM2 | G-protein signalling modulator 2 (AGS3-like, *C. elegans*) |
| NM_016619.1 | PLAC8 | placenta-specific 8 |
| NM_016233.1 | PADI3 | peptidyl arginine deiminase, type III |
| AK096661.1 | DKFZP761M1511 | hypothetical protein DKFZP761M1511 |
| NM_019027.1 | RBM47 | RNA binding motif protein 47 |
| AF172820.1 | MXRA6 | matrix-remodelling associated 6 |
| NM_032379.3 | SYTL2 | synaptotagmin-like 2 |
| NM_017734.2 | PALMD | palmdelphin |
| NM_017905.3 | TMCO3 | transmembrane and coiled-coil domains 3 |
| NM_020169.2 | LXN | latexin |
| NM_020397.2 | CAMK1D | calcium/calmodulin-dependent protein kinase ID |
| AB007969.1 | CLMN | calmin (calponin-like, transmembrane) |
| NM_021180.2 | GRHL3 | grainyhead-like 3 (*Drosophila*) |
| NM_022783.1 | DEPDC6 | DEP domain containing 6 |
| NM_024539.3 | RNF128 | ring finger protein 128 |
| NM_024896.2 | KIAA1815 | KIAA1815 |
| NM_025094 | FLJ22184 | hypothetical protein FLJ22184 |
| NM_024491.2 | CEP70 | centrosomal protein 70 kDa |
| NM_024491 | BITE | p10-binding protein |
| NM_030821 | PLA2G12 | phospholipase A2, group XII |
| NM_032042.3 | C5orf21 | chromosome 5 open reading frame 21 |
| NM_032229.2 | SLITRK6 | SLIT and NTRK-like family, member 6 |
| NM_032872.1 | SYTL1 | synaptotagmin-like 1 |
| NM_177963.2 | SYT12 | synaptotagmin XII |
| NM_138393.1 | C19orf32 | chromosome 19 open reading frame 32 |
| NM_080597.2 | OSBPL1A | oxysterol binding protein-like 1A |
| NM_199165.1 | ADSSL1 | adenylosuccinate synthase like 1 |
| NM_138962 | MSI2 | musashi homolog 2 (*Drosophila*) |
| NM_138801 | LOC130589 | aldose 1-epimerase |
| NM_138801.1 | GALM | galactose mutarotase (aldose 1-epimerase) |
| NM_144658.2 | DOCK11 | dedicator of cytokinesis 11 |
| NM_152527.3 | SLC16A14 | solute carrier family 16 (monocarboxylic acid transporters), member 14 |
| NM_170743.2 | IL28RA | interleukin 28 receptor, alpha (interferon, lambda receptor) |
| NM_001012642.1 | GRAMD2 | GRAM domain containing 2 |
| NM_174921.1 | C4orf34 | chromosome 4 open reading frame 34 |
| NM_174921 | LOC201895 | hypothetical protein LOC201895 |
| NM_207362.1 | C2orf55 | chromosome 2 open reading frame 55 |
| NM_174921.1 | C4orf34 | chromosome 4 open reading frame 34 |
| AA732944 | RALGPS2 | Ral GEF with PH domain and SH3 binding motif 2 |
| AU145501 | NAALADL2 | N-acetylated alpha-linked acidic dipeptidase-like 2 |

TABLE A-continued

| GenBank ID | GeneSymbol | Gene description |
|---|---|---|
| NM_006252.3 | PRKAA2 | protein kinase, AMP-activated, alpha 2 catalytic subunit |
| AW294903 | WNT7B | wingless-type MMTV integration site family, member 7B |

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-H. Impact of IKKb-induced NF-kB on tumor rejection. (a) EMSA showing NF-kB nuclear levels in LLC-OVA transduced with control MiG, IKK and MiG treated with TNFa for 1 h and 2 h as indicated. (b) RT-PCR showing KC/CXCL1 expression in LLC-OVA transduced with control MiG, IKK and MiG treated with TNFa for 1 h and 2 h as indicated. Samples run in triplicate and reported as mean+/−SEM. (c) Tumor growth in C57B1/6 mice inoculated s.c. with non-immunogenic LLC-MiG and LLC-IKK over indicated time periods. Each line represents a single mouse. (d) Tumor growth in C57B1/6 mice inoculated s.c. with immunogenic LLC-OVA-MiG and LLC-OVA-IKK over indicated time periods. Each line represents a single mouse. (e) Impact of immunogenic-LLC tumors on peripheral T cells. Tetramer analysis of OVA-specific CD8 T cells in peripheral blood on day 10 from naïve mice or mice receiving LLC-OVA-MiG or LLC-OVA-IKK cells s.c. Each point represents a single mouse. Student's T test was performed to compare tetramer positive CD8 T cells between mice receiving LLC-OVA-MiG and LLC-OVA-IKK tumors. (f) C57B1/6 mice received s.c. LLC-OVA-MiG or LLC-OVA-IKK and tumor growth was monitored. Relative fold increase in tumor volume in mice at D21 post-inoculation compared to D4 post-inoculation. Combined results from 3 independent experiments are shown (n=11 for both groups). Each point represents tumor growth from a single mouse. (g) Tumor growth in RAG2−/− mice inoculated s.c. with LLC-OVA-MiG or LLC-OVA-IKK. Each line represents a single mouse. (h) Tumor growth in L129/sv mice inoculated s.c. with immunogenic LKR-OVA-MiG and LKR-OVA-IKK over indicated time periods. Each line represents a single mouse.

DETAILED DESCRIPTION

Figure 1A:
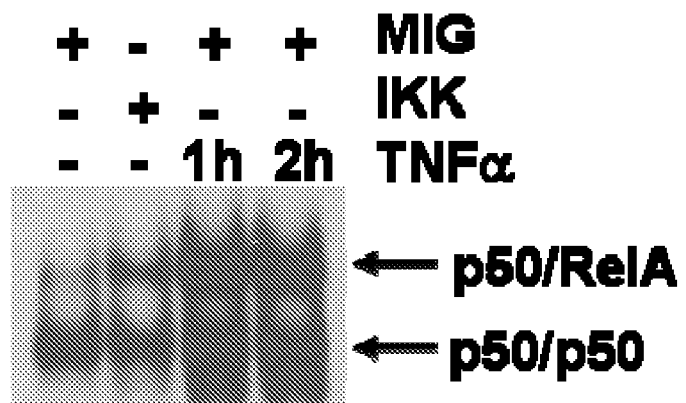

Previously, it was not known whether tumor NF-kB regulates T cell-mediated anti-tumor responses and immune surveillance. Nonetheless, consistent with known pro-tumor functions, it is possible that NF-kB also impairs anti-tumor T cell responses through cancer cell-intrinsic and/or microenvironment effects. However, as shown herein, in immunogenic tumors in mice NF-kB induces T cell-mediated tumor rejection. Enhanced T cell recruitment was found to be a key NF-kB dependent mechanism for tumor rejection. To investigate potential pro-tumor and anti-tumor NF-kB functions in human cancer, a novel human lung cancer NF-kB gene expression signature was developed. Although there was evidence of both inflammatory and immune-response functions, overall NF-kB activity was strongly associated with T cell presence in human lung cancer; as T cell presence in tumors can be associated with immune surveillance and improved patient survival, NF-kB activity as determined by the gene signature described herein is prognostic. These findings in both murine and human lung cancer indicate that a crucial and previously unappreciated function of tumor NF-kB is to promote T cell-mediated immune surveillance responses; thus, the NF-kB gene signature can be used to select subjects for treatment with immunotherapy.

As described herein, identification of genes that are regulated by NF-kB specifically in lung cancer cells provide an indicator of NF-kB activation state. Such an NF-kB signature can then be used to predict disease outcome and survival, and validate this pathway as a potentially crucial therapeutic target in human lung cancer. To this end, an NF-kB signature was established in lung cancer cell lines and the correlation between NF-kB activation state and disease outcome and patient survival was determined using the Consortium for the Molecular Classification of Lung Adenocarcinoma (CM-CLA) survival prediction study (Shedden et al. 2008. Nat Med 14:822-827).

Methods of Treating, Assigning a Prognosis or Predicting Survival

The methods can be used to monitor a treatment (e.g., an immunotherapy or administration of an NF-kB inhibitor), or to select a treatment, e.g., to select a treatment regime including an immunotherapy or administration of an NF-kB inhibitor for a subject. In addition, the methods described herein can be used for, e.g., to assist in, assigning a prognosis or predicting survival in a subject who has a tumor, e.g., a solid tumor.

As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. In general, the methods described herein can be practiced on subjects with solid tumors.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, cancers evaluated by the methods described herein include those that are particularly immunogenic, e.g., neuroblastoma, melanoma, and renal cell cancer.

In some embodiments, cancers or tumors evaluated by the methods described herein include carcinomas (i.e., epithelial cancers), such as a lung cancer (e.g., non-small-cell lung cancer (NSCLC)), breast cancer, colorectal cancer, head and neck cancer, or ovarian cancer. Epithelial malignancies are cancers that affect epithelial tissues, and include adenocarcinomas and squamous cell carcinoma. In some embodiments, the methods can be used to evaluate or treat adenocarcinomas.

The present methods can include the use of some or all of the genes shown in Table A or Table 1, e.g., 10, 20, 30, 40, 50, 60, 70, 80, 90, 100, 110, 120, 130, 138, 140, 150, 160, 170, 180, 190, or more of the genes in Table 1, e.g., the genes shown in Table 2 or 3, or more preferably the genes in the ten-gene signature (i.e., GBP1, PSMB9, IRF1, TAP1, TNFAIP3, CCL5, PSMB8, IL32, SH2B3, and NFKBIE), to predict NF-kB transcriptional activity in different tumor types, predict outcome in subjects with tumors, and select treatments for subjects with tumors. This can be done using methods known in the art, e.g., using a classifier based on principal component analysis (PCA), e.g., as described below; by a classifier based on weighted majority voting; or classifiers based on multi-dimensional scaling of the full 240 genes or a sub-set of the genes described in this application or in U.S. Ser. No. 61/554,314 (Shedden et al., 2008. Nat Med 14:822-827; Chen et al., 2010. Breast Cancer Res Treat 119: 335-346). Those tumors found to have high levels of NF-kB activity can then be selected for treatment, e.g., with an NF-kB inhibitor, and NF-kB activator, and/or with immunotherapy. Depending on levels of NF-kB activity (high or low), subjects can be selected can be selected for treatment, e.g., with an NF-kB inhibitor or with immunotherapy (with high NF-kB activity) or compounds capable of enhancing NF-kB to enhance effect of immunotherapy (with low NF-kB activity).

Further, five inflammatory genes (CXCL1, CXCL3, IL6, and IL8) have been identified that predict poor outcome (see FIGS. 6A-D). These genes are thought to mediate inflammatory as well as tumor invasion and metastasis responses. The methods can include identifying subjects having tumors with high levels of expression of those genes, and treating them with NF-kB pathway inhibitors.

Additional NF-kB signature genes have been identified (CCL2, ICAM-1, LTB, and CD83) predict improved survival (see FIGS. 7A-D). High expression of these genes is expected to be associated with improved response to cancer immunotherapy treatment, thus, the methods can include identifying subjects having tumors with high levels of expression of those genes, and treating them with immunotherapy.

Finally, as demonstrated herein, LTB individually predicts improved outcome (FIG. 7B) and the presence of T cells in tumors. LTB induces expression of T cell chemokines such as CCL2 and CCL5 in lung cancer cells. High expression of LTB is expected to be associated with improved response to cancer immunotherapy treatment. Thus, the methods can include identifying subjects having tumors with high levels of expression of LTB, and treating them with immunotherapy.

The methods described herein generally include obtaining a sample from a subject, and evaluating the presence and/or level of an NF-kB signature gene in the sample, and comparing the presence and/or level with one or more references, e.g., a control reference that represents a normal level of the NF-kB signature gene, e.g., a level in an unaffected subject, a level in a normal, non-tumor tissue of the subject (e.g., normal lung tissues) and/or a disease reference that represents a level associated with outcome or survival. The methods can include detecting the level of a gene as described herein, or a protein encoded by a gene described herein. The presence and/or level of a gene or protein can be evaluated using methods known in the art, e.g., using quantitative PCR methods or molecular barcoding technologies, e.g., NanoString™ (see, e.g., U.S. Pat. No. 7,919,237; U.S. Pat. No. 7,473,767; and Geiss et al., Nature Biotechnology 26: 317-25 (2008)). In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of an NF-kB signature gene or gene product.

In some embodiments, the methods include assaying levels of one or more control genes or proteins, and comparing the level of expression of the immune-related genes or proteins to the level of the control genes or proteins, to normalize the levels of the immune-related genes or proteins. Suitable endogenous control genes includes a gene whose expression level should not differ between samples, such as a housekeeping or maintenance gene, e.g., 18S ribosomal RNA; beta Actin; Glyceraldehyde-3-phosphate dehydrogenase; Phosphoglycerate kinase 1; Peptidylprolyl isomerase A (cyclophilin A); Ribosomal protein L13a; large Ribosomal protein P0; Beta-2-microglobulin; Tyrosine 3-monooxygenase/tryptophan 5-monooxygenase activation protein, zeta polypeptide; Succinate dehydrogenase; Transferrin receptor (p90, CD71); Aminolevulinate, delta-, synthase 1; Glucuronidase, beta; Hydroxymethyl-bilane synthase; Hypoxanthine phosphoribosyltransferase 1; TATA box binding protein; and/or Tubulin, beta polypeptide.

Generally speaking, the methods described herein can be performed on cells from a tumor, e.g., a benign or malignant tumor. The cells can be obtained by known methods, e.g., during a biopsy (such as a core needle biopsy), or during a surgical procedure to remove all or part of the tumor. The cells can be used fresh, frozen, fixed, and/or preserved, so long as the mRNA or protein that is to be assayed is maintained in a sufficiently intact state to allow accurate analysis.

In some embodiments of the methods described herein, the levels of the immune-related genes in the tumor sample can be compared individually to levels in a reference. The reference levels can represent levels in a subject who has a good outcome, a good prognosis, or a long predicted survival time (e.g., 2 years or more). Alternatively, reference levels can represent levels in a subject who has a poor prognosis, or a shorter predicted survival time (e.g., less than 2 years). In some embodiments, the reference levels represent a threshold, and a level in the tumor that is above the threshold reference level indicates that the subject has a good outcome, a good prognosis, or a long predicted survival time (e.g., 2 years or more), and levels below the threshold reference level indicates that the subject has a poor outcome, a poor prognosis, or a shorter predicted survival time (e.g., less than 2 years).

In some embodiments, the reference levels can represent levels in a subject who is predicted to respond to immunotherapy. Alternatively, reference levels can represent levels in a subject who is predicted to have no or a poor response to immunotherapy. In some embodiments, the reference levels represent a threshold, and a level in the tumor that is above the threshold reference level indicates that the subject is predicted to respond to immunotherapy, and levels below the threshold reference level indicates that the subject is predicted to have no or poor response to immunotherapy. In subjects who are predicted respond to immunotherapy, the methods can further include administering an immunotherapy for those subjects, or selecting or recommending a treatment including an immunotherapy for those subjects.

In some embodiments of the methods described herein, values representing the levels of the NF-kB genes (or subsets thereof, e.g., as described herein) can be summed to produce a "NF-kB gene score" that can be compared to a reference NF-kB gene score, wherein an NF-kB gene score that is above the reference NF-kB gene score indicates that the subject has a long predicted survival time (e.g., 2 years or more) or is predicted to have a positive response to immunotherapy, and an NF-kB gene score below the reference score indicates that the subject has a shorter predicted survival time (e.g., less than 2 years), or is predicted to have no or a poor response to immunotherapy. In subjects with an NF-kB gene score below the reference score, an NF-kB activator can be administered in conjunction with immunotherapy.

For example, in some embodiments, the expression levels of each of the evaluated genes can be assigned a value (e.g., a value that represents the expression level of the gene, e.g., normalized to an endogenous control gene as described herein). That value (optionally weighted to increase or decrease its effect on the final score) can be summed to produce an immune-related gene score. One of skill in the art could optimize such a method to determine an optimal algorithm for determining an NF-kB gene score.

One of skill in the art will appreciate that references can be determined using known epidemiological and statistical methods, e.g., by determining an NF-kB gene score, or NF-kB gene-encoded protein or mRNA levels, in tumors from an appropriate cohort of subjects, e.g., subjects with the same type of cancer as the test subject and a known prognosis (e.g., good or poor), immunotherapy outcome, or predicted survival time (e.g., less than 2 years, or 2 years or more).

In some embodiments, the methods can be used to monitor the efficacy of a treatment, e.g., an immunotherapy plus an NF-kB activator. The methods include determining levels of the NF-kB genes in a sample, then administering one or more doses of the treatment, then determining levels of the NF-kB genes to determine whether the treatment has increase immune infiltration of the tumor. An increase in NF-kB gene levels (or immune-related gene score, if calculated) indicates that the treatment was effective.

Immunotherapy

T cell presence in tumors is typically associated with immune surveillance and improved patient survival (Zhang et al. 2003. The New England Journal of Medicine 348:203-213; Fridman et al., 2011. Cancer research 71:5601-5605; Pages et al. 2005. The New England journal of medicine 353:2654-2666; Yu et al., 2009. Nature reviews. Cancer 9:798-809; Yu et al., 2007. Nature Reviews. Immunology 7:41-51; Schreiber et al., 2011. Science 331:1565-1570; Vesely et al., 2011. Annual Review of Immunology 29:235-271). Consequently, immunotherapy using blockade of negative regulators of T cells function is an especially attractive approach (Hodi et al., The New England journal of medicine 2010 363:711-723; Topalian et al., 2012. The New England Journal of Medicine 366:2443-2454). Unlike genetic lesion-specific therapies, immunotherapy has potential for targeting tumors irrespective of driver oncogene mutation status. Thus in some embodiments, the methods include administering an immunotherapy to the subject, e.g., one or more therapies that promote anti-cancer immunity, including administering one or more of: dendritic cells or peptides with adjuvant, immune checkpoint inhibitors, DNA-based vaccines, cytokines (e.g., IL-2), cyclophosphamide, agonists of OX40 (OX40; CD134), anti-interleukin-2R immunotoxins, and/or antibodies such as anti-CD137, anti-PD1, or anti-CTLA-4; see, e.g., Kruger et al., Histol Histopathol. 2007 June; 22(6):687-96; Eggermont et al., Semin Oncol. 2010 October; 37(5):455-9; Klinke D J 2nd, Mol Cancer. 2010 Sep. 15; 9:242; Alexandrescu et al., J Immunother. 2010 July-August; 33(6):570-90; Moschella et al., Ann NY Acad Sci. 2010 April; 1194:169-78; Ganesan and Bakhshi, Natl Med J India. 2010 January-February; 23(1):21-7; Golovina and Vonderheide, Cancer J. 2010 July-August;

16(4):342-7; Hodi et al., The New England journal of medicine 2010 363:711-723; Pentcheva-Hoang et al., Immunological Reviews 2009 229:67-87; Brahmer et al., Journal of Clinical Oncology 2010 28:3167-3175; Lynch et al., Journal of Clinical Oncology 2012 30(17):2046; Weber, Current Opinion in Oncology 2011 23:163-169; Weber, Seminars in Oncology 2010 37:430-439; Topalian et al., 2012. The New England Journal of Medicine 366:2443-2454; and Higano et al., Cancer 2009 115:3670-3679. In some embodiments, the methods include administering a composition comprising tumor-pulsed dendritic cells, e.g., as described in WO2009/114547 and references cited therein. Additional examples of immunotherapies include virus-based anti-cancer vaccines (e.g., adenovirus), formulations of Toll-like Receptor or RIG-I-like receptor ligands, Adoptive T cell therapy or other cell types. In some embodiments the immunotherapy is selected from the group consisting of BiovaxID (an autologous vaccine containing tumor-specific idiotype proteins from individual patient's lymphoma cells conjugated to keyhole limpet hemocyanin (KLH)); Provenge sipuleucel-T (an FDA-approved example of the use of autologous dendritic cells); Yervoy (a mAb against CTLA-4 (CD152), approved in 2011 for metastatic melanoma); tremelimumab (formerly ticilimumab, an anti-CTLA-4 mAb); IMA901 (a vaccine containing 10 tumor-associated peptides (TUMAPs)), alone or in combination with Sutent (a small molecule VEGF receptor tyrosine kinase inhibitor); GV1001 (a peptide vaccine with the sequence of human telomerase reverse transcriptase (hTERT), from Kael-Gemvax); Lucanix belagenpumatecel-L (four NSCLC cell lines carrying antisense oligonucleotides against transforming growth factor beta 2 (TGFB2)); Stimuvax (a liposomal vaccine containing a synthetic 25-amino acid peptide sequence from mucin 1 (MUC1; CD227)); Allovectin velimogene aliplasmid (a DNA plasmid encoding major histocompatibility complex (MHC) class I B7 (HLA-B7) complexed with lipid); BMS-936558 (ONO-4538) (a human mAb against PD-1); BMS-936559 (formerly MDX-1105) (a human mAb against PD-L1); Zelboraf (vemurafenib, an oral small molecule inhibitor of the oncogenic BRAF V600E mutation); Votrient (pazopanib, a small molecule VEGF receptor tyrosine kinase inhibitor); ISF35 or Lucatumumab (HCD122) (mAbs against CD40); GVAX (an allogeneic cancer vaccine engineered to secrete granulocyte macrophage-colony stimulating factor (GM-CSF)). See, e.g., Flanagan, "Immune Springboard," Biocentury, Jun. 18, 2012 A5-A10 (2012), available at biocentury.com. In some embodiments, the immunotherapy comprises administration of an agent that effects CTLA4 blockade (e.g., Ipilumumab BMS), PD1-blockade (e.g., BMS-936558, BMS; CT-011, Curetech; MK-3475, Merck), CD137 activation (e.g., BMS-663513, BMS), PD-L1 blockade (e.g., BMS-936559, BMS), CD40 activation (e.g., CP-870893, Pfizer) and autologous dendritic cells (e.g., Provenge).

NF-kB Inhibitors

In some embodiments, the methods include administering a therapy comprising an NF-kB inhibitor, i.e., a compound that inhibits the Nuclear Factor kappa B (NF-kB) intracellular transcription factor, to a subject who has a high level of NF-kB activity. Exemplary NF-kB inhibitors include sulfasalazine, Luteolin, rapamycin or derivatives (e.g., temsirolimus and everolimus), caffeic acid phenethylester, SN50 (a cell-permeable inhibitory peptide), parthenolide, triptolide, wedelolactone, lactacystin, substituted resorcinols, (E)-3-(4-methylphenylsulfonyl)-2-propenenitrile (e.g., Bay 11-7082, Bay 11-7821, or Bay 11-7085, Sigma-Aldrich, St. Louis, Mo.), Pranlukast, etoposide, bortezomib, MLN9708 (Kupperman et al., MLN9708), PS-1145 (Millennium Pharmaceuticals), tetrahydrocurcuminoids (such as Tetrahydrocurcuminoid CG, available from Sabinsa Corporation of Piscataway, N.J.), extracts of *Paulownia tomentosa* wood, and MG-132 [Z-Leu-Leu-Leu-H]. See, e.g. U.S. Pat. No. 7,838,513. Inhibitory nucleic acids targeting NF-kB, e.g., siRNA, antisense, or locked nucleic acids, can also be used. Hsp90 inhibitors such as 17-DMAG, AUY-922 and IPI-504 can also be used to inhibit NF-kB activation. See, e.g., US20070110828.

NF-kB Activators

In some embodiments, the methods include administering a therapy comprising an NF-kB activator, i.e., a compound that enhances activity of the Nuclear Factor kappa B (NF-kB) intracellular transcription factor, to a subject who has a low level of NF-kB activity, to enhance the anti-tumor immune response, e.g., in combination with immunotherapy. Exemplary NF-kB activators include cytotoxic anticancer agents such as taxanes (e.g., paclitaxel), vinca alkaloids (e.g., vinrelobine, vinblastine, vindesine, and vincristine), anthracyclines (e.g., daunorubicin, doxorubicin, mitoxantraone, and bisanthrene), epipodophyllotoxins (e.g., etoposide, etoposide orthoquinone, and teniposide); histone deacetylase inhibitors (e.g., romidepsin); pemetrexed; and topoisomerase inhibitors. See, e.g., Das and White, 1997. The Journal of Biological Chemistry, 272, 14914-14920; Nakanishi and Toi, Nat Rev Cancer. 2005 April; 5(4):297-309; Ganapathi et al., Curr Pharm Des. 2002; 8(22):1945-58; see also Goodman and Gilman's The Pharmacological Basis of Therapeutics, e.g., 1277-1290 (7th ed. 1985) for descriptions and exemplary compounds.

EXAMPLES

The invention is further described in the following examples, which do not limit the scope of the invention described in the claims.

Example 1

Critical Role of NF-kB in Immunogenic Tumor Rejection in Mice

The presence of tumor infiltrating T cells, which likely recognize tumor expressed antigens, is associated with improved patient survival (Zhang et al. 2003. The New England Journal of Medicine 348:203-213; Fridman 2011. Cancer Research 71:5601-5605; Pages et al., 2005. The New England Journal of Medicine 353:2654-2666). To induce de novo anti-tumor T cell responses in mice, Kb-OVA (a single polypeptide encoding H-2K$^b$, β$_2$-M and the ovalbumin SIINFEKL peptide recognized by CD8 T cells)(Wang et al., 2009. Science 326:871-874) was expressed in poorly immunogenic Lewis lung carcinoma (LLC) to generate LLC-OVA.

The LLC cells were cultured in DMEM supplemented with 10% fetal bovine serum (FBS). Retroviruses were prepared by transfecting HEK 293T cells with Kb-OVA and packaging vectors as previously described (Valenzuela et al., 2009. J Clin Invest 119:3774-3786). Retrovirus transduced cells were sorted based on GFP expression using a FACS Vantage sorter (BD Biosciences, San Jose, Calif.) (Wang et al., 2007. J Immunol 178:6777-6788). Retrovirus infected LLC and human cell-lines were sorted based on GFP expression to yield >95% purity. Tetramer staining was performed as described (Cho and Celis, 2009. Cancer research 69:9012-9019) with the following changes: cells were incubated for 5 minutes at RT with Fc block and DAPI was added to cells prior to analysis for viability gating. Her/Neu tetramer has been described (Nava-Parada et al., 2007. Cancer research 67:1326-1334) and H2-Kb OVA tetramer was purchased from Beckman Coulter (Brea, Calif.). Flow cytometric analysis was performed on an LSR II cytometer (BD Biosciences, San Jose, Calif.). Aggregates and dead cells were excluded from analysis. Data were acquired using CellQuest software (BD Biosciences, San Jose, Calif.) and analyzed using FlowJo software (Tree Star, Ashland, Oreg.).

Cells were harvested in logarithmic growth after being cultured for less than two weeks and washed once in injection medium (phenol-free DMEM supplemented with 2% FBS) and counted. $5 \times 10^5$ LLC cells were injected either s.c. (in a volume of 100 ul) or i.v. (in a volume of 200 ul). Subcutaneous tumors were monitored for growth and measured 2-3 times per week. Mice receiving intravenous LLC injections were monitored for morbidity. Mice were sacrificed when s.c. tumors reached a diameter of 20 mm or when they showed signs of morbidity (i.v. or s.c.). Tumor volume was calculated as previously described (Torabian et al. 2009. The American Journal of Pathology 174:1009-1016). Relative tumor growth between treatment groups was analyzed using the Student's T test with Welch's correction. Mice were maintained under specific pathogen free conditions.

Figure 1B:
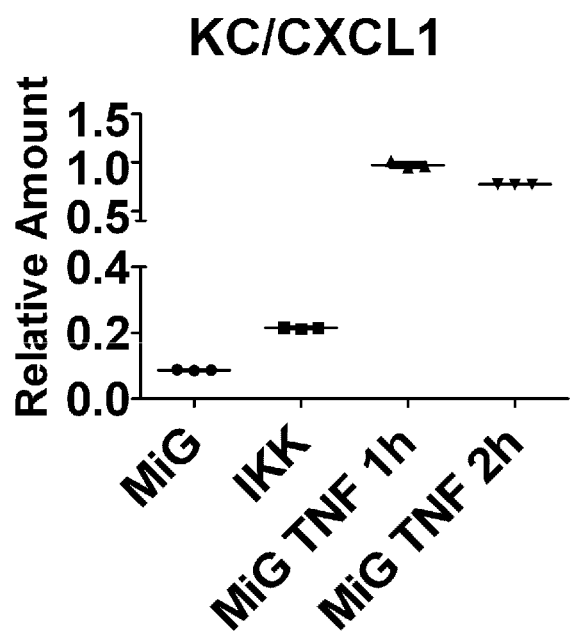
Figure 1C:
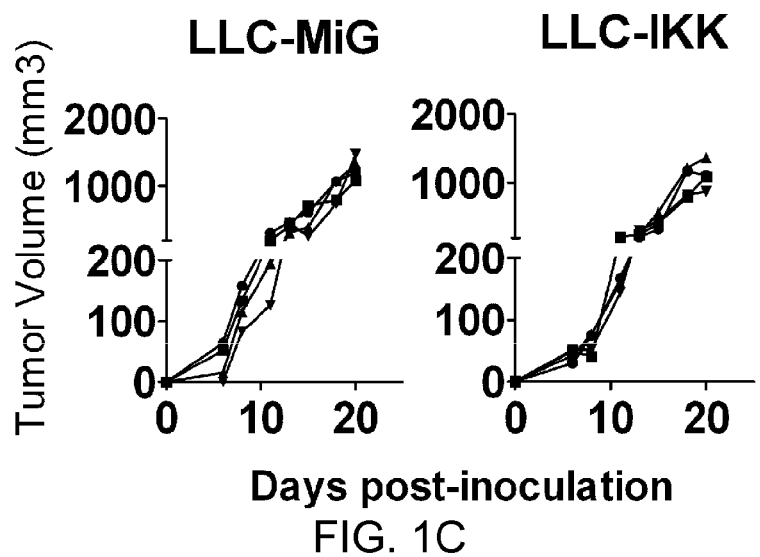
Figure 1D:
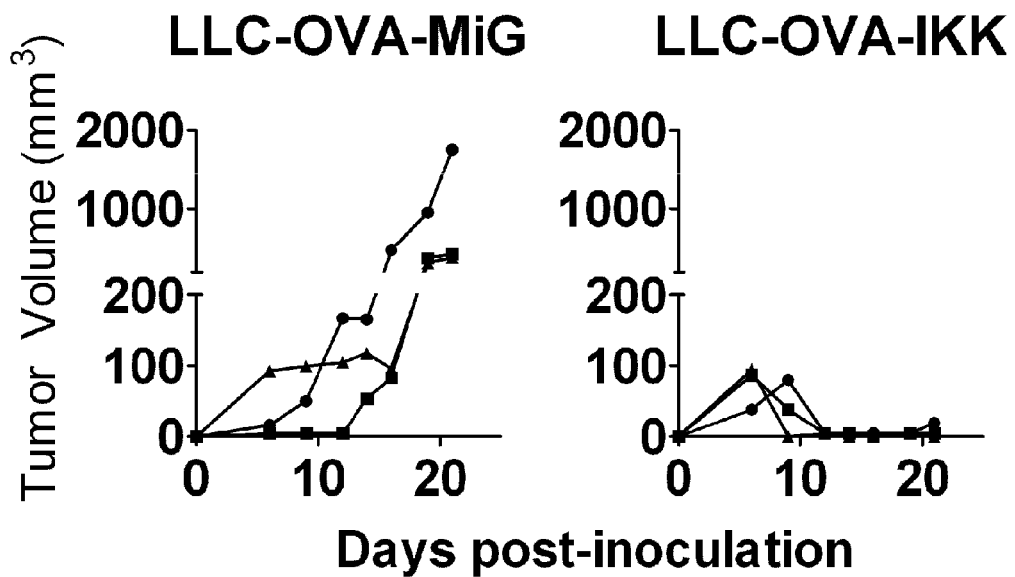
Figure 1H:
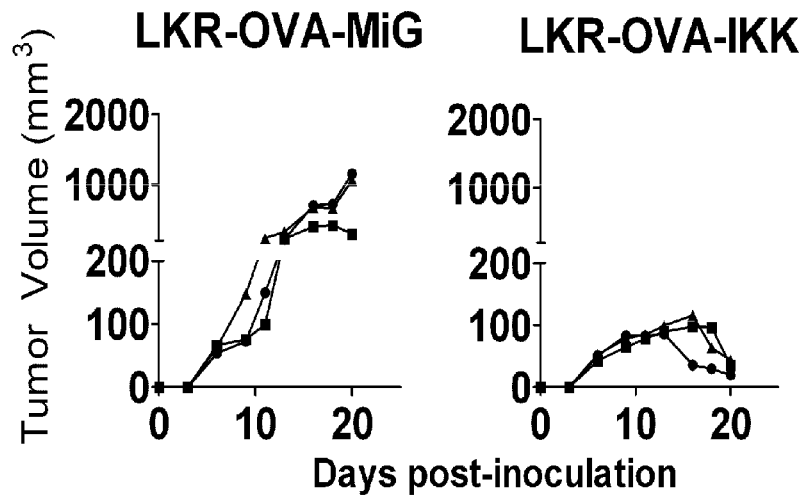
Figure 1I:
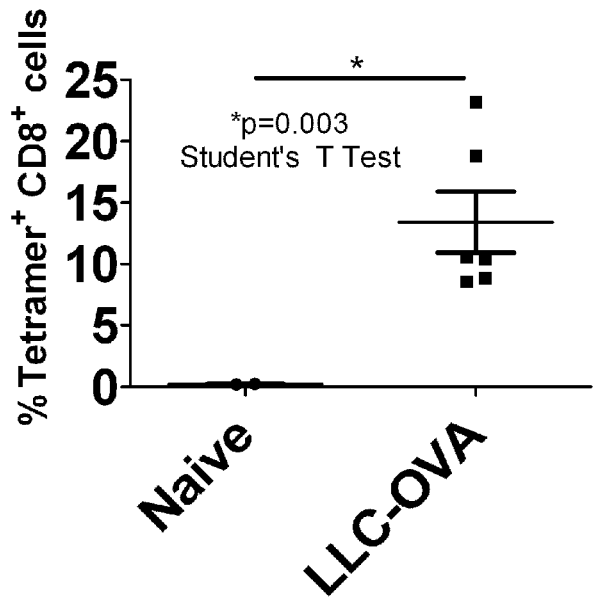
FIG. 1I. Impact of immunogenic-LLC tumors (LLC-OVA) on peripheral OVA-specific CD8 T cells. Tetramer analysis showing percent OVA-specific CD8 T cells in peripheral blood (out of total CD8 T cells) on day 10 from mice receiving LLC-OVA s.c or naïve mice as indicated. Each point represents a single mouse. Student's T test was performed to compare tetramer positive CD8 T cells between naive mice and those receiving LLC-OVA tumors.

Subcutaneous (s.c.) inoculation with LLC-OVA was sufficient to induce an OVA-specific CD8 T cell response (FIG. 1I).

The next experiments determined how tumor NF-kB activity impacts anti-tumor CD8 T cell responses. To selectively activate NF-kB in tumor cells, tumor cell-specific expression of constitutively-activated (CA)-IKKβ was utilized. IKKβ mediates NF-kB activation in response to multiple stimuli and pathways, including those activated by oncogenes such as KRAS (Basseres et al., 2010. Cancer Res 70:3537-3546). Furthermore, IKKβ is potentially amplified in human cancer (Beroukhim et al., 2010. Nature 463:899-905). Retroviruses were prepared by transfecting HEK 293T cells with MiG or activated IKKβ (S177, S181 to E mutations; IKKβEE) and packaging vectors as previously described (Valenzuela et al., 2009. J Clin Invest 119:3774-3786; Wang et al., 2007. J Immunol 178:6777-6788).

Figure 1J:
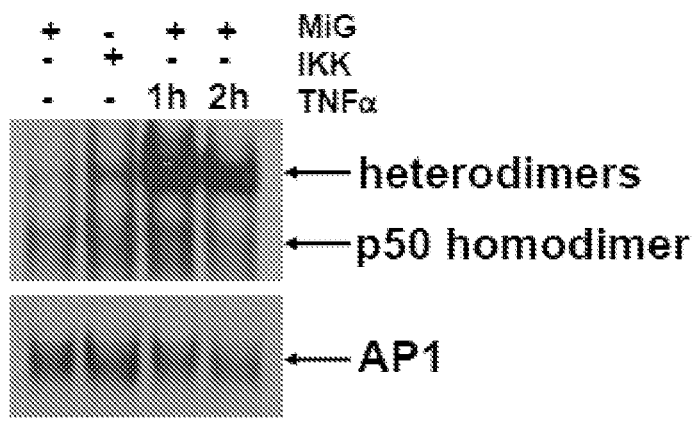
FIG. 1J. Activation of NF-kB in non-immunogenic LLC cells. EMSA showing nuclear levels of NF-kB (top) and AP1 (bottom) in LLC-MiG, LLC-IKK, or LLC-MiG cells treated with TNFα. Results are representative of at least two independent experiments.
Figure 1K:
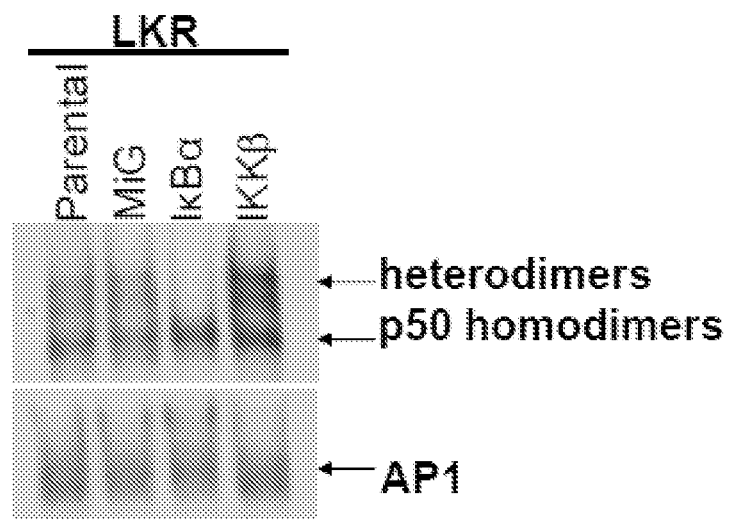
FIG. 1K. NF-kB and AP1 activity as determined by EMSA in parental LKR-13, LKR-13 transduced with the control MiG retrovirus (MiG), IkBαSR retrovirus (IkBα) and CA-IKKβ retrovirus (IKKβ). Mobility of different complexes is indicated with arrows.

CA-IKKβ expression in LLC (LLC-IKK) led to increased NF-kB, but not AP-1, nuclear translocation (FIG. 1J). Similarly, CA-IKKβ expression in LLC-OVA (LLC-OVA-IKK) enhanced nuclear NF-kB, comprising primarily of RelA/p65-containing complexes, and target gene CXCL1/KC expression (FIGS. 1A-B). However, both were induced substantially less compared to TNFα treatment (FIGS. 1A-B). Therefore, CA-IKKβ induces modest activation of NF-kB relative to TNFα.

Compared to control LLC-MiG, LLC-IKK had no significant effect on s.c. growth of non-immunogenic LLC in syngeneic C57BL/6 mice (FIG. 1C). Interestingly, LLC-OVA-IKK tumors initially grew but were subsequently rejected while LLC-OVA-MiG grew unrestrained (FIG. 1D). Importantly, a similar number of activated OVA-specific CD8 T cells were detected in peripheral blood of LLC-OVA-MiG and LLC-OVA-IKK mice (FIG. 1E) suggesting that reduced growth of LLC-OVA-IKK was not due to impaired T cell priming Combined results from 3 experiments indicated that once tumors were perceptible (day 4), 10/11 LLC-OVA-MiG showed 2-fold or greater tumor growth while only 3/11 LLC-OVA-IKK showed similar growth (FIG. 1F). The difference in tumor numbers showing growth in the two groups was significant (p=0.008, Fisher's Exact Test). Importantly, LLC-OVA-IKK grew robustly in Rag2-/- mice (FIG. 1G), demonstrating a role for lymphocytes in rejection of LLC-OVA-IKK.

To extend these studies to a different lung tumor model, KRAS mutant LKR-13 cells (DuPage et al., 2011. Cancer cell 19:72-85) were used. As in LLC, CA-IKKβ expression in LKR-13 also resulted in NF-kB activation (FIG. 1L). Importantly, while LKR-OVA-MiG showed robust growth, LKR-OVA-IKK tumor growth was drastically reduced (FIG. 1H). These results therefore indicate that NF-kB activation induces rejection and/or growth suppression of immunogenic lung tumors in mice.

Figure 2A:
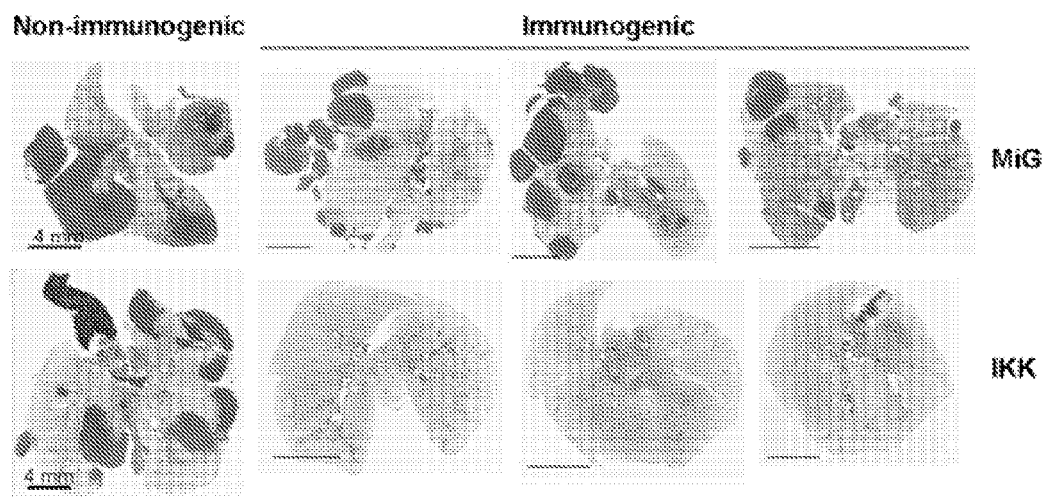
FIGS. 2A-B. NF-kB enhances tumor rejection in vaccine-activated T cell models. (a) Growth of LLC in a metastatic model of lung cancer. H&E staining of lungs from mice 24 days after receiving i.v. non-immunogenic LLC-MiG or LLC-IKK, or immunogenic LLC-OVA-MiG or LLC-OVA-IKK. All scale bars represent 4 mm. (b) C57B1/6-BALB/c F1 (CB6) mice received s.c. TUBO-MiG or TUBO-IKK. After 5 days, half of the mice in each group received HER2 TriVax and tumor growth was monitored. Tumor growth of all mice was calculated at D21 relative to D5 and relative growth in vaccinated mice was compared to their unvaccinated counterparts. p-value calculated using Student's T test with Welch's correction. Graph shows combined results of 2 independent experiments, each point represents tumor growth from a single mouse.

The next experiments used a metastatic model in which i.v. injected LLC form tumor foci in lungs. Importantly, LLC-OVA-IKK showed virtually no tumor foci compared to LLC-OVA-MiG, while both non-immunogenic LLC-MiG and LLC-IKK showing multiple foci (FIG. 2A). While few tumor cells were evident in lungs of LLC-OVA-IKK, multiple lymphoid aggregates were detected.

The effect of NF-kB activation was then determined in vaccine-induced responses against the breast carcinoma TUBO line, which expresses HER2/neu (Lee et al., 2010. Cancer immunology, immunotherapy: CII 59:1073-1081). Turin-Bologna (TUBO) cell-lines were cultured in DMEM supplemented with 10% fetal bovine serum (FBS), and transduced with the vectors as described above. TUBO-MiG and TUBO-IKK injected mice were randomly split into control (no vaccine) and TriVax (Assudani et al., 2008. Cancer Res. 68:9892-9899; Cho and Celis. 2009. Cancer Res. 69:9012-9019) vaccine groups, which were immunized using a synthetic peptide from HER2/neu (Nava-Parada et al., 2007. Cancer Res. 67:1326-1334). Mice receiving TUBO cells were split into TriVax treatment and non-treatment groups on day 5 Immunization with HER2 TriVax was performed as described (Nava-Parada et al., 2007. Cancer Res. 67:1326-1334).

Figure 2B:
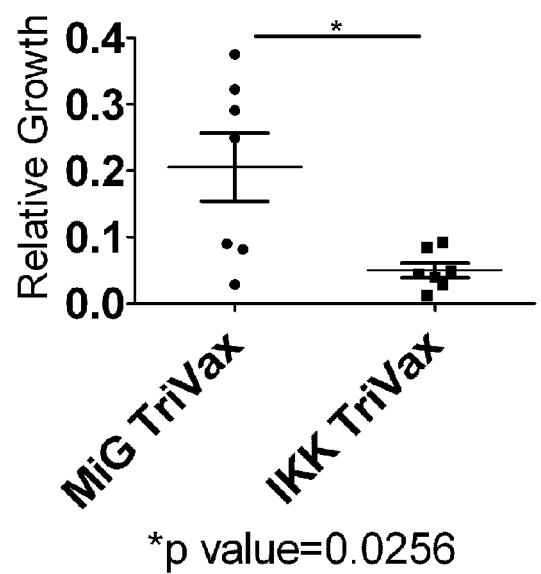
Figure 2C:
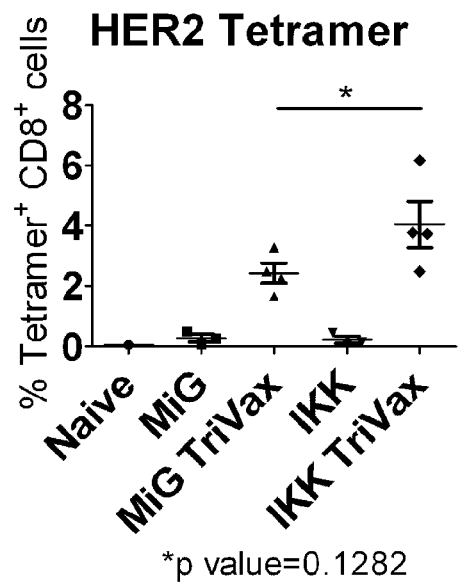
FIG. 2C. Presence of HER2-specific CD8 T cells after TriVax administration. Tetramer analysis of peripheral blood on day 10 from naïve mice or mice receiving TUBO-MiG or TUBO-IKK with or without TriVax vaccination. Vaccination given on day 5. Each point represents data from a single mouse. Results are representative of two independent experiments. Student's T test was performed to compare tetramer positive CD8 T cells between TriVax treated mice receiving TUBO-MiG and those receiving TUBO-IKK tumors.

TriVax-induced HER2-specific T cell increase in peripheral blood was similar in the two groups (FIG. 2C). Tumor growth of vaccinated TUBO-MiG and TUBO-IKK was then determined relative to their unvaccinated counterparts. While vaccination reduced growth of both TUBO-MiG and TUBO-IKK tumors, the reduction was significantly more pronounced in TUBO-IKK tumors (p=0.025) (FIG. 2B). Thus, NF-kB activation restrains tumor growth in de novo and vaccine-induced T cell models.

Example 2

NF-kB Induced T Cell Chemokine Expression is Crucial for Tumor Rejection

Figure 3A:
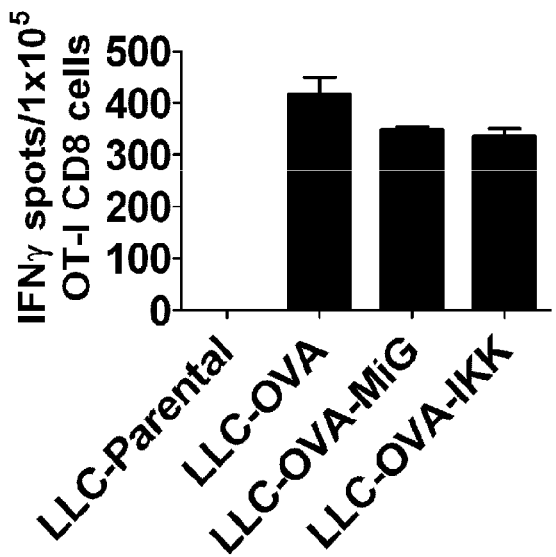
FIGS. 3A-D. Impact of T cell chemokines on tumor rejection. (a) IFNg production by OT-1 CD8 T cells. ELISpot of OT-I T cells cultured with LLC-parental, LLC-OVA, LLC-OVA-MiG, or LLC-OVA-IKK tumor cells. 1×105 LLC targets/well. 1×105 T cells/well. Samples were run in triplicate with results reported as mean+/−SEM. (b) Affymetrix probe set signal intensity of indicated chemokines in LLC-OVA-IKK compared to LLC-OVA-MiG. Genes identified in two separate microarray experiments are shown, and reported as mean+/−SEM. (c) RT-PCR showing CCL2 and CCL5 expression in LLC parental, LLC transduced with OVA and LLC transduced with OVA+MiG or OVA+IKK. Samples were run in triplicate and reported as average+/−SEM. (d) LLC-OVA-IKK-Lenti control and LLC-OVA-IKK-CCL2 KD cells were injected s.c. in C57B1/6 mice and tumor growth was monitored. Each line represents tumor growth in a single mouse. All results are representative of at least two independent experiments.

Possible mechanisms involved in rejection of LLC-OVA-IKK tumors were investigated. Rejection was not likely mediated by increased numbers of OVA-specific CD8 T cells (FIG. 1E). In addition, LLC-OVA-IKK cells were not superior stimulators of CD8 T cell IFNγ expression (FIG. 3A). Importantly, while LLC-OVA-MiG tumors had a small number of infiltrating CD8 T cells, LLC-OVA-IKK tumors showed greatly increased CD8 T cell presence. These results suggested that NF-kB regulated expression of T cell chemokines may be responsible for increased T cell recruitment.

To identify T cell chemokines involved, global RNA expression studies using microarray analysis was performed on LLC-OVA-MiG and LLC-OVA-IKK. RNA was isolated using a Qiagen RNeasy kit, then reverse-transcribed and subjected to quantitative PCR analysis as described (Wang et al., 2007. J Immunol 178:6770-6776) in an Applied Biosystems 7900HT Sequence Detection System (Carlsbad, Calif.) with SYBR Green I Master Mix (Applied Biosystems, Carlsbad, Calif.) using gene-specific primers. All samples were run in triplicate and were normalized to rRNA 18s or β-actin. Primers were obtained from RealTimePrimers.com. For microarray analysis the mRNA in 100 ng of total RNA was specifically converted to cDNA and then amplified and labeled with biotin using the Ambion Message Amp Premier RNA Amplification Kit (Life Technologies, Grand Island, N.Y.) following the manufacturer's protocol. Affymetrix Mouse Genome 430 2.0 Arrays were used in these studies. Hybridization with the biotin-labeled RNA, staining, and scanning of the arrays following the prescribed procedure outlined in the Affymetrix technical manual. Results were analyzed using the MAS 5.0 algorithm. Genes were considered changed if they were identified as changed in the MAS 5.0 comparison analysis and there was a 2-fold difference in signal compared to the control condition.

Figure 3B:
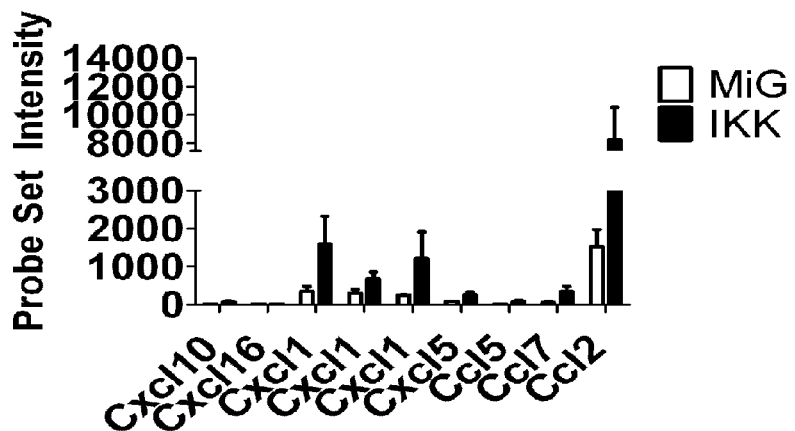
Figure 3C:
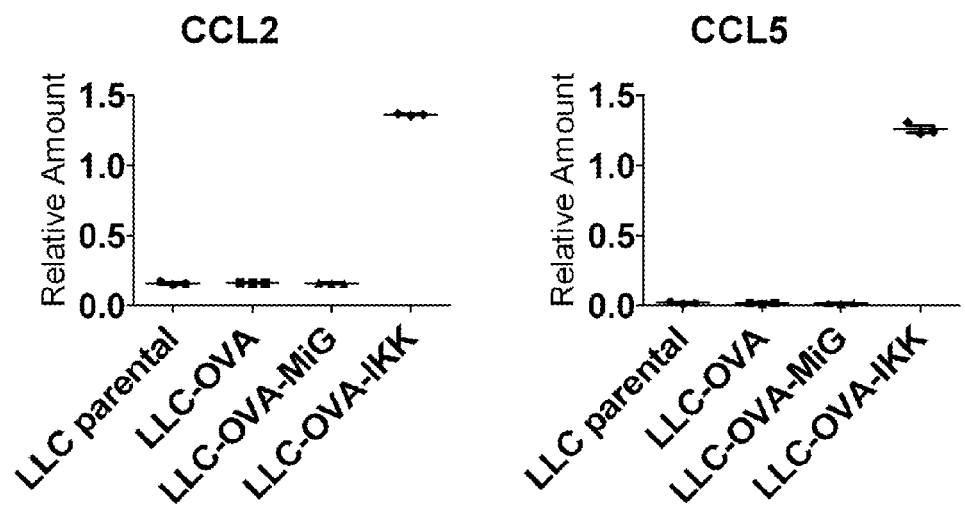
Figure 3D:
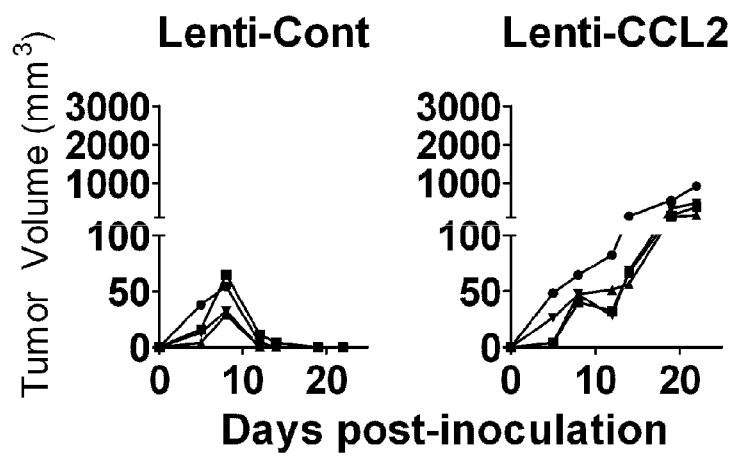
Figure 3E:
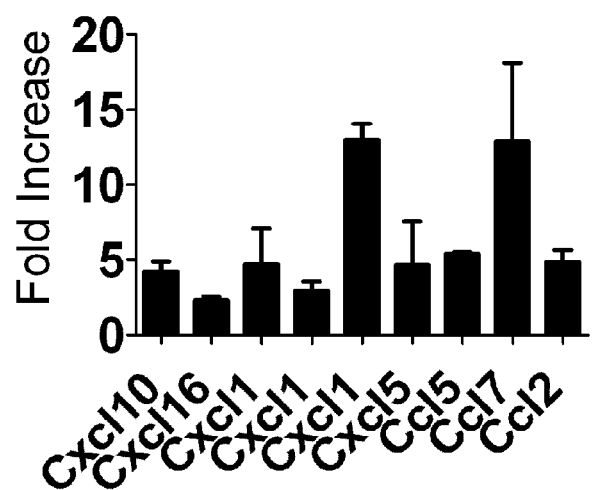
FIG. 3E. Impact of IKKβ expression on chemokine expression in LLC-OVA determined by RNA microarray analysis on an Affymetrix platform. Affymetrix probe set intensity fold increase in indicated chemokine expression in LLC-OVA-IKK compared to LLC-OVA-MiG. Genes identified in two separate microarray experiments are shown, and reported as mean+/−SEM.

A 2-fold cutoff was used to identify genes up-regulated or down-regulated by IKKβ in two independent experiments. In total, 88 genes were up-regulated and 83 genes were down-regulated in both experiments. These included multiple chemokines involved in both T cell and neutrophil chemotaxis (FIG. 3B and FIG. 3E). Amongst T cell chemokines identified, CCL2, CCL5 and CXCL10 are known to mediate activated T cell chemotaxis (Bromley et al., 2008. Nature immunology 9:970-980). RT-PCR confirmed upregulation of CCL2 and CCL5 in LLC-OVA-IKK (FIG. 3C). Similarly, CCL2 and CCL5 expression was also substantially enhanced in LKR-OVA-IKK (data not shown). shRNA mediated knock-down (KD) showed that RelA plays a more important role than cRel or RelB in expression of T cell chemokines in LLC-OVA-IKK.

Figure 3F:
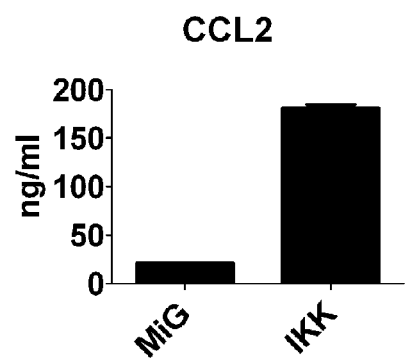
FIG. 3F. LLC-OVA-MiG and LLC-OVA-IKK supernatants were collected 24 h after plating and the amount of secreted CCL2 was determined by ELISA.

CCL2 in particular exhibited a dramatically higher microarray probe set signal than T cell chemokines CCL5 and CXCL10 (FIG. 3B) suggesting it may dominate T cell recruitment responses by LLC-OVA-IKK. In addition, CCL2 protein expression was greatly increased in LLC-OVA-IKK compared to LLC-OVA-MiG (FIG. 3F), as determined by ELISA using the following methods. Supernatant was collected from LLC-OVA-MiG cells and LLC-OVA-IKK cells after 24 h of culture. Anti-CCL2 ELISA was performed to measure CCL2 production in cells and to confirm CCL2 knockdown using the Mouse CCL2 ELISA Ready-SET-Go® kit from eBioscience (San Diego, Calif.) according to the manufacturer's instructions.

Previous studies have indicated an important role for CCL2 in breast cancer metastasis through monocyte recruitment (Qian et al., 2011. Nature 475:222-225) but also in T cell recruitment (Harlin et al., 2009. Cancer research 69:3077-3085). Given high expression and potentially diverse functions, it was determined whether CCL2 was specifically required for rejection of LLC-OVA-IKK tumors by KD of CCL2 expression. CCL2-KD did not impact LLC-OVA-IKK growth in vitro or OVA-specific T cell expansion in vivo. However, while control LLC-OVA-IKK tumors were readily rejected, CCL2-KD resulted in robust tumor growth (FIG. 3D). These results therefore suggest that CCL2 is a potentially crucial immune surveillance regulating NF-kB target gene that is required for LLC-OVA-IKK rejection.

Example 3

Generation of a Gene Expression Signature to Predict NF-kB Activity in Human Lung Cancer Given the above findings in mice, it was next determined whether NF-kB activity is also associated with T cell presence in human lung cancer. It was hypothesized that an NF-kB-driven gene expression signature will provide a superior indication of NF-kB activity than activation state of individual subunits or NF-kB pathway kinases. Furthermore, previous studies have shown the predictive potential of gene expression signatures in determining pathway activation state (Bild et al. 2006. Nature 439:353-357; Chang et al. 2009. Mol Cell 34:104-114). To the best of the present inventors' knowledge, no such gene expression signature exists to predict NF-kB activity in human lung cancer.

Five human lung cancer cell-lines (A549, H23, H358, PC9 and HCC827) were used to generate such a signature. In each cell-line, genes were identified that were impacted by NF-kB inhibition (using retrovirus-expressed IkBαSR "super-repressor" of NF-kB) (Wang et al., 2007. J Immunol 178:6770-6776) and/or NF-kB activation (using CA-IKKβ described above) (Valenzuela et al. 2009. J Clin Invest 119:3774-3786).

Figure 4A:
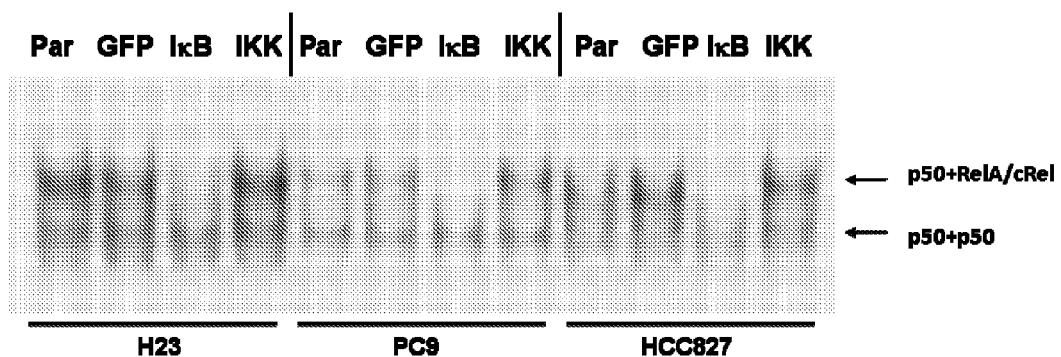
FIGS. 4A-E. Generation and validation of a lung cancer NF-kB signature. (a) EMSA analysis of sorted H23, PC9 and HCC827 cells infected with GFP, IkB or IKKb retroviruses as indicated. Parental (Par) were not infected. The major NF-kB complexes are indicated with arrows. (b) Determination of mRNA expression of NF-kB target genes BIRC3 and TNFAIP3 in low NF-kB signature (H322, H1395, H522, H1437) and high NF-kB signature (H226, H157, H1299, H650) cells. Relative expression is shown after normalizing to 18s rRNA levels. Samples were run in triplicate and reported as average+/−SEM. Students t-test was used to determine statistical significance in difference in mean expression of BIRC3 and TNFAIP3 in low versus high cell lines. (c) H226, H157 and H1299 were transduced with MiG or IkBaSR retroviruses following which BIRC3 and TNFAIP3 mRNA expression was determined as in "b". (d) Expression of CCL2, CCL5, CXCL1-3 and IL8 was determined in H157 cells transduced with MiG and IkBaSR. (e) NF-kB activity determined by EMSA in NF-kB signature low (1-4) and high (5-8) cell lines. Major NF-kB complexes are indicated with arrows.

As shown in FIG. 4A, IkBαSR reduced and CA-IKKβ increased NF-kB heterodimer nuclear activity compared to control MiG retrovirus infected cells. Although NF-kB is widely considered to be a tumor growth-promoting transcription factor, there was surprisingly little effect on survival or proliferation of these 5 lung cancer cell-lines following NF-kB inhibition by IkBαSR expression.

RNA isolated from these 5 cell-lines was used to perform gene expression studies using Affymetrix U133 Plus 2.0 microarrays. Initially, all probe sets impacted 1.4-fold or more by IkBα or IKKβ relative to the control vector were identified in each cell-line. This low stringency cutoff was used to accommodate a second selection criteria. Next, the 5 cell-line signatures were used to identify probe sets similarly regulated by IkBα and IKKβ (with IkBα and IKKβ causing opposite effects on gene expression) in the different cell lines in ≥60% of the experimental conditions (i.e. co-regulation score of ≥0.6). A total of 240 probe sets were identified using this approach (Table 1). The rationale for this was that the identification of genes similarly regulated by NF-kB in multiple cell lines will not only eliminate false positives but also generate a signature that is broadly applicable. As examples, 2 probe sets for the well-known NF-kB target gene BIRC3/cIAP2 (Chu et al., 1997. Proc Natl Acad Sci USA 94:10057-10062; Wang et al., 1998. Science 281:1680-1683) had co-regulation scores of 1.0 and 0.8, and both probe sets of another known NF-kB target gene TNFAIP3/A20 (Harhaj and Dixit, 2011. Cell research 21:22-39) had co-regulation scores of 1.0. In addition, IkBα increased expression of certain genes while IKKβ repressed their expression; these likely represent genes negatively impacted by NF-kB activity. In the 240 probe sets (Table 1), ~200 individual genes were present that were either up-regulated or down-regulated by NF-kB.

TABLE 1

| Up/Down Regulated | Probe ID | GenBank ID | GeneSymbol |
|---|---|---|---|
| Up | 209099_x_at | NM_000214.1 | JAG1 |
| Up | 216268_s_at | NM_000214.1 | JAG1 |
| Up | 202076_at | NM_001166.3 | BIRC2 |
| Up | 210538_s_at | NM_182962.1 | BIRC3 |
| Up | 230499_at | NM_001165 | BIRC3 |
| Up | 225285_at | NM_005504.4 | BCAT1 |
| Up | 202357_s_at | NM_001710.4 | BF |
| Up | 217767_at | NM_000064.1 | C3 |
| Up | 226016_at | NM_001025079.1 | CD47 |
| Up | 211075_s_at | NM_001025079.1 | CD47 |
| Up | 213857_s_at | NM_001025079.1 | CD47 |
| Up | 227259_at | NM_001025079.1 | CD47 |
| Up | 202902_s_at | NM_004079.3 | CTSS |
| Up | 221903_s_at | NM_015247 | CYLD |
| Up | 203725_at | NM_001924.2 | GADD45A |
| Up | 224833_at | NM_005238.2 | ETS1 |

TABLE 1-continued

| Up/Down Regulated | Probe ID | GenBank ID | GeneSymbol |
|---|---|---|---|
| Up | 1555355_a_at | NM_005238.2 | ETS1 |
| Up | 202269_x_at | NM_002053.1 | GBP1 |
| Up | 231577_s_at | NM_002053.1 | GBP1 |
| Up | 204224_s_at | NM_001024070.1 | GCH1 |
| Up | 223278_at | NM_004004.3 | GJB2 |
| Up | 204470_at | NM_001511.1 | CXCL1 |
| Up | 209774_x_at | NM_002089.1 | CXCL2 |
| Up | 207850_at | NM_002090.2 | CXCL3 |
| Up | 208729_x_at | NM_005514.5 | HLA-B |
| Up | 209140_x_at | NM_005514.5 | HLA-B |
| Up | 211911_x_at | AY732487.1 | HLA-C |
| Up | 202637_s_at | NM_000201.1 | ICAM1 |
| Up | 215485_s_at | NM_000201.1 | ICAM1 |
| Up | 202638_s_at | NM_000201.1 | ICAM1 |
| Up | 205207_at | NM_000600.1 | IL6 |
| Up | 204863_s_at | NM_002184.2 | IL6ST |
| Up | 211000_s_at | NM_002184.2 | IL6ST |
| Up | 212195_at | NM_002184 | IL6ST |
| Up | 212196_at | NM_002184 | IL6ST |
| Up | 202859_x_at | NM_000584.2 | IL8 |
| Up | 207536_s_at | NM_001561.4 | TNFRSF9 |
| Up | 211786_at | NM_001561.4 | TNFRSF9 |
| Up | 210511_s_at | NM_002192.2 | INHBA |
| Up | 231779_at | NM_001570.3 | IRAK2 |
| Up | 202531_at | NM_002198.1 | IRF1 |
| Up | 205032_at | NM_002203.2 | ITGA2 |
| Up | 227314_at | NM_002203 | ITGA2 |
| Up | 201389_at | NM_002205.2 | ITGA5 |
| Up | 205786_s_at | NM_000632.3 | ITGAM |
| Up | 202351_at | NM_002210.2 | ITGAV |
| Up | 202267_at | NM_005562.1 | LAMC2 |
| Up | 207517_at | NM_018891.1 | LAMC2 |
| Up | 207339_s_at | NM_009588.1 | LTB |
| Up | 203936_s_at | NM_004994.2 | MMP9 |
| Up | 209239_at | NM_003998.2 | NFKB1 |
| Up | 209636_at | NM_002502.2 | NFKB2 |
| Up | 207535_s_at | NM_002502.2 | NFKB2 |
| Up | 203927_at | NM_004556.2 | NFKBIE |
| Up | 1553994_at | NM_002526 | NT5E |
| Up | 201981_at | NM_002581.3 | PAPPA |
| Up | 206034_at | NM_198833.1 | SERPINB8 |
| Up | 214866_at | NM_001005376.1 | PLAUR |
| Up | 209040_at | NM_004159.4 | PSMB8 |
| Up | 204279_at | NM_002800.4 | PSMB9 |
| Up | 201762_s_at | NM_002818.2 | PSME2 |
| Up | 206157_at | NM_002852.2 | PTX3 |
| Up | 205205_at | NM_006509.2 | RELB |
| Up | 213194_at | NM_002941.2 | ROBO1 |
| Up | 216598_s_at | NM_002982.3 | CCL2 |
| Up | 1405_i_at | NM_002985.2 | CCL5 |
| Up | 205476_at | NM_004591.1 | CCL20 |
| Up | 202307_s_at | NM_000593.5 | TAP1 |
| Up | 225973_at | NM_000544.3 | TAP2 |
| Up | 204769_s_at | NM_000544.3 | TAP2 |
| Up | 208829_at | NM_003190.3 | TAPBP |
| Up | 204924_at | NM_003264.3 | TLR2 |
| Up | 202643_s_at | NM_006290.2 | TNFAIP3 |
| Up | 202644_s_at | NM_006290.2 | TNFAIP3 |
| Up | 205599_at | NM_005658.3 | TRAF1 |
| Up | 235116_at | NM_005658.3 | TRAF1 |
| Up | 208315_x_at | NM_003300.2 | TRAF3 |
| Up | 203299_s_at | NM_003916 | AP1S2 |
| Up | 222549_at | NM_021101.3 | CLDN1 |
| Up | 218182_s_at | NM_021101.3 | CLDN1 |
| Up | 203828_s_at | NM_001012638.1 | IL32 |
| Up | 204440_at | NM_001040280.1 | CD83 |
| Up | 221841_s_at | NM_004235.3 | KLF4 |
| Up | 212636_at | NM 206853.1 | QKI |
| Up | 204702_s_at | NM_004289.5 | NFE2L3 |
| Up | 236471_at | NM_004289 | NFE2L3 |
| Up | 204589_at | NM_014840.2 | NUAK1 |
| Up | 205100_at | NM_005110.1 | GFPT2 |
| Up | 1559064_at | NM_005124 | NUP153 |
| Up | 20320_at | NM_005475.1 | SH2B3 |
| Up | 229564_at | NM_005493 | RANBP9 |
| Up | 201489_at | NM_005729.3 | PPIF |
| Up | 202073_at | NM_001008211.1 | OPTN |
| Up | 202074_s_at | NM_001008211.1 | OPTN |
| Up | 207196_s_at | NM_006058.2 | TNIP1 |
| Up | 204341_at | NM_006470.3 | TRIM16 |
| Up | 213667_at | NM_006662 | SRCAP |
| Up | 220091_at | NM_017585.2 | SLC2A6 |
| Up | 227846_at | BC067106.1 | GPR176 |
| Up | 218644_at | NM_016445.1 | PLEK2 |
| Up | 213524_s_at | NM_015714.2 | G0S2 |
| Up | 220054_at | NM_016584.2 | IL23A |
| Up | 209788_s_at | NM_001040458.1 | ARTS-1 |
| Up | 218834_s_at | NM_178031.2 | HSPA5BP1 |
| up | 218627_at | NM_018370.1 | DRAM |
| Up | 219901_at | NM_018351.2 | FGD6 |
| Up | 220658_s_at | NM_020183.3 | ARNTL2 |
| Up | 224204_x_at | NM_020183.3 | ARNTL2 |
| Up | 222001_x_at | XM_934503.1 | FAM91A2 |
| Up | 229429_x_at | XM_934505.1 | FAM91A2 |
| Up | 209267_s_at | NM_022154.5 | SLC39A8 |
| Up | 219209_at | NM_022168.2 | IFIH1 |
| Up | 219759_at | NM_022350.1 | ERAP2 |
| Up | 218543_s_at | NM_022750.2 | PARP12 |
| Up | 222692_s_at | NM_022763.2 | FNDC3B |
| Up | 229865_at | BC012204.1 | FNDC3B |
| Up | 1568609_s_at | NM_024615.2 | PARP8 |
| Up | 219033_at | NM_024615.2 | PARP8 |
| Up | 220987_s_at | NM_030952.1 | NUAK2 |
| Up | 54970_at | NM_031449.3 | ZMIZ2 |
| Up | 223484_at | NM_032413.2 | C15orf48 |
| Up | 204823_at | NM_014903.3 | NAV3 |
| Up | 232593_at | NM_138397 | LOC93082 |
| Up | 220975_s_at | NM_030968.2 | C1QTNF1 |
| Up | 240770_at | NM_173490 | LOC134285 |
| Up | 205673_s_at | NM_001031739.1 | ASB9 |
| Up | 227599_at | NM_178496.2 | C3orf59 |
| Up | 226725_at | NM_144975 | MGC19764 |
| Up | 241379_at | NM_173545.1 | C2orf13 |
| Up | 212989_at | NM_147156.3 | TMEM23 |
| Up | 225105_at | NM_207376.1 | OCC-1 |
| Up | 229872_s_at | XM_498811.2 | KIAA0493 |
| Up | 229264_at | XM_930678.1 | LOC642441 |
| Up | 1555673_at | XM_937100.1 | LOC728285 |
| Up | 202660_at | NM_002223.2 | ITPR2 |
| Up | 227140_at | NM_002192.2 | INHBA |
| Up | 232060_at | AK000776 | ROR1 |
| Up | 232797_at | AU144005 | ITGAV |
| Up | 230787_at | AW197616 | |
| Up | 236704_at | BG413366 | |
| Down | 202053_s_at | NM_000382.2 | ALDH3A2 |
| Down | 202054_s_at | NM_000382.2 | ALDH3A2 |
| Down | 209442_x_at | NM_020987.2 | ANK3 |
| Down | 231729_at | NM_004058.2 | CAPS |
| Down | 231728_at | NM_004058.2 | CAPS |
| Down | 211922_s_at | NM_001752.2 | CAT |
| Down | 204920_at | NM_001875.2 | CPS1 |
| Down | 217564_at | NM_001875.2 | CPS1 |
| Down | 202295_s_at | NM_004390.2 | CTSH |
| Down | 209782_s_at | NM_001352.2 | DBP |
| Down | 215116_s_at | NM_001005336.1 | DNM1 |
| Down | 37996_s_at | NM_004409.2 | DMPK |
| Down | 204540_at | NM_001958.2 | EEF1A2 |
| Down | 36499_at | NM_001408.1 | CELSR2 |
| Down | 212339_at | NM_177996.1 | EPB41L1 |
| Down | 209189_at | NM_005252.2 | FOS |
| Down | 224863_at | NM_002072 | GNAQ |
| Down | 202756_s_at | NM_002081.1 | GPC1 |
| Down | 1555037_a_at | NM_005896.2 | IDH1 |
| Down | 201193_at | NM_005896.2 | IDH1 |
| Down | 210046_s_at | NM_002168.2 | IDH2 |
| Down | 219922_s_at | NM_021070.2 | LTBP3 |
| Down | 225540_at | NM_002374.3 | MAP2 |
| Down | 209035_at | NM_001012333.1 | MDK |
| Down | 203238_s_at | NM_000435.1 | NOTCH3 |
| Down | 212151_at | NM_002585 | PBX1 |
| Down | 204476_s_at | NM_000920 | PC |
| Down | 206348_s_at | NM_005391.1 | PDK3 |
| Down | 203407_at | NM_002705.3 | PPL |
| Down | 213093_at | NM_002737.2 | PRKCA |

TABLE 1-continued

| Up/Down Regulated | Probe ID | GenBank ID | GeneSymbol |
|---|---|---|---|
| Down | 207011_s_at | NM_152880.2 | PTK7 |
| Down | 203453_at | NM_001038.4 | SCNN1A |
| Down | 208998_at | NM_003355.2 | UCP2 |
| Down | 208997_s_at | NM_003355.2 | UCP2 |
| Down | 205538_at | NM_003389 | CORO2A |
| Down | 211712_s_at | NM_003568.1 | ANXA9 |
| Down | 209641_s_at | NM_003786.2 | ABCC3 |
| Down | 202481_at | NM_004753.4 | DHRS3 |
| Down | 223761_at | NM_005117.2 | FGF19 |
| Down | 225112_at | NM_005759 | ABI-2 |
| Down | 1554018_at | NM_002510 | GPNMB |
| Down | 203961_at | NM_006393 | NEBL |
| Down | 209791_at | NM_007365 | PADI2 |
| Down | 212325_at | NM_014988.1 | LIMCH1 |
| Down | 212328_at | NM_014988.1 | LIMCH1 |
| Down | 212327_at | BX537916.1 | LIMCH1 |
| Down | 227031_at | NM_015132 | SNX13 |
| Down | 202341_s_at | NM_015271.2 | TRIM2 |
| Down | 202342_s_at | NM_015271.2 | TRIM2 |
| Down | 205499_at | NM_014467.1 | SRPX2 |
| Down | 219188_s_at | NM_014067.2 | MACROD1 |
| Down | 221922_at | NM_013296.3 | GPSM2 |
| Down | 219014_at | NM_016619.1 | PLAC8 |
| Down | 220779_at | NM_016233.1 | PADI3 |
| Down | 225355_at | AK096661.1 | DKFZP761M1511 |
| Down | 222496_s_at | NM_019027.1 | RBM47 |
| Down | 221748_s_at | AF172820.1 | MXRA6 |
| Down | 232914_s_at | NM_032379.3 | SYTL2 |
| Down | 218736_s_at | NM_017734.2 | PALMD |
| Down | 226050_at | NM_017905.3 | TMCO3 |
| Down | 218729_at | NM_020169.2 | LXN |
| Down | 220246_at | NM_020397.2 | CAMK1D |
| Down | 213839_at | AB007969.1 | CLMN |
| Down | 232116_at | NM_021180.2 | GRHL3 |
| Down | 218858_at | NM_022783.1 | DEPDC6 |
| Down | 219263_at | NM_024539.3 | RNF128 |
| Down | 218342_s_at | NM_024896.2 | KIAA1815 |
| Down | 222603_at | NM_024896.2 | KIAA1815 |
| Down | 220584_at | NM_025094 | FLJ22184 |
| Down | 224150_s_at | NM_024491.2 | CEP70 |
| Down | 238154_at | NM_024491 | BITE |
| Down | 228084_at | NM_030821 | PLA2G12 |
| Down | 212936_at | NM_032042.3 | C5orf21 |
| Down | 232176_at | NM_032229.2 | SLITRK6 |
| Down | 235976_at | NM_032229.2 | SLITRK6 |
| Down | 232481_s_at | NM_032229.2 | SLITRK6 |
| Down | 227134_at | NM_032872.1 | SYTL1 |
| Down | 228072_at | NM_177963.2 | SYT12 |
| Down | 226597_at | NM_138393.1 | C19orf32 |
| Down | 208158_s_at | NM_018030.3 | OSBPL1A |
| Down | 209485_s_at | NM_080597.2 | OSBPL1A |
| Down | 226325_at | NM_199165.1 | ADSSL1 |
| Down | 225240_s_at | NM_138962 | MSI2 |
| Down | 234974_at | NM_138801 | LOC130589 |
| Down | 235256_s_at | NM_138801.1 | GALM |
| Down | 226875_at | NM_144658.2 | DOCK11 |
| Down | 238029_s_at | NM_152527.3 | SLC16A14 |
| Down | 244261_at | NM_170743.2 | IL28RA |
| Down | 229616_s_at | NM_001012642.1 | GRAMD2 |
| Down | 224990_at | NM_174921.1 | C4orf34 |
| Down | 227052_at | NM_174921 | LOC201895 |
| Down | 228067_at | NM_207362.1 | C2orf55 |
| Down | 224989_at | AI824013 | C4orf34 |
| Down | 235924_at | N73742 | |
| Down | 1565837_at | AA215492 | |
| Down | 227533_at | AA732944 | RALGPS2 |
| Down | 228959_at | AI676241 | |
| Down | 232656_at | AU145501 | NAALADL2 |
| Down | 238441_at | NM_006252.3 | PRKAA2 |
| Down | 238105_x_at | AW294903 | WNT7B |

A substantial number of NF-kB signature genes regulate immune cell chemotaxis (including T cell chemokines CCL2 and CCL5), inflammation and immune regulation (Table 2).

TABLE 2

NF-κB signature genes involved in inflammation and immune regulation

| Inflammation | Adaptive | Adhesion | Complement |
|---|---|---|---|
| IL-6 | HLA-B | CD47 | CFB |
| IL-6 ST | HLA-C | ITGA2 | C3 |
| IL-8 | ICAM1 | ITGA5 | |
| IRAK2 | TNFRSF9 | ITGAM | |
| IRF1 | LTB | ITGAV | |
| CXCL1 | CCL2 | LAMC2 | |
| CXCL2 | CCL5 | CLDN1 | |
| CXCL3 | TAP1 | | |
| PLAUR | TAP2 | | |
| CCL20 | TAPBP | | |
| TLR2 | CD83 | | |
| TRAF1 | IL23A | | |
| TRAF3 | PSMB8 | | |
| IFIH1 | PSMB9 | | |
| | PSME2 | | |
| | IL32 | | |

NF-kB signature genes divided in broad categories based on known functions. The category distinction is not absolute since many genes are involved in multiple listed or other functions. The "Inflammation" category refers to genes involved in inflammation and innate immunity. "Adaptive" refers to genes involved in the adaptive immune response. "Adhesion" refers to genes involved in cell-cell or substrate interactions. "Complement" includes genes involved in the complement pathway.

Using publically available microarray data from 126 different human lung cancer cell lines, cell-lines with high or low NF-kB signature activity were next identified. The microarray data was obtained from GEO at NCBI and Array Express at EBI. It consists of 408 Affymetrix CEL files of 126 different lung cell lines. The scores were calculated based on this set of samples so the high and low are in reference to other cell lines within this group. The probesets that were used to classify the samples were the 240 probes originally identified in the 5 cell lines (i.e. NF-kB signature). The classifier was built and implemented as described (classifier H in supplemental materials and methods) (Shedden et al. 2008. Nat Med 14:822-827). The decision thresholds were made based on the array of measures in the 408 lung CEL file data. The weighted voting classification of each sample scores each gene (probeset) based on where the signal value falls among all the samples in the group. If the probeset was positively correlated with the NF-KB signature (in the original 5 cell lines) then values in the lower third receive a score of −1, values in the middle third receive a 0, and values in the upper third receive a value of 1. If a gene was negatively correlated the values were reversed. The scores for all probesets were summed to provide the final classification score. The data sets used are listed below:

| E-MTAB-37 | Array Express |
|---|---|
| GSE10021 | GEO |
| GSE10843 | GEO |
| GSE13309 | GEO |
| GSE14315 | GEO |
| GSE14883 | GEO |
| GSE15240 | GEO |
| GSE16194 | GEO |
| GSE17347 | GEO |
| GSE18454 | GEO |
| GSE21612 | GEO |
| GSE4824 | GEO |
| GSE5816 | GEO |
| GSE6013 | GEO |
| GSE7562 | GEO |
| GSE8332 | GEO |

NF-kB signature scores were determined by building a classifier that allowed determination of relative signature activity in the different cell-lines, to classify cell lines with low or high NF-kB signature. The classifier was built using methods previously described (Shedden et al. 2008. Nat Med 14:822-827), as follows: A majority vote classifier was used based on the probesets identified in the NF-kB signature. The algorithm consists of three components: the majority vote classifier, the individual classifiers, and the training procedure. The classifier is a majority vote classifier based on the probesets identified that correlate with NF-kB activity in cell lines. The algorithm consisted of three components: the majority vote classifier, the individual classifiers, and the training procedure.

Terminology

C=majority vote of individual classifiers (sum of vote by all probesets in classifier)

$c_k$=individual classifier k (a single probeset and thresholds for that probeset)

$x_j$=sample j (microarray dataset for an array from a single tumor sample)

G=set of genes used for individual classifiers (set of all probesets in classifier)

$g_{jk}$=gene expression value for sample j and probeset k

S=sign (+/−) indicating trend relative to NF-kB activity, +=high expression when NF-kB active=Blue group, −=high expression when NF-kB inactive=Rosy group.

Majority Vote Classifier

Cj=Σ ($c_{kj}$) was the continuous predictor for this classifier, which was categorized into three groups according to the following rule:

$$Pred(xj) = \begin{cases} \text{Blue} & C_j > 0.15 \ |G| \\ \text{Rosy} & C_j < -0.15 \ |G| \\ \text{Grey} & \text{otherwise} \end{cases}$$

The value of 0.15 was heuristically determined depending on the specific prediction corresponding to the Blue or Rosy class. A Pred value of |G| (or −1*|G|) indicated complete agreement with Rosy or Blue group while small values (e.g., 0.15*|G|) indicated uncertainty in voting. As the NF-kB signature may predict NF-kB activity, response to chemotherapy, prognosis, infiltration of lymphocytes, and other biological properties the training process can be used to further tune the constant to maximize predictive success.

Individual Classifier

For each gk element of G

Establish 3 quantiles defined by 2 threshold values, LO and HI:

$$ck = \begin{cases} -1*S_k & g_{jk} < LO \\ +1*S_k & g_{jk} > HI \\ 0 & \text{otherwise} \end{cases}$$

This had the effect of voting −1 for individual genes under-expressed in the samples and +1 for over-expressed genes. The vote was reversed if the gene was negatively correlated to the two groups.

Training Process

The training process required a gene set G (e.g., a gene set identified elsewhere in this proposal) and a reference dataset for each sample class (tumor group) and a biologically known property that might be predicted based on NF-kB activity. The training process began by identifying the LO and HI thresholds for each element gk. All gene expression values were ranked in the reference data set from lowest expression level to highest expression level. The LO threshold was the 33rd percentile value for gene k within all samples of a given tumor class. This value could also be set using a reference dataset of the tumor class to be classified. Likewise the HI threshold was the 66th percentile value for gene k within all samples of a given tumor class or the reference dataset. Once the thresholds were set, the individual classification was applied to all genes (gk).

Next the individual classifiers were summed to generate the Majority Vote score Cj. This represented a continuous variable that represents the relative NF-kB activity in the assessed sample. Classification actually involved defining groups based on the separation of this continuous variable into discrete groups: blue and rosy. The constant (0.15 in the present example) was adjusted to maximally correlate the blue group or rosy group with the biological property that is predicted by the Majority Vote Classifier. This constant was set using the reference dataset for each tumor group and biological process.

Next, it was determined whether differences in NF-kB signature correlated with differences NF-kB nuclear presence, i.e., activity. Four NF-kB low and 4 NF-kB high signature cell lines were compared in a side by side analysis using EMSA. Based on this analysis, 4 cell lines that were identified with high NF-kB signature (H226, H157, H1299, H650) and 4 cell lines with low NF-kB signature (H322, H1395, H522, H1437) were used for additional studies.

Figure 4B:
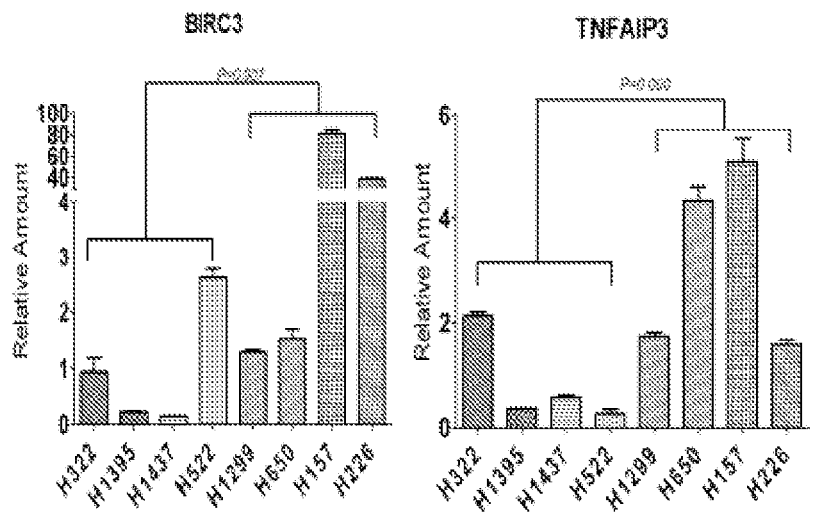

Genes present in the NF-kB signature may also be regulated by non-NF-kB pathways. Thus, while H226, H157, H1299 and H650 cell-lines have high expression of NF-kB signature genes, it is unclear whether this is indeed due to NF-kB activity. To test this, expression of the two signature genes with high co-regulation scores (BIRC3 and TNFAIP3) was determined in these 8 cell-lines. Despite variation in expression in individual cell-lines, NF-kB high cell-lines had significantly higher mean expression of both BIRC3 and TNFAIP3 compared to NF-kB low cell-lines (FIG. 4B).

Figure 4C:
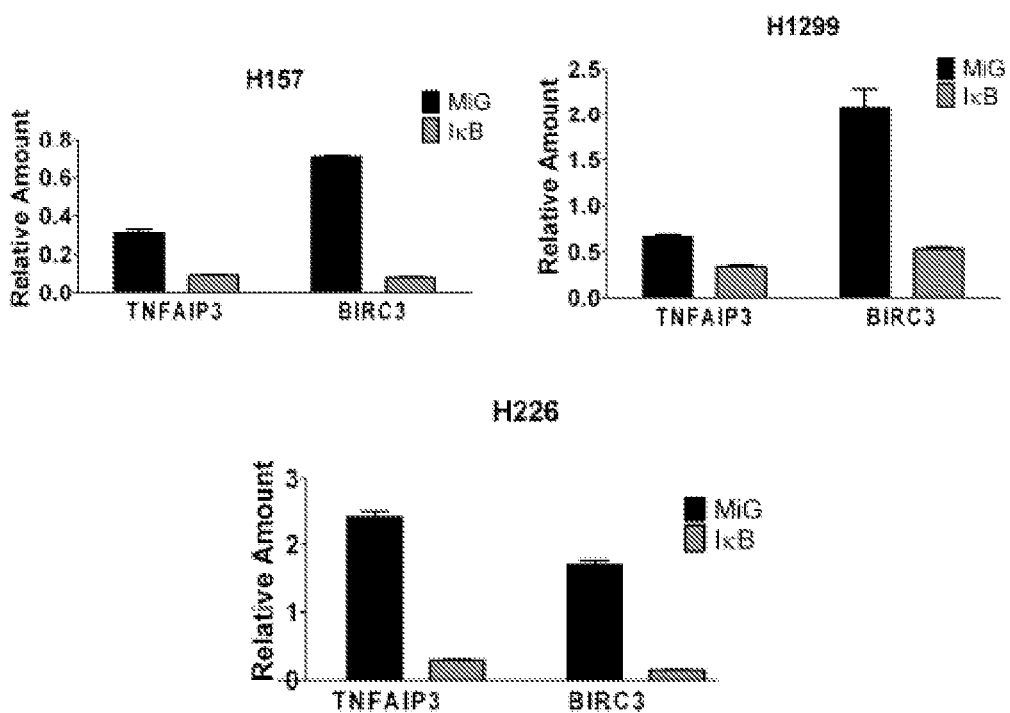
Figure 4D:
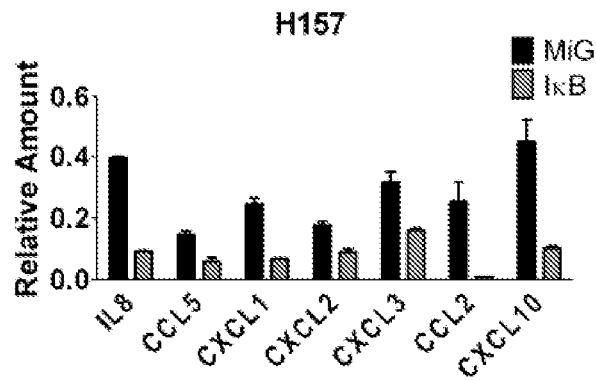

To determine NF-kB involvement, H226, H157 and H1299 cells were transduced with MiG and IkBαSR retroviruses (H650 showed little or no retrovirus infection). Importantly, expression of both genes was significantly reduced by IkBαSR expression (FIG. 4C). Similar results were obtained for additional genes including CCL2, CCL5, CXCL1-3 and IL8 (FIG. 4D). These results therefore indicate that high expression of NF-kB signature genes in these cell-lines is dependent on NF-kB activity.

Figure 4E:
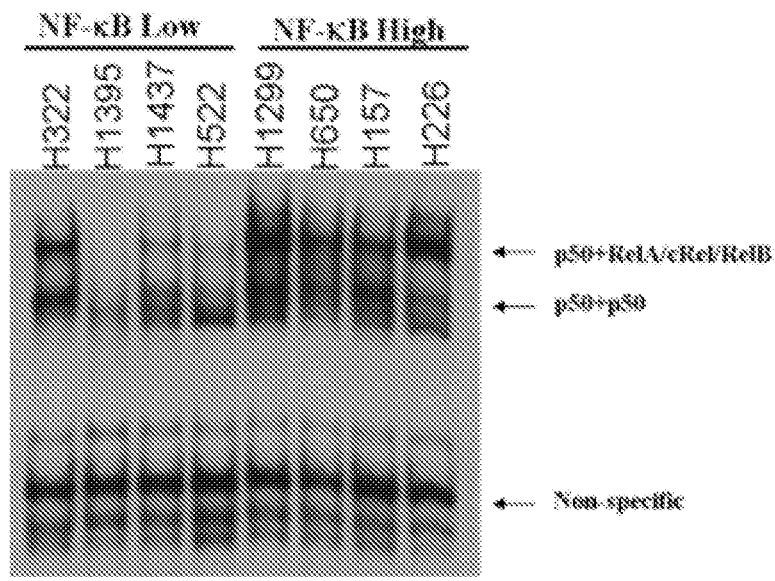

The next experiments were performed to evaluate an association between the NF-kB signature and NF-kB DNA binding activity. Importantly, EMSA showed that the 4 lines with high NF-kB signature indeed had high kB-site binding activity (FIG. 4E). However, the NF-kB signature low H322 cell-line also showed high NF-kB activity (FIG. 4E). Therefore, NF-kB DNA binding activity alone does not provide an unambiguous indication of NF-kB transcriptional activity.

To seek a better understanding of NF-kB function in human lung cancer, the signature was next used for studies in human lung adenocarcinoma. Specifically, the correlation between NF-kB regulated chemokine gene expression and T cell presence was determined, as well as the association of these genes with patient survival.

Example 4

Figure 5A:
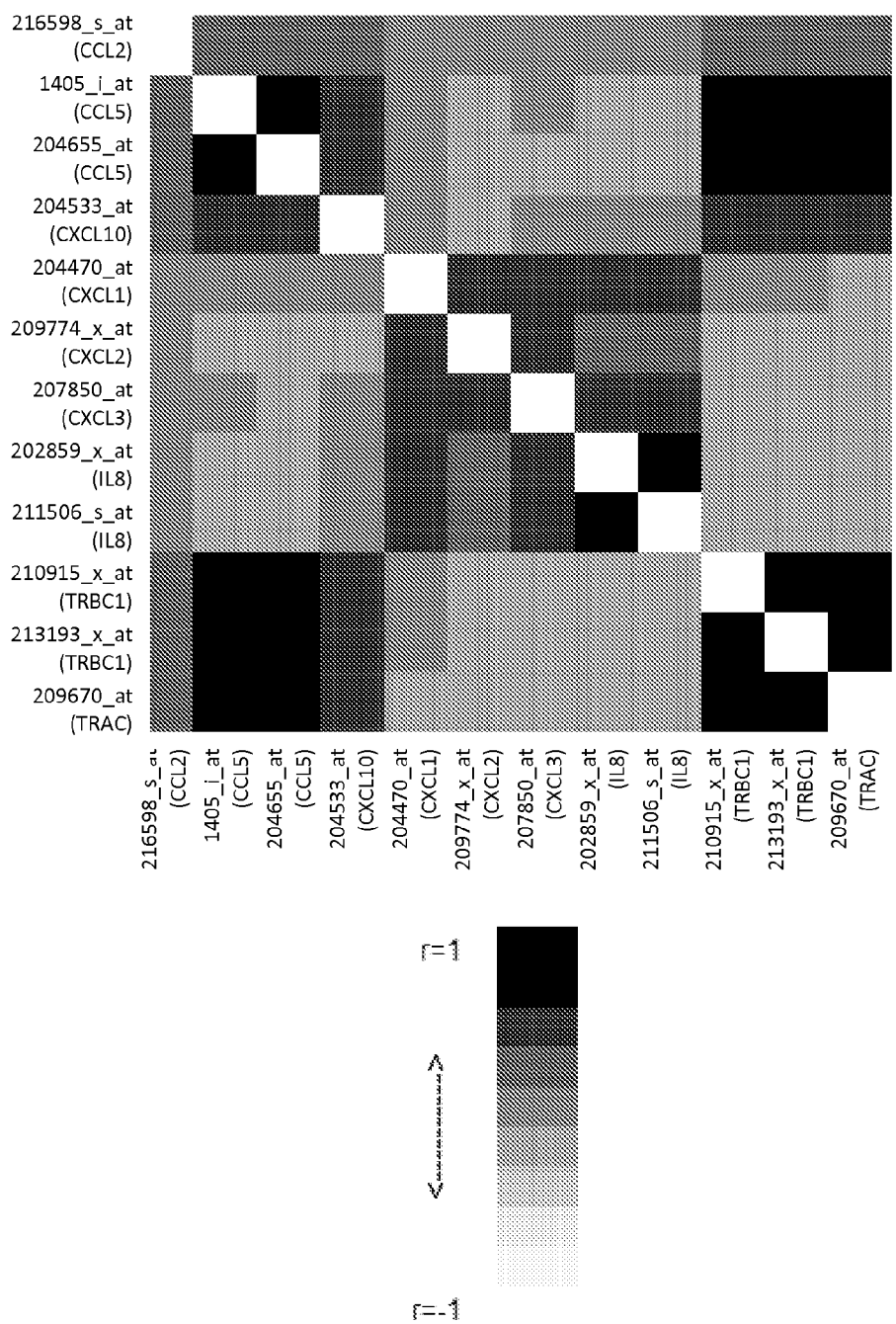
FIGS. 5A-D. Association of T cell chemokines, but not neutrophil chemokines, with T cell presence in human lung adenocarcinoma. (a) Correlation plot based on Spearman correlation r-value of CMCLA gene expression data in human adenocarcinomas (n=442) for T cell chemokines (CCL2, CCL5, CXCL10), neutrophil chemokines (CXCL1-3, IL8), and T cell receptor (TRAC, TRBC1) genes. Gene names and Affymetrix probe set ID numbers are shown. (b) Correlation r-values of LTb expression with T cell chemokines, neutrophil chemokines, and T cell presence in CMCLA dataset (n=442). Gene name and Affymetrix probe set ID numbers for genes with 2 probe sets are shown. (c) mRNA expression of indicated genes normalized to 18s rRNA in HCC827 lung cancer cells determined by RT-PCR. Fold difference in expression of genes after LT treatment compared to untreated cells is shown. Samples were run in triplicate and reported as mean+/−SEM. (d) mRNA expression of indicated genes normalized to 18s rRNA in HCC827 lung cancer cells determined by RT-PCR. Fold difference in expression of genes after TNFa treatment compared to untreated cells is shown. Samples were run in triplicate and reported as mean+/−SEM.

Association of T Cell Chemokines, but not Neutrophil Chemokines, with T Cell Presence in Human Lung Cancer The association of different chemokines present in the NF-kB signature with T cell presence was determined. For these studies, the Consortium for the Molecular Classification of Lung Adenocarcinoma (CMCLA) survival prediction study (59) was used. CMCLA is the largest and most comprehensive study in which microarray-based gene expression data from tumors was used to predict survival of 442 early stage lung adenocarcinoma patients (Shedden et al. 2008. Nat Med 14:822-827). Tumor samples used were from four different institutions including the Moffitt Cancer Center (Shedden et al. 2008). Specifically, the experiments determined whether neutrophil (CXCL1-3 and IL8) and T cell chemokines (CCL2, CCL5 and CXCL10) were differentially associated with T cell presence (although CXCL10 did not achieve the criteria for inclusion in the NF-kB signature, it was included in this analysis because it was identified as a target gene in LLC and in some human cell-lines). To detect T cells, T cell receptor α (TRAC) and β chain (TRBC1) gene expression was used as a marker for T cell presence. As expected, TRAC expression was highly correlated with TRBC1 expression (FIG. 5A). Importantly, CCL2, CCL5 and CXCL10, but not neutrophil chemokine expression (CXCL1-3 and IL8), was positively correlated with these T cell markers (FIG. 5A). These results therefore indicate a functional link between T cell chemokine expression and T cell presence in tumors. Interestingly, expression of neutrophil chemokine genes was highly correlated with each other (FIG. 5A) suggesting that NF-kB regulated inflammatory and immune response functions predominate in different tumors. To help understand how genes associated with different NF-kB functions may be differentially regulated, their association with key NF-kB activators was determined.

Example 5

Figure 5B:
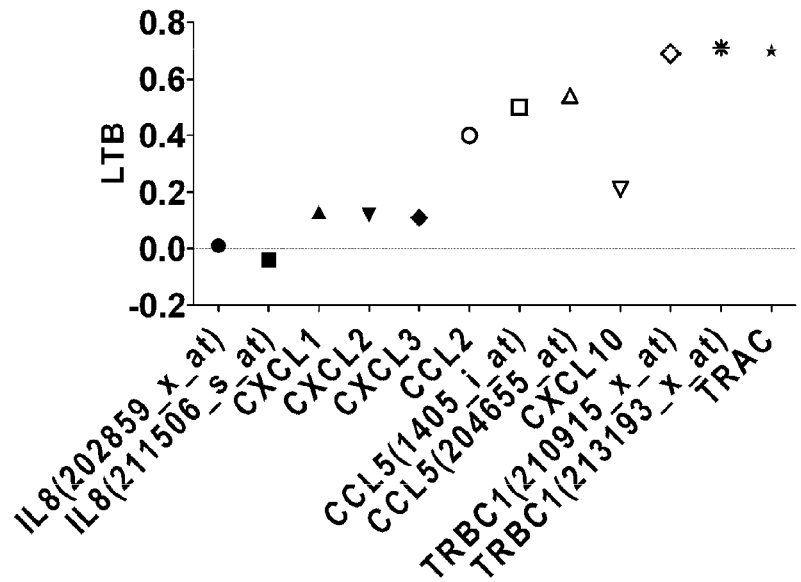
Figure 5C:
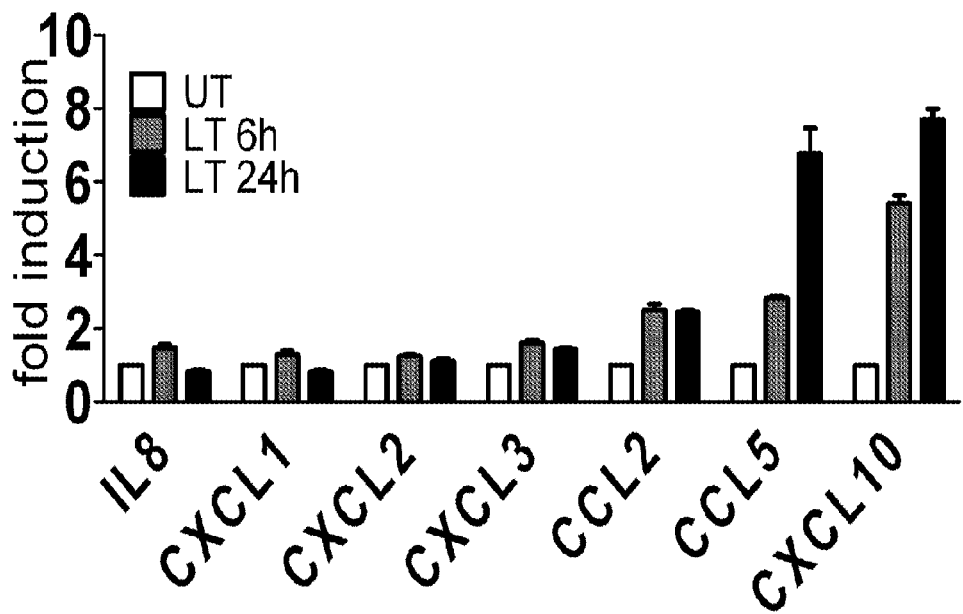
Figure 5D:
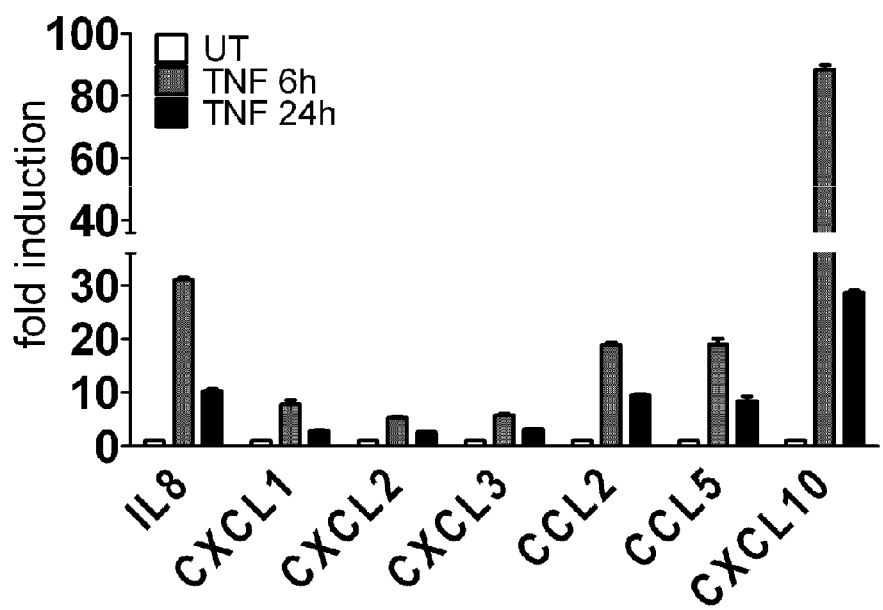
Figure 5E:
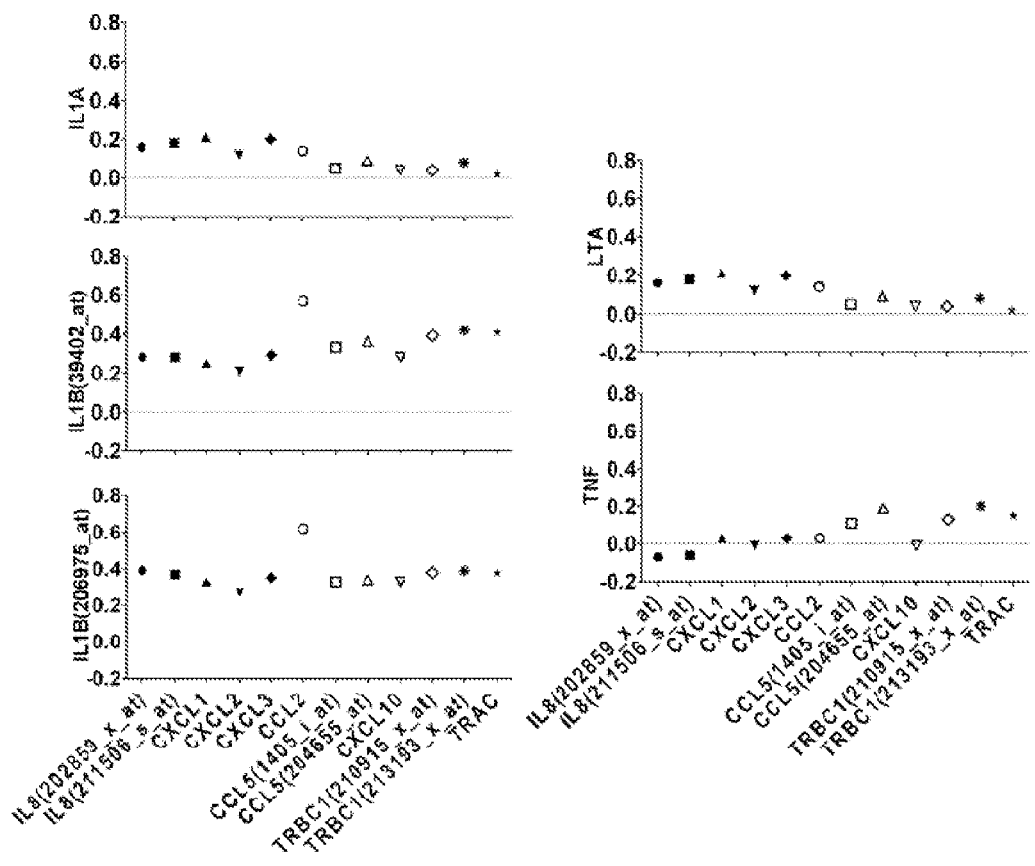
FIG. 5E. Correlation of expression between genes in human lung adenocarcinoma. Correlation r-values of expression of different NF-kB activating cytokine genes (y-axis) with expression of different genes (x-axis). Gene name and Affymetrix probe set numbers for genes with 2 probe sets are shown.
Figure 6A:
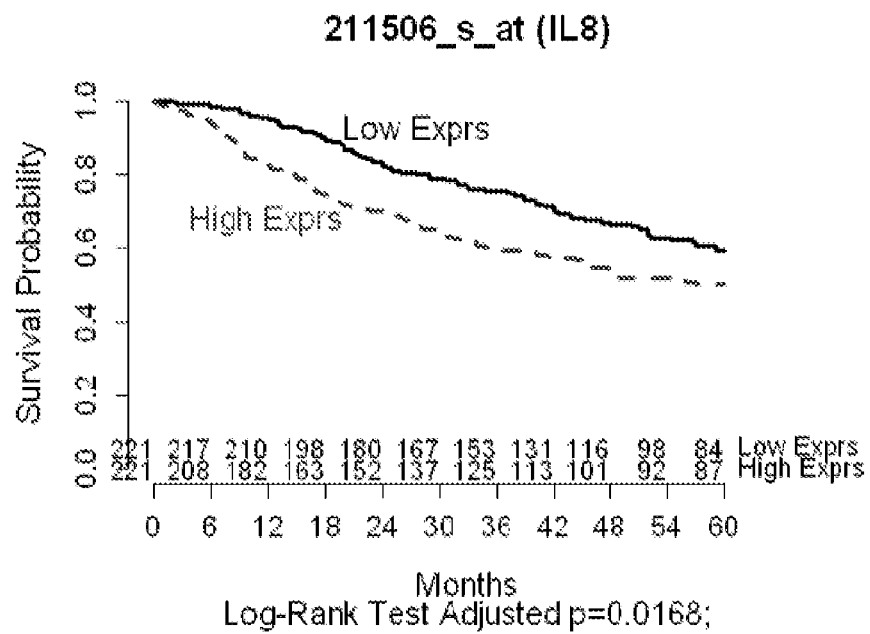
FIGS. 6A-D. Association of NF-kB signature inflammatory genes with patient survival. (a-d) Association of mRNA expression of indicated inflammatory genes (and Affymetrix probe set ID) with OS in CMCLA dataset (n=442). 5-year OS of patients exhibiting high versus low expression of indicated genes using a median cutoff. Kaplan-Meier method was used to generate survival curves and the log-rank test was used to test survival difference between the low and high expression groups by median cutoff for each gene. The p-value shown was adjusted by false discovery rate (FDR) for multiple testing.
Figure 6B:
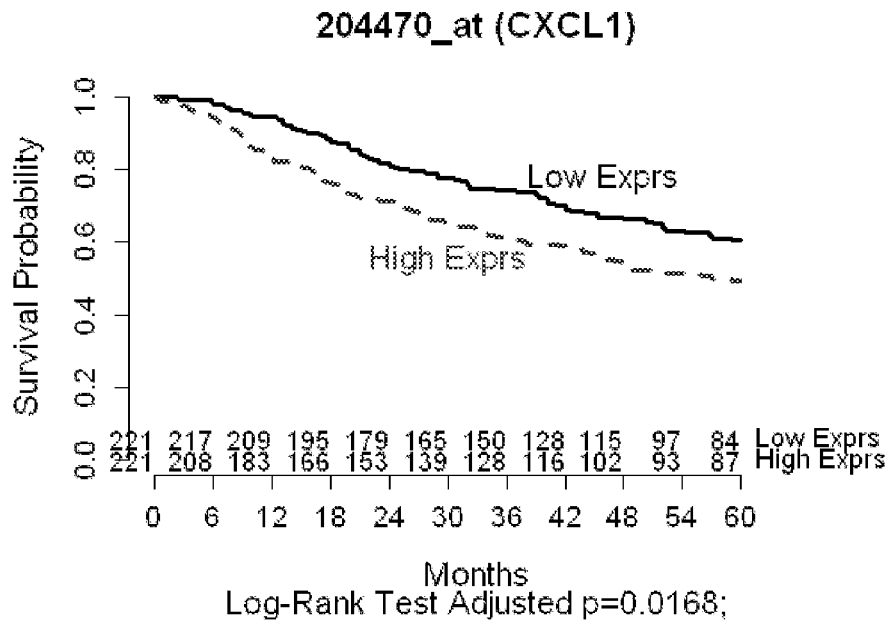
Figure 6C:
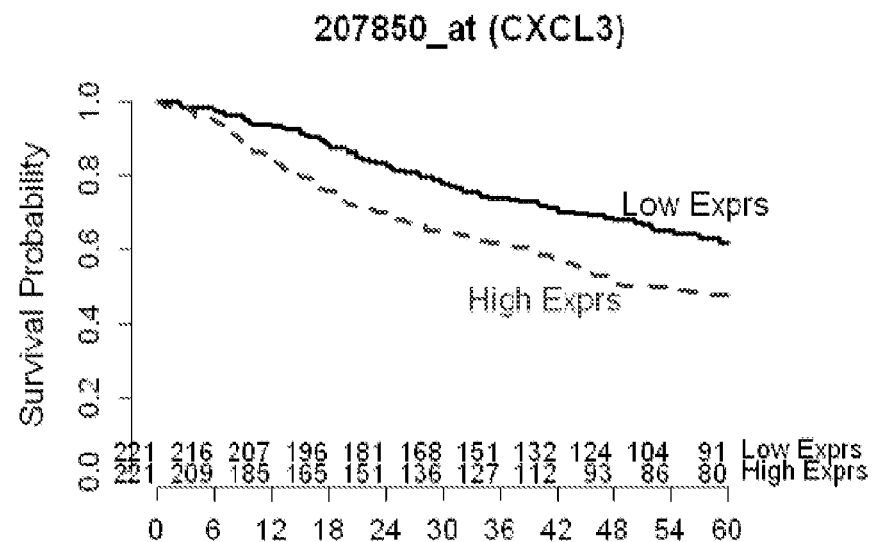
Figure 6D:
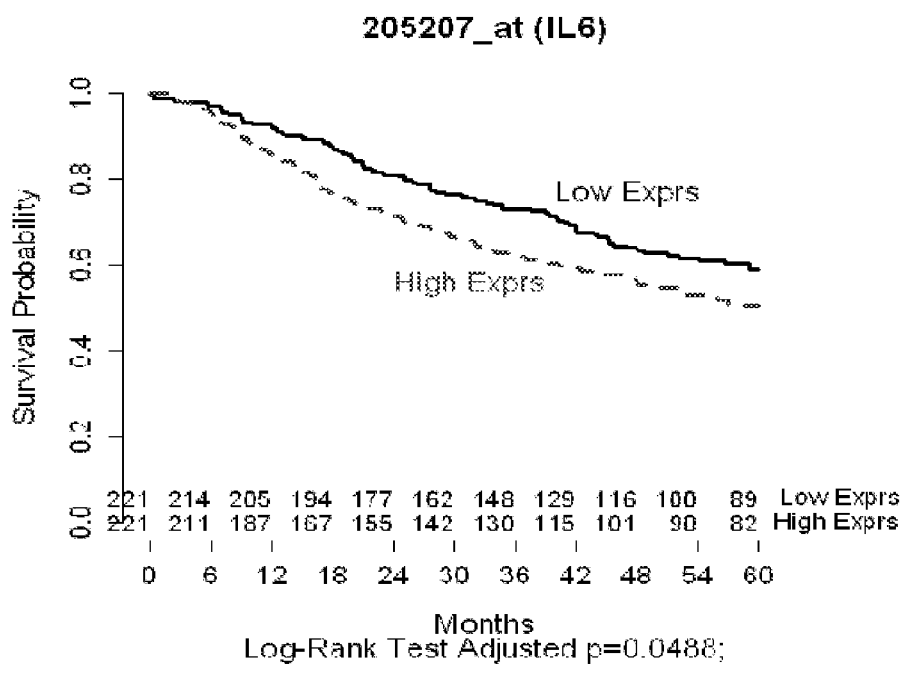

LTβ Expression is Differentially Associated with T Cell Chemokines in Human Lung Cancer Multiple NF-kB-activating cytokines may be present in the lung tumor microenvironment (Mantovani, A., Allavena, P., Sica, A., and Balkwill, F. 2008. Cancer-related inflammation. Nature 454:436-444). To identify cytokines potentially involved in differential expression of T cell versus neutrophil chemokines, association with expression of TNFα, IL-1α, IL-1β, LTα(TNFβ) and LTβ was tested. These cytokines not only induce NF-kB activation but can also be transcriptionally regulated by NF-kB. However, only LTβ was identified as an NF-kB target gene in lung cancer cells (Table 2) and interestingly, only LTβ showed a greater correlation with expression of T cell chemokines versus neutrophil chemokines (FIGS. 5B and 5E). LTβ receptor (LTβR) engagement by heterodimers of LTα and LTβ (LTα1/β2) activates NF-kB RelA and RelB, typically in association with p52 (Bonizzi and Karin, 2004. Trends Immunol 25:280-288; Dejardin et al., 2002. Immunity 17:525-535; Gommerman and Browning, 2003. Nature reviews. Immunology 3:642-655; Wolf et al., 2010. Oncogene 29:5006-5018). Mirroring correlation in tumors, soluble LTα1/β2 (LT) induced expression of T cell chemokines but not neutrophil chemokines in human lung cancer cells (FIG. 5C). In contrast, TNFα strongly induced both neutrophil and T cell chemokines (FIG. 5D). These results suggest that differential expression of NF-kB regulated T cell chemokines versus neutrophil chemokines in human lung cancer could be achieved through agents that selectively induce these different chemokine subsets, such as the LTβR ligand.

Example 6

NF-kB Signature Genes are Associated with Distinct Overall Survival of Lung Cancer Patients The above results indicate that NF-kB regulated inflammatory and immune response genes are differentially expressed in lung cancer. The next experiments determined whether expression of these genes was also associated with distinct overall survival (OS) of patients. Using the CMCLA dataset, 5-year OS of patients exhibiting high versus low expression of these genes was determined using a median cutoff. A striking effect on survival was seen for NF-kB target genes involved in neutrophil chemotaxis and inflammation (IL8, CXCL1, CXCL3 and IL6), all of which were associated with significantly poor OS (FIG. 6A-D).

Figure 7A:
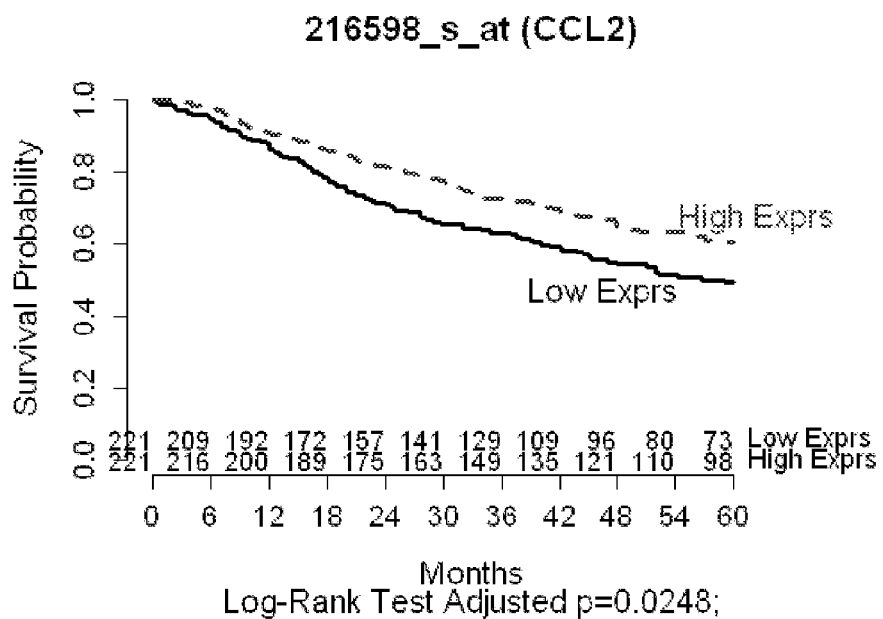
FIGS. 7A-E. Association of NF-kB signature immune response genes and T cell presence with patient survival. (a-d) Association of mRNA expression of indicated immune response genes (and Affymetrix probe set ID) with OS in CMCLA (n=442). 5-year OS of patients exhibiting high versus low expression of indicated genes using a median cutoff. Kaplan-Meier method was used to generate survival curves and the log-rank test was used to test survival difference between the low and high expression groups by median cutoff for each gene. The p value shown was adjusted by false discovery rate (FDR) for multiple testing. (e) Association of T cell presence detected by expression of T cell receptor genes (TRAC, TRBC1) on patient survival was determined as with above genes.
Figure 7B:
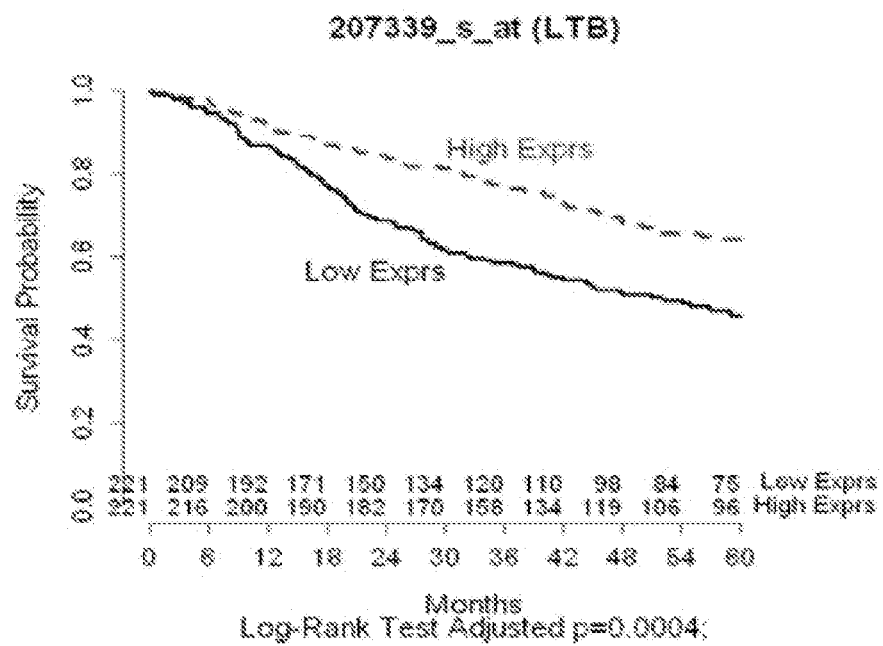
Figure 7C:
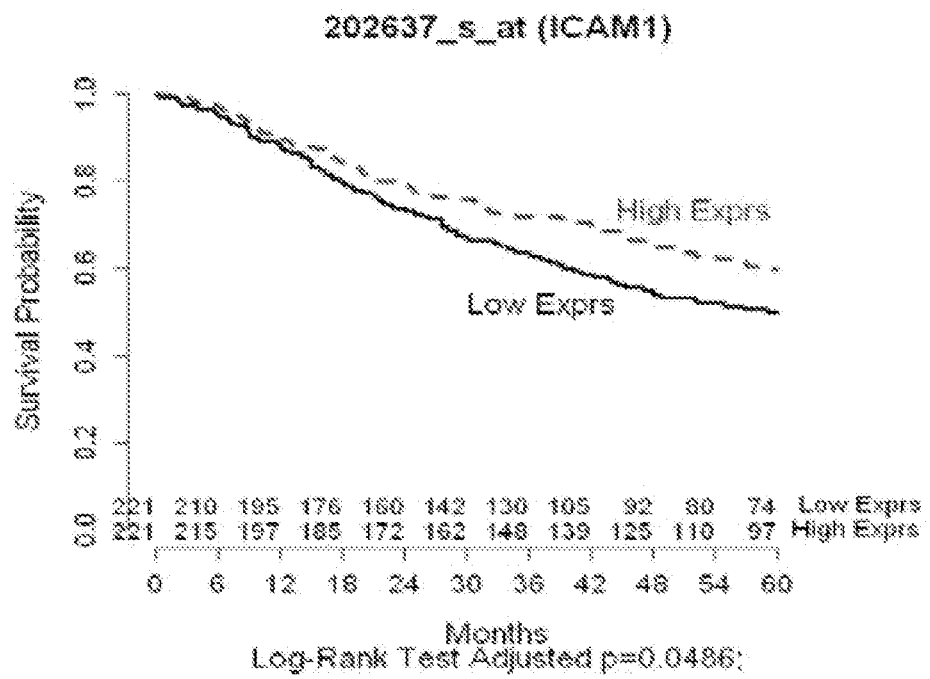
Figure 7D:
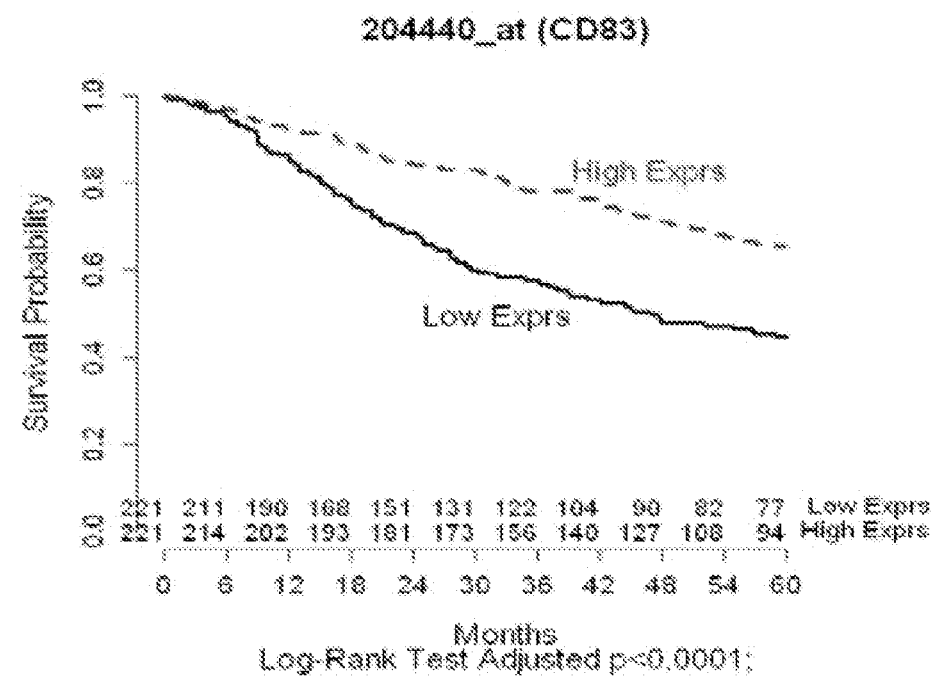
Figure 7E:
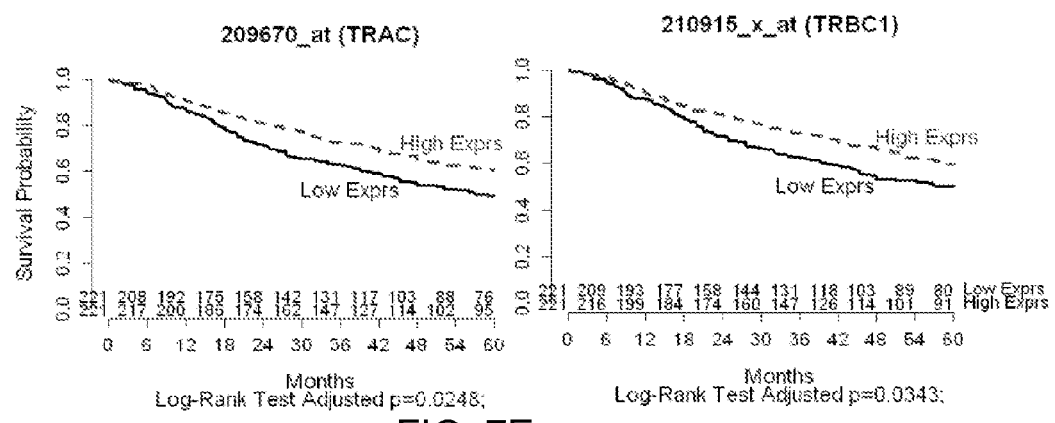

Poor survival in human cancer is associated with increased metastasis. Both IL-8 and CXCL1 have been linked to increased metastasis through effects on infiltrating myeloid cells (Sparmann and Bar-Sagi, 2004. Cancer Cell 6:447-458; Acharyya et al. 2012. Cell 150:165-178), suggesting association with poor survival can be through increased metastatic dissemination. On the other hand, high expression of a subset of genes involved in T cell chemotaxis and T cell responses, including CCL2, LTβ, ICAM-1 and CD83, was associated with significantly improved OS (FIG. 7A-D). LTβ association with improved OS was especially pronounced, perhaps because LTβ can enhance expression of multiple genes involved in T cell responses. Importantly, high expression of TCRα and β chain genes was also associated with significantly improved OS in lung cancer patients (FIG. 7E). Therefore, while both T cell presence and expression of NF-kB signature genes associated with T cell responses is associated with improved OS, the high expression of inflammatory genes is associated with poor OS. Hence, distinct functions of NF-kB in human lung cancer are associated with potentially different survival outcomes.

Example 7

NF-kB Activity in Human Lung Cancer is Strongly Associated with T Cell Presence

The above findings indicate differential expression of distinct NF-kB target genes in tumors. By allowing investigation of combined expression of signature genes, principal component analysis (PCA) can simplify evaluation of pathway-dependent gene expression activity and has been widely used to derive and validate gene signatures in various cancer studies (Chen et al., 2011. Journal of the National Cancer Institute 103:1859-1870; Chen et al., 2010. Breast cancer research and treatment 119:335-346; Chen et al., 2010. Breast cancer research and treatment 120:25-34). The first principal component ($1^{st}$ PC), (principal component analysis—PCA) was used, as it accounted for the largest variability in the data, to represent the overall expression level for NF-kB activation. That is, NF-kB activation score=$\Sigma w_i x_i$, a weighted average expression among the NF-kB activated genes, where $x_i$ represents gene i expression level, $w_i$ is the corresponding weight (loading coefficient) with $\Sigma w_i^2 = 1$, and the $w_i$ values maximize the variance of $\Sigma w_i x_i$.

This approach has been used to derive a malignancy pathway gene signature in a breast cancer study (Chen et al., 2010. Breast Cancer Res Treat 119:335-346). The Cox proportional hazards model was used to analyze the continuous NF-kB activation score to determine if it can predict survival.

Of the 240 NF-kB signature probe sets present in Affymetrix U133 Plus 2.0 microarrays, 159 were present (Table 3) in the CMCLA dataset which used Affymetrix 133A (Shedden et al., 2008).

TABLE 3

| Probe ID | Gene Symbol | Probe ID | Gene Symbol |
| --- | --- | --- | --- |
| 209099_x_at | JAG1 | 218644_at | PLEK2 |
| 216268_s_at | JAG1 | 213524_s_at | G0S2 |
| 202076_at | BIRC2 | 220054_at | IL23A |
| 210538_s_at | BIRC3 | 209788_s_at | ERAP1 |
| 202357_s_at | NA | 218834_s_at | TMEM132A |
| 217767_at | C3 | 218627_at | DRAM1 |
| 211075_s_at | CD47 | 219901_at | FGD6 |
| 213857_s_at | CD47 | 220658_s_at | ARNTL2 |
| 202902_s_at | CTSS | 222001_x_at | LOC728855 |
| 221903_s_at | CYLD | 209267_s_at | SLC39A8 |
| 203725_at | GADD45A | 219209_at | IFIH1 |
| 202269_x_at | GBP1 | 219759_at | ERAP2 |
| 204224_s_at | GCH1 | 218543_s_at | PARP12 |
| 204470_at | CXCL1 | 219033_at | PARP8 |
| 209774_x_at | CXCL2 | 220987_s_at | NA |
| 207850_at | CXCL3 | 54970_at | ZMIZ2 |
| 208729_x_at | HLA-B | 204823_at | NAV3 |
| 209140_x_at | HLA-B | 220975_s_at | C1QTNF1 |
| 211911_x_at | HLA-B | 205673_s_at | ASB9 |
| 202637_s_at | ICAM1 | 212989_at | SGMS1 |
| 215485_s_at | ICAM1 | 202660_at | ITPR2 |
| 202638_s_at | ICAM1 | 202053_s_at | ALDH3A2 |
| 205207_at | IL6 | 202054_s_at | ALDH3A2 |
| 204863_s_at | IL6ST | 209442_x_at | ANK3 |
| 211000_s_at | IL6ST | 211922_s_at | CAT |
| 212195_at | IL6ST | 204920_at | CPS1 |
| 212196_at | IL6ST | 217564_s_at | CPS1 |
| 202859_x_at | IL8 | 202295_s_at | CTSH |
| 207536_s_at | TNFRSF9 | 209782_s_at | DBP |
| 211786_at | TNFRSF9 | 215116_s_at | DNM1 |
| 210511_s_at | INHBA | 37996_s_at | DMPK |
| 202531_at | IRF1 | 204540_at | EEF1A2 |
| 205032_at | ITGA2 | 36499_at | CELSR2 |
| 201389_at | ITGA5 | 212339_at | EPB41L1 |
| 205786_s_at | ITGAM | 209189_at | FOS |
| 202351_at | ITGAV | 202756_s_at | GPC1 |
| 202267_at | LAMC2 | 201193_at | IDH1 |
| 207517_at | LAMC2 | 210046_s_at | IDH2 |
| 207339_s_at | LTB | 219922_s_at | LTBP3 |
| 203936_s_at | MMP9 | 209035_at | MDK |
| 209239_at | NFKB1 | 203238_s_at | NOTCH3 |
| 209636_at | NFKB2 | 212151_at | PBX1 |
| 207535_s_at | NFKB2 | 204476_s_at | PC |
| 203927_at | NFKBIE | 206348_s_at | PDK3 |
| 201981_at | PAPPA | 203407_at | PPL |
| 206034_at | SERPINB8 | 213093_at | PRKCA |
| 214866_at | PLAUR | 207011_s_at | PTK7 |
| 209040_s_at | PSMB8 | 203453_at | SCNN1A |
| 204279_at | PSMB9 | 208998_at | UCP2 |
| 201762_s_at | PSME2 | 208997_s_at | UCP2 |
| 206157_at | PTX3 | 205538_at | CORO2A |
| 205205_at | RELB | 211712_s_at | ANXA9 |
| 213194_at | ROBO1 | 209641_s_at | ABCC3 |
| 216598_s_at | CCL2 | 202481_at | DHRS3 |
| 1405_i_at | CCL5 | 203961_at | NEBL |
| 205476_at | CCL20 | 209791_at | PADI2 |
| 202307_s_at | TAP1 | 212325_at | LIMCH1 |
| 204769_s_at | TAP2 | 212328_at | LIMCH1 |
| 208829_at | TAPBP | 212327_at | LIMCH1 |
| 204924_at | TLR2 | 202341_s_at | TRIM2 |
| 202643_s_at | TNFAIP3 | 202342_s_at | TRIM2 |
| 202644_s_at | TNFAIP3 | 205499_at | SRPX2 |
| 205599_at | TRAF1 | 219188_s_at | MACROD1 |
| 208315_x_at | TRAF3 | 221922_at | GPSM2 |
| 203299_s_at | AP1S2 | 219014_at | PLAC8 |
| 218182_s_at | CLDN1 | 220779_at | PADI3 |
| 203828_s_at | IL32 | 221748_s_at | TNS1 |
| 204440_at | CD83 | 218736_s_at | PALMD |
| 221841_s_at | KLF4 | 218729_at | LXN |

TABLE 3-continued

| Probe ID | Gene Symbol | Probe ID | Gene Symbol |
| --- | --- | --- | --- |
| 212636_at | QKI | 220246_at | CAMK1D |
| 204702_s_at | NFE2L3 | 213839_at | CLMN |
| 204589_at | NUAK1 | 218858_at | DEPDC6 |
| 205100_at | GFPT2 | 219263_at | RNF128 |
| 203320_at | SH2B3 | 218342_s_at | ERMP1 |
| 201489_at | PPIF | 220584_at | FLJ22184 |
| 202073_at | OPTN | 212936_at | FAM172A |
| 202074_s_at | OPTN | 208158_s_at | OSBPL1A |
| 207196_s_at | TNIP1 | 209485_s_at | OSBPL1A |
| 204341_at | TRIM16 | | |
| 213667_at | SRCAP | | |
| 220091_at | SLC2A6 | | |

Figure 8A:
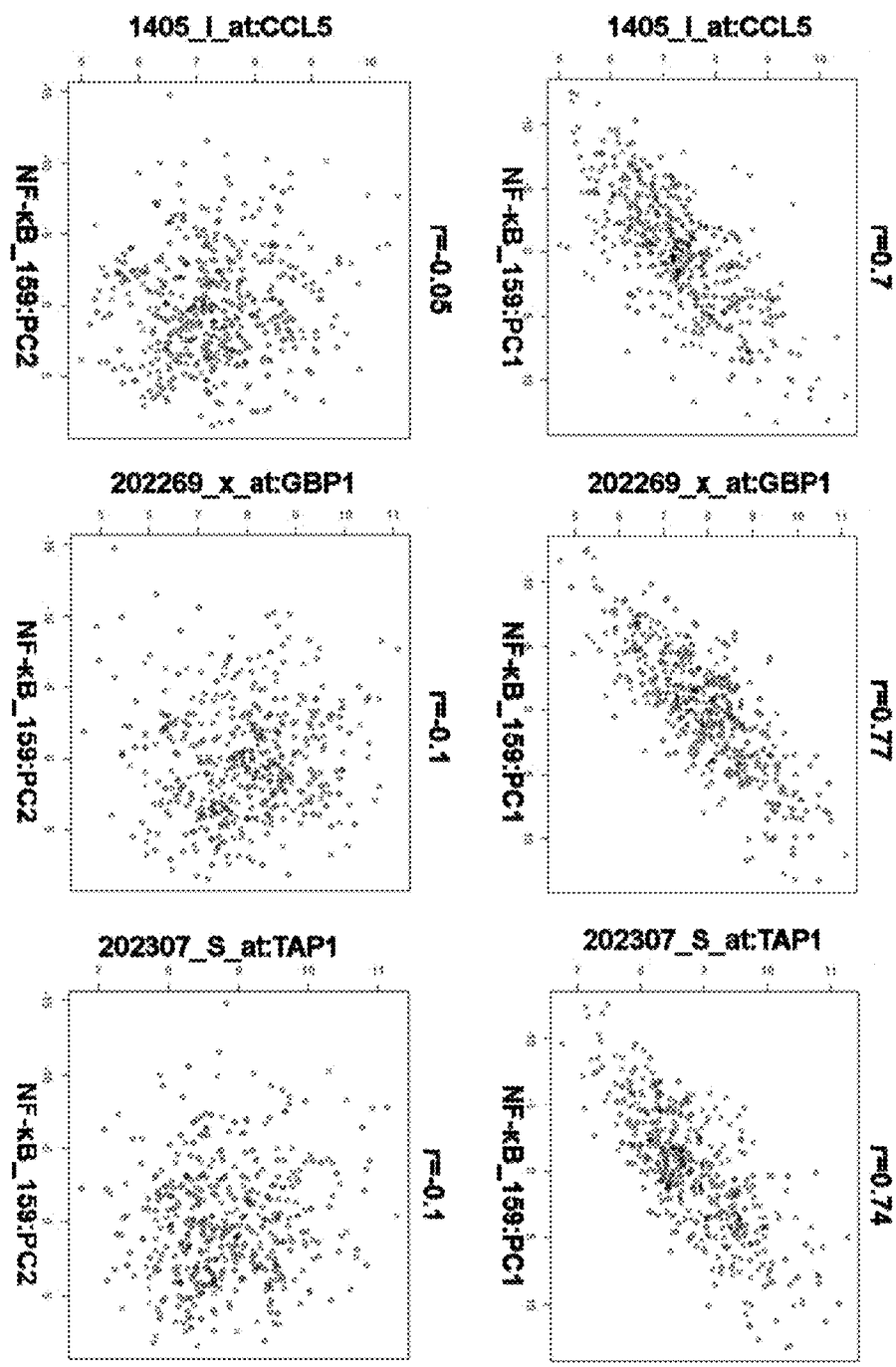
FIGS. 8A-D Correlation of expression between each of the ten NF-κB driver genes (y-axis) and PC1 (top panels) and PC2 (bottom panels) of the NF-κB signature 159 probesets (x-axis) in the CMCLA dataset. Correlation r-values, gene names and Affymetrix probe set ID are shown.
Figure 8B:
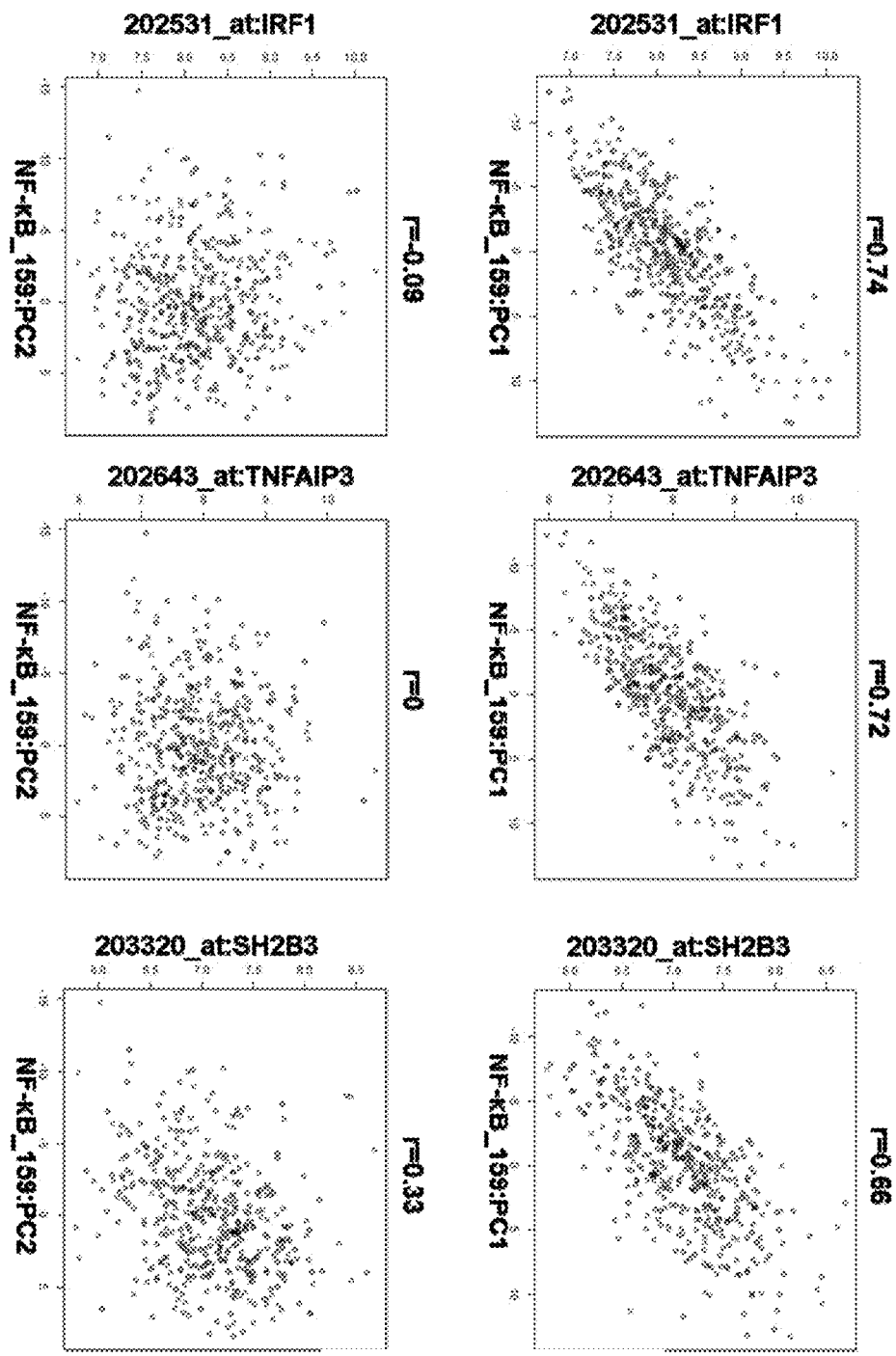
Figure 8C:
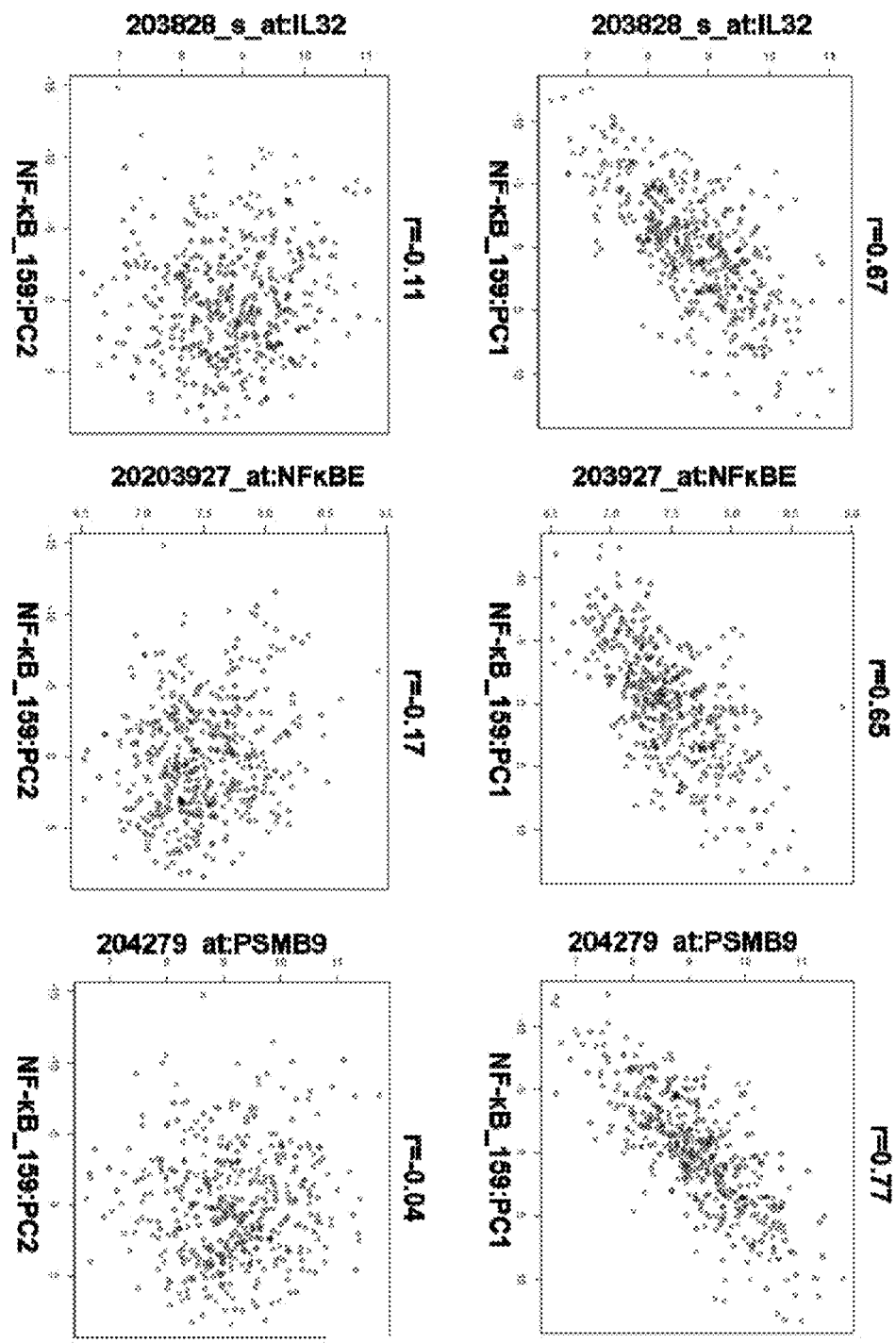
Figure 8D:
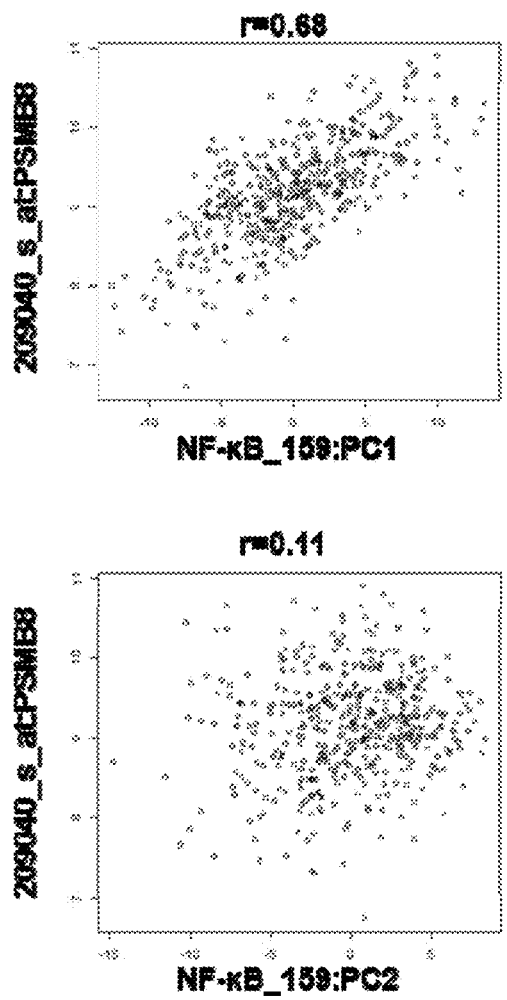
Figure 8E:
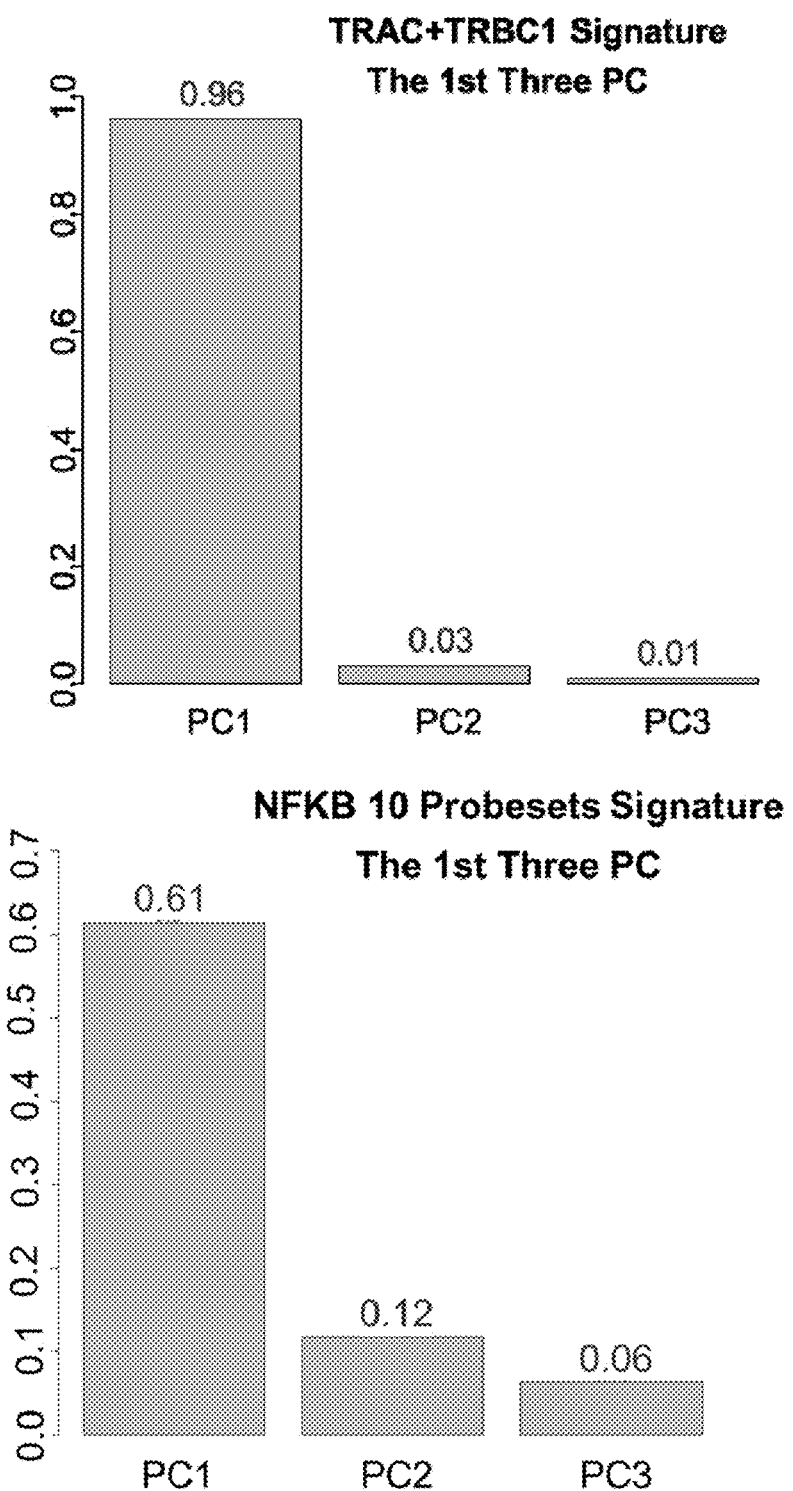
FIG. 8E. The first 3 Principal Components (PC1-3) of the T cell receptor genes (TRAC and TRBC1) (Top panel) or the ten-gene NF-kB signature (bottom panel) are shown in the CMCLA dataset.
Figure 8F:
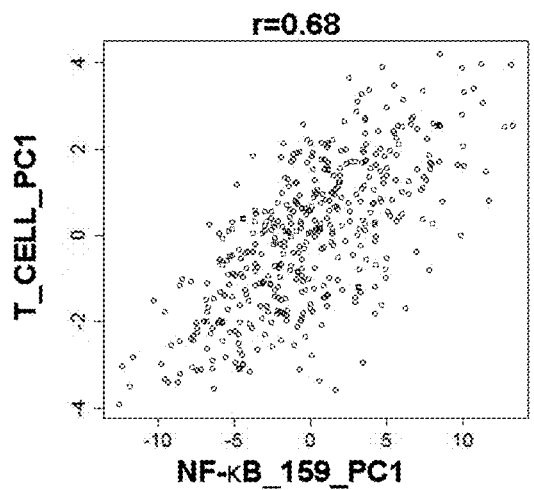
FIGS. 8F-J. Association of T cell presence with NF-kB activity in human lung cancer. (c) Spearman correlation plot with r-value of NF-kB signature (159 probe sets) PC1 with T cell PC1 are shown for CMCLA data (n=442). (d) Correlation plot of NF-kB signature (159 probe sets) PC1 with MR signature PC1. (e) Correlation plot of NF-kB signature PC1 (159 probe sets) with 10-gene NF-kB signature PC1. (f) Correlation plot of T cell PC1 with 10-gene NF-kB signature PC1. (g) Correlation plot of MR signature PC1 with 10-gene NF-kB signature PC1.

NF-kB signature "driver" genes (i.e., the top 10 genes with highest PCA weight) were identified as GBP1, PSMB9, IRF1, TAP1, TNFAIP3, CCL5, PSMB8, IL32, SH2B3 and NFKBIE; all are upregulated by NF-kB (see Table 1). First principal component (PC1) is associated with the largest variance of the data (e.g., variance of NF-kB signature activity in the CMCLA dataset) followed by each succeeding PC. Using association with expression of driver genes, it was found that PC1 but not PC2 is associated with NF-kB activity (FIGS. 8A-D). Using the NF-kB signature PC1, it was determined whether NF-kB activity was associated with T cell presence. For these studies, PC1 of T cell receptor α and β chain gene expression (FIG. 8E, top panel) was used. Importantly, a strong association was seen between NF-kB activity and T cell presence (r=0.68) (FIG. 8F). Therefore, while NF-kB target genes are associated with different functions in tumors, the overall NF-kB activity as determined by PCA is strongly associated with T cell presence.

Figure 8G:
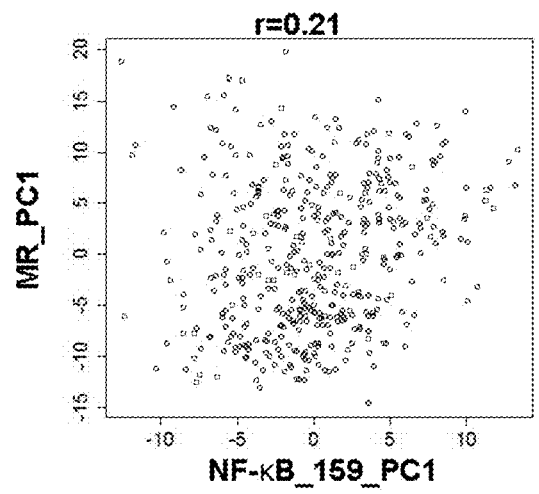

In addition to inflammation, NF-kB also exerts pro-tumor effects through cancer cell-intrinsic regulation of cell survival and proliferation (Barbie et al. 2009. Nature 462:108-112; Meylan et al., 2009. Nature 462:104-107; Maeda et al., 2005. Cell 121:977-990; Karin and Greten, 2005. Nat Rev Immunol 5:749-759; Greten et al., 2004. Cell 118:285-296; Takahashi et al., 2010. Cancer Cell 17:89-97; Basseres et al., 2010. Cancer Res 70:3537-3546). Previous studies described a breast and NSCLC malignancy-risk (MR) signature that is rich in proliferation and cell cycle genes (Chen et al., 2011. Journal of the National Cancer Institute 103:1859-1870; Chen et al., 2010. Breast cancer research and treatment 119: 335-346; Chen et al., 2010. Breast cancer research and treatment 120:25-34). Using the MR signature PC1, it was next determined whether NF-kB activity was also associated with cancer cell proliferation. However, little correlation between the NF-kB and MR signatures was noticed (r=0.21) (FIG. 8G). Thus, NF-kB activity is associated with T cell presence and potential immune surveillance functions but not with cancer cell proliferation.

Figure 8H:
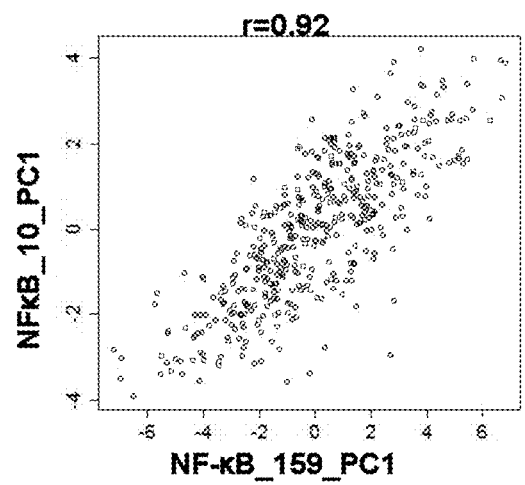
Figure 8I:
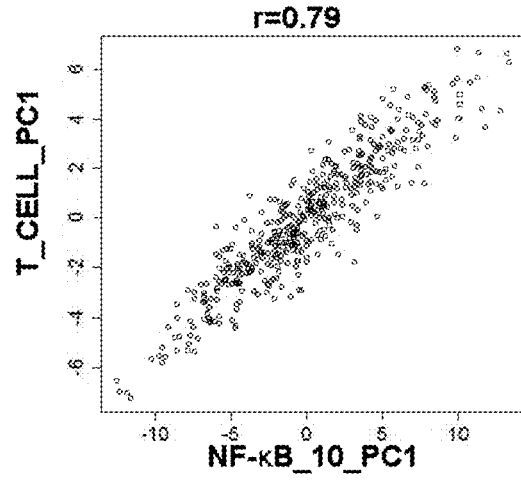
Figure 8J:
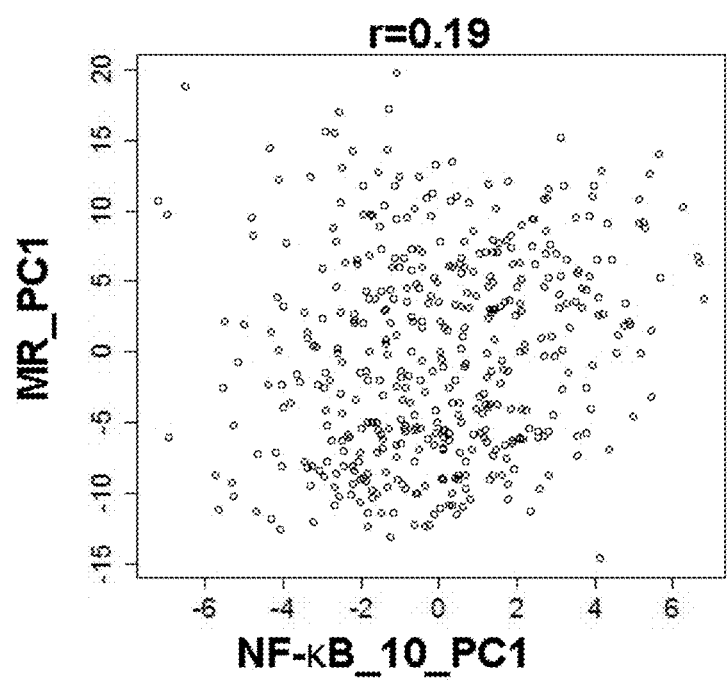
Figure 8K:
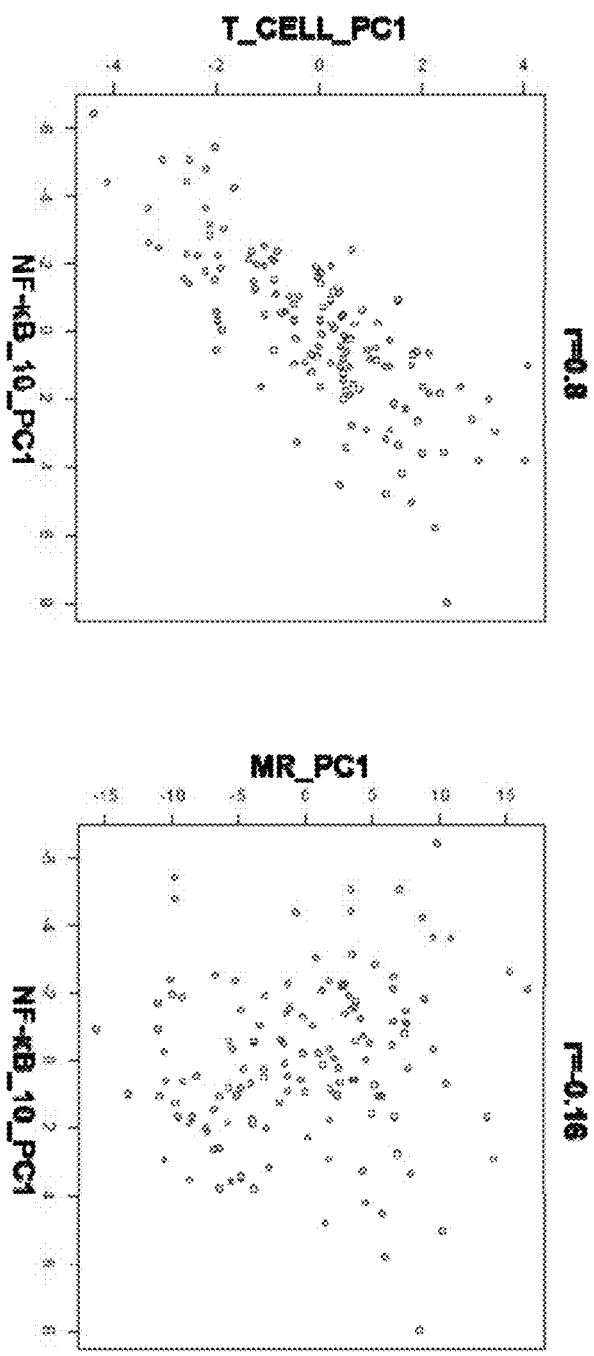
FIG. 8K. Correlation of expression between the 10-gene NF-kB signature with T cell presence and the MR signature in the GSE14814 dataset (n=133). Correlation r-values are shown.

Whether expression of the 10 driver genes mentioned above (GBP1, PSMB9, IRF1, TAP1, TNFAIP3, CCL5, PSMB8, IL32, SH2B3 and NFKBIE) was associated with overall NF-kB activity and T cell presence was also determined Indeed, PC1 of these genes (FIG. 8E, bottom panel) was highly correlated with the NF-kB signature PC1 (r=0.92) (FIG. 8H). Therefore, this smaller 10-gene signature can be used in lieu of the NF-kB signature to determine NF-kB activity. Importantly, the 10-gene PC1 was also strongly correlated with the T cell PC1 (r=0.79) (FIG. 8I) but not with the MR signature PC1 (r=0.19) (FIG. 8J). Using an additional lung cancer microarray dataset (n=133) (Zhu et al., 2010. Journal of Clinical Oncology 28:4417-4424), there was a similarly high correlation of the 10-gene signature with T cell presence (r=0.8) but not with the MR signature (r=−0.16) (FIG. 8K).

In conclusion, the present findings from both mouse and human studies indicate that tumor NF-kB activity is strongly associated with T cell presence and immune surveillance in lung cancer.

Example 8

Figure 9:
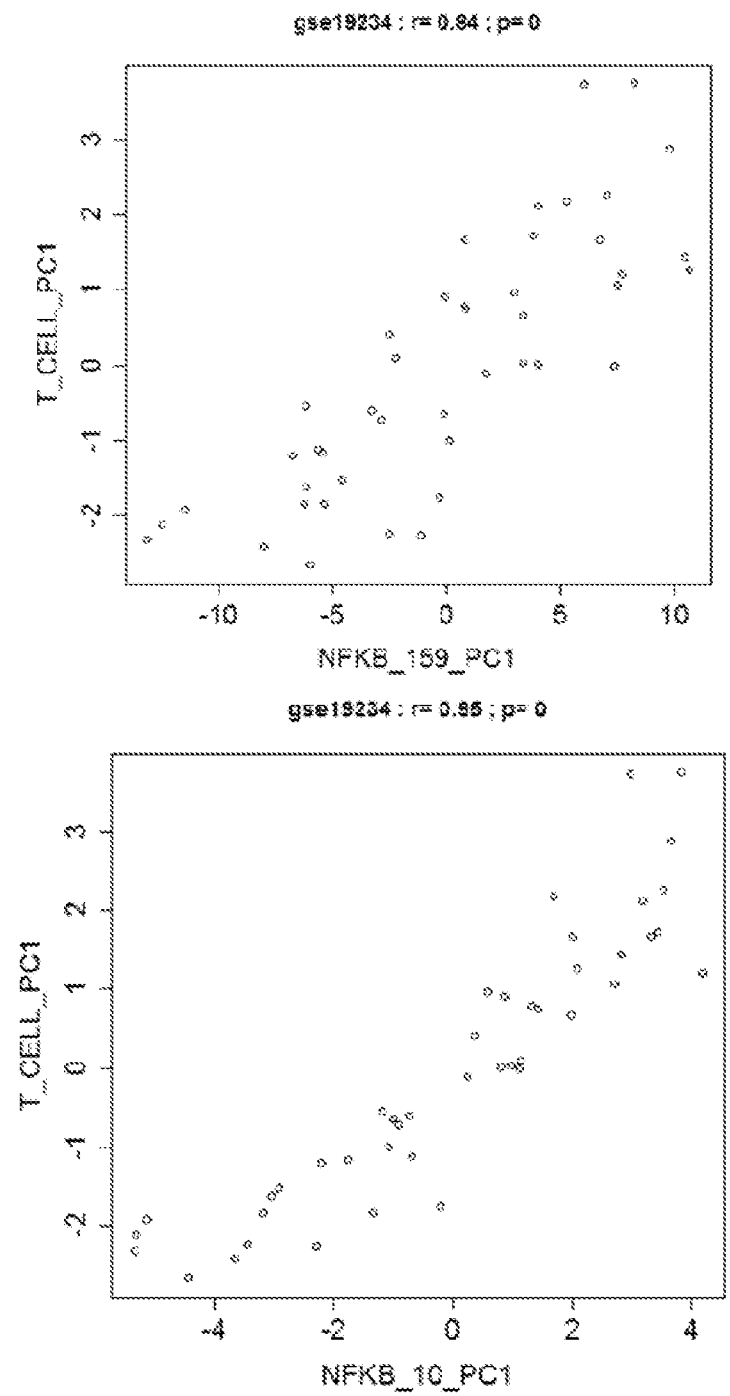
FIG. 9. Correlation plot of NF-kB signature (159 probe sets) PC1 (top panel) or 10-gene NF-kB signature PC1 (bottom panel) with T cell presence in the melanoma dataset GSE19234. Correlation r-values are shown.

NF-kB Signature Classifies Multiple Tumor Types into High and Low for the NF-kB Signature, and Correlates with Presence of T Cells A majority vote classifier as mentioned above can be used to classify different tumor types (including colon adenocarcinoma, renal carcinoma, ovarian cancer, kidney tumor, prostate tumors, and melanoma) into high and low for NF-kB signature, with similar results expected. High NF-kB signature corresponds to positive numbers and low activity corresponds to negative numbers. Each tumor class had individual samples with high, intermediate, and low NF-kB signatures. Exemplary data is shown in FIG. 9, in which PCA, performed as described above, was used to demonstrate a high degree of correlation between T cell presence and the 159 genes listed in Table 3 (r=0.84) or the 10-gene signature (r=0.95) in melanoma. This demonstrated that the classification procedure can be used in many tumor types, and also that tumors exhibit a continuum of values representing their NF-kB activity.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of selecting a treatment for a subject who has a tumor and treating the subject, the method comprising:
determining gene expression levels for GBP1, PSMB9, IRF1, TAP1, TNFAIP3, CCL5, PSMB8, IL32, SH2B3 and NFKBIE in a sample comprising cells from the tumor; and
comparing the gene expression levels to reference levels; optionally assigning a score to the tumor based on the comparison of the gene expression levels in the tumor to the reference levels;
detecting the presence of gene expression levels above the reference levels, or a score above a threshold score, and selecting a treatment for the subject comprising administering an NF-kB inhibitor or immunotherapy; or
detecting the presence of gene expression levels below the reference levels, or a score below a threshold score;
selecting a treatment for the subject comprising administering an NF-kB activator and immunotherapy, and administering the selected treatment to the subject.
2. The method of claim 1, wherein the tumor is an adenocarcinoma.
3. The method of claim 2, wherein the adenocarcinoma is lung adenocarcinoma or melanoma.
4. The method of claim 1, wherein determining gene expression levels comprises performing an assay to determine gene expression levels in the sample.
5. The method of claim 1, wherein assigning a score to the tumor based on the comparison of the gene expression levels in the tumor to the reference levels comprises using an algorithm to calculate a score.
6. The method of claim 1, wherein the NF-kB activator is an anticancer agent, preferably selected from the group consisting of taxanes, *vinca* alkaloids, and topoisomerase inhibitors.
7. The method of claim 1, wherein the NF-kB inhibitor is selected from the group consisting of sulfasalazine, Luteolin, rapamycin, temsirolimus and everolimus, caffeic acid phenethylester, SN50, parthenolide, triptolide, wedelolactone, lactacystin, substituted resorcinols, (E)-3-(4-methylphenylsulfonyl)-2-propenenitrile, Bay 11-7082, Bay 11-7821, or Bay 11-7085, Pranlukast, etoposide, bortezomib, MLN9708, PS-1145, tetrahydrocurcuminoids, Tetrahydrocurcuminoid CG, extracts of *Paulownia tomentosa* wood, and MG-132 (Z-Leu-Leu-Leu-H).
8. The method of claim 1, wherein the immunotherapy is selected from the group consisting of administration of dendritic cells or peptides with adjuvant; DNA-based vaccines; cytokines; cyclophosphamide; anti-interleukin-2R immunotoxins; and antibodies, virus-based vaccines, formulations of Toll-like Receptor or RIG-I-like receptor ligands, Adoptive T cell therapy or other cell types.
9. The method of claim 8, wherein the antibodies are selected from the group consisting of anti-CD137, anti-PD1, anti-CD40, anti-PDLL, and anti-CTLA-4 antibodies.

\* \* \* \* \*